(12) United States Patent
Hino et al.

(10) Patent No.: US 7,709,232 B2
(45) Date of Patent: May 4, 2010

(54) METHODS OF QUANTITATIVE DETECTION OF GENETIC RECOMBINANTS AND STANDARD MOLECULES FOR THE METHODS

(75) Inventors: Akihiro Hino, Tsukuba (JP); Takeshi Matsuoka, Tsukuba (JP); Hideo Kuribara, Tsukuba (JP); Tomoaki Yoshimura, Moriya (JP); Yoichiro Shindo, Moriya (JP); Satoshi Futo, Zama (JP); Machiko Ogawa, Sagamihara (JP)

(73) Assignees: National Food Research Institute, Ibaraki (JP); Asahi Breweries, Ltd., Tokyo (JP)

( * ) Notice: Subject to any disclaimer, the term of this patent is extended or adjusted under 35 U.S.C. 154(b) by 437 days.

(21) Appl. No.: 10/423,399

(22) Filed: Apr. 25, 2003

(65) Prior Publication Data
US 2004/0005605 A1 Jan. 8, 2004

Related U.S. Application Data

(63) Continuation of application No. PCT/JP01/09344, filed on Oct. 24, 2001.

(30) Foreign Application Priority Data
Oct. 26, 2000 (JP) .............................. 2000-326738

(51) Int. Cl.
C12P 1/34 (2006.01)
C12Q 1/68 (2006.01)
C07H 21/02 (2006.01)
C07H 21/04 (2006.01)
C07H 21/00 (2006.01)

(52) U.S. Cl. .................... 435/91.2; 435/6; 435/91.1; 536/23.1; 536/24.3; 536/24.33; 536/25.3

(58) Field of Classification Search .................... 435/6, 435/91.1, 91.2, 91.51, 183; 436/94; 536/23.1, 536/24.3, 24.33, 25.3, 25.32
See application file for complete search history.

(56) References Cited

U.S. PATENT DOCUMENTS
5,476,774 A 12/1995 Wang et al.

FOREIGN PATENT DOCUMENTS
WO WO 99/13113 3/1999
WO WO 01/66799 9/2001
WO WO 01/72964 10/2001

OTHER PUBLICATIONS

Important parameters of quantitative PCR analysis.*
Vaitilingom, M. et al.; Real-time Quantitative PCR Detection of Genetically Modified Maximizer Maize and Roundup Ready Soybean in some Representative Foods, J. Agric. Food Chem., 1999, vol. 47, No. 12, pp. 5261-5266.
Lallemand, F. et al.; Quantitative Analysis of Human Herpesvirus 8 Viral Load Using a Real-Time PCR Assay; J. Clin. Microbiol.; Apr. 2000; vol. 38, No. 4; pp. 1404-1408.
Hino, A. et al.; Idenshi Kumikae Nousakumotsu no Kenchi Gijutsu; Techno Innovation; Jul. 3, 2001; vol. 11, No. 4; pp. 32-27.
Matsuoka, T. et al.; Idenshi Kumikae Nousakumotsu no Atarashii Teiryo Bunsekihou no Kaihatsu, Shadan Hojin Nippon Shokuhin Eisei Gakkai, Dai 18 kai Gakujutsu Kouenkai Kouen Youshishuu; Apr. 20, 2001; p. 39.
Matsuoka, T. et al.; Idenshi Kumikae no Kenchi Gijutsu no Kaihatsu no Genjo; Norin Suisan Gijutsu Kenkyu Journal; Apr. 1, 2001; vol. 24, No. 4, pp. 28-33.
Hino, A. et al.; Journal of Japan Society for Bioscience, Biotechnology and Agrochemistry; Mar. 2000; vol. 74, extra edition, p. 87.
Matsuoka, T. et al.; A Method of Detecting Recombinant DNAs from Four Lines of Genetically Modified Maize; J. Food Hyg. Soc. Jpn.; Apr. 2000; vol. 41, No. 2; pp. 137-143.
Morrison, et al.; Rapid and Sensitive Quantification of *Borrelia burgdorferi*-Infected Mouse Tissues by Continuous Fluorescent Monitoring of PCR; Journal of Clinical Microbiology; Apr. 1999; pp. 987-992.

* cited by examiner

*Primary Examiner*—Frank W Lu
(74) *Attorney, Agent, or Firm*—Hoffmann & Baron, LLP

(57) ABSTRACT

The present invention relate to a method of detecting a genetic recombinant by using the PCR method. A method of quantitatively detecting method is provided whereby the total content ratio of the genetic recombinants and the individual content ratio of the genetic recombinant in a population containing plural genetic recombinant lines can be quantified. The method of the present invention comprises performing PCR for the DNA sequence specific to the recombinant and the endogenous DNA sequence shared by the species corresponding to the recombinant using, as a standard molecule, a molecule containing the DNA sequence specific to the recombinant and the endogenous DNA sequence shared by the species on the single molecule, and determining the content ratio of the number of molecules thereof.

8 Claims, 16 Drawing Sheets

(A) Bt11 (Novartis)
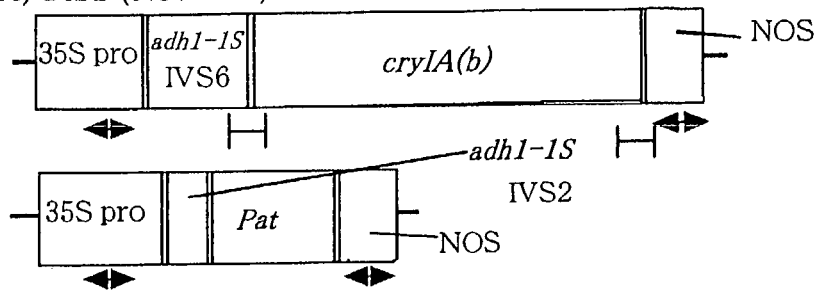
(B) MON810 (Monsanto)
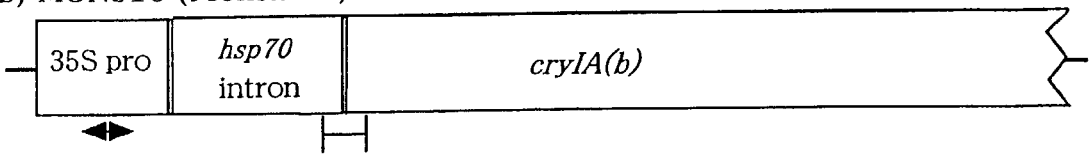
(C) T25 (Aventis)
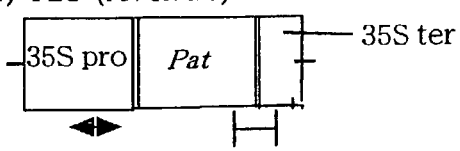
(D) Event176 (Novartis)
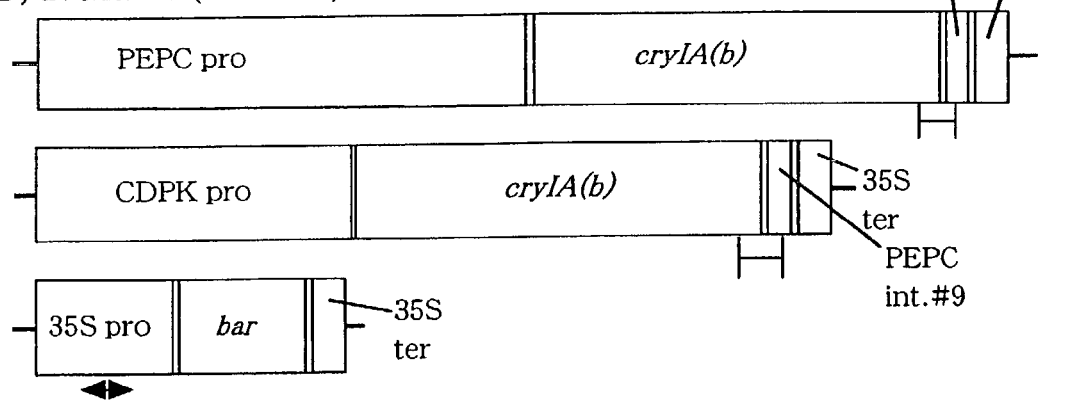
(E) GA21 (Monsanto)
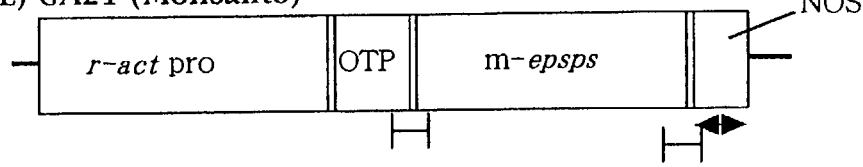
(F) Roundup Ready Soy (Monsanto)
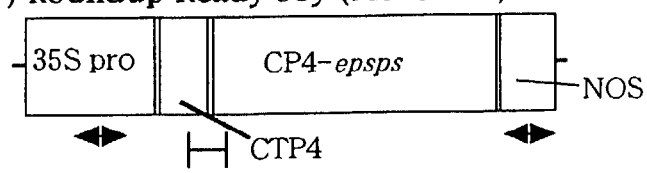
FIG. 1

FIG. 2

USED PRIMER: T25 1-5' / T25 1-3'
(FOR T25 DETECTION)

| | NON-RECOM-BINANT MAIZE | Event176 | Bt11 | T25 | MON810 | GA21 | NON-RECOMBINANT SOYBEAN | Roundup Ready Soy | RICE | WHEAT | BARELY | NO DNA |
|---|---|---|---|---|---|---|---|---|---|---|---|---|
| THE EXISTENCE OF THE BAND LENGTH OF AMPLIFIED BAND (bp) | — | — | — | +<br>149 | — | — | — | — | — | — | — | — |

FIG. 5

```
         ┌─ SSIIb AMPLICON
    1    │CTCCCAATCCTTTGACATCTGCTCCGAAGCAAAGTCAGAGCGCTGCAATGCAAAACGGAA
         │GAGGGTTAGGAAACTGTAGACGAGGCTTCGTTTCAGTCTCGCGACGTTACGTTTTGCCTT
                                ────▶

61    CGAGTGGGGGCAGCAGCGCGAGCACCGCCGCGCCGGTGTCCGGACCCAAAGCTGATCATC
         GCTCACCCCCGTCGTCGCGCTCGTGGCGGCGCGGCCACAGGCCTGGGTTTCGACTAGTAG
                                                      ◀──┬─▶ P35S AMPLICON
  121    CATCAGCTCCTGTCACCAAGAGAGAAATCGACCTCTCCAAATGAAATGAACTTCCTTATA
         GTAGTCGAGGACAGTGGTTCTCTCTTTAGCTGGAGAGGTTTACTTTACTTGAAGGAATAT
              ◀─────                                 ─────▶
  181    TAGAGGAAGGGTCTTGCGAAGGATAGTGGGATTGTGCGTCATCCCTTACGTCAGTGGAGA
         ATCTCCTTCCCAGAACGCTTCCTATCACCCTAACACGCAGTAGGGAATGCAGTCACCTCT
                        ─Srf I site─    ─▶ NOS AMPLICON   ◀─────
  241    TATCACATCAAT GCCCGGGC AATCCTGTTGCCGGTCTTGCGATGATTATCATATAATTT
         ATAGTGTAGTTA CGGGCCCG TTAGGACAACGGCCAGAACGCTACTAATAGTATATTAAA
                     ◀───────            ──────────────────────────
  301    CTGTTGAATTACGTTAAGCATGTAATAATTAACATGTAATGCATGACGTTATTTATGAGA
         GACAACTTAATGCAATTCGTACATTATTAATTGTACATTACGTACTGCAATAAATACTCT
         ─▶
  361    TGGGTTTTTATGATTAGAGTCCCGCAATTATACATTTAATACGCGATAGAAAACAAAATA
         ACCCAAAAATACTAATCTCAGGGCGTTAATATGTAAATTATGCGCTATCTTTTGTTTTAT
                           ◀─┬─▶ GA21 AMPLICON    ◀─────
  421    TAGCGCGCAAACTAGGATAA ATCGCAAGACCGGCAACAGGATTCAATCTTAAGAAACTTT
         ATCGCGCGTTTGATCCTATT TAGCGTTCTGGCCGTTGTCCTAAGTTAGAATTCTTTGAAA
         ─────                                    ─────▶
  481    ATTGCCAAATGTTTGAACGATCGGGGAAATTCGTCGAAGCTTCTTCTAGAGCTTAATTCT
         TAACGGTTTACAAACTTGCTAGCCCCTTTAAGCAGCTTCGAAGAAGATCTCGAATTAAGA
                                                    ─┬─▶ T25 AMPLICON
  541    TGACGAAAGTGCTCAGCACATCGAAGTAGTCGGGGAAGGTC TGAGCGAAACCCTATAAGA
         ACTGCTTTCACGAGTCGTGTAGCTTCATCAGCCCCTTCCAG ACTCGCTTTGGGATATTCT
                                                ◀─
  601    ACCCTAATTCCCTTATCTGGGAACTACTCACACATTATTATAGAGAGAGATAGATTTGTA
         TGGGATTAAGGGAATAGACCCTTGATGAGTGTGTAATAATATCTCTCTCTATCTAAACAT
         ──▶
  661    GAGAGAGACTGGTGATTTCAGCGGGCATGCCTGCAGGTCGACTCAGATCTGGGTAACTGG
         CTCTCTCTGACCACTAAAGTCGCCCGTACGGACGTCCAGCTGAGTCTAGACCCATTGACC
                          ─┬─▶ M810 AMPLICON              ◀─────
  721    CCTAACTGGC GGATGCACTCGTTGATGTTTGGGTTGTTGTCCATGGCCGCTTGGTATCTG
         GGATTGACCG CCTACGTGAGCAACTACAAACCCAACAACAGGTACCGGCGAACCATAGAC
         ──────────                                  ─────▶
  781    CATTACAATGAAATGAGCAAAGACTATGTGAGTAACACTGGTCAACACTAGGGAGAAGGC
         GTAATGTTACTTTACTCGTTTCTGATACACTCATTGTGACCAGTTGTGATCCCTCTTCCG
                  ◀─┬─▶ E176 AMPLICON
  841    ATC GACTGACTACTCCACTTTGTGCAGAACAGATCTAGAGCTCCTACACCTGATCGATGT
         TAG CTGACTGATGAGGTGAAACACGTCTTGTCTAGATCTCGAGGATGTGGACTAGCTACA
         ───                                   ─────▶      ◀─┬─▶ Bt11 AMPLICON
  901    GGTAGTCGGTCACGTCGGTCTTCAGGCCGATCTGGTTGCTGCTGGTGAACA CGGCAACAG
         CCATCAGCCAGTGCAGCCAGAAGTCCGGCTAGACCAACGACGACCACTTGT GCCGTTGTC
                                                ◀─────
  961    GATTCAATCTTAAGAAACTTTATTGCCAAATGTTTGAACGATCCTGATCTTCAGTACTCA
         CTAAGTTAGAATTCTTTGAAATAACGGTTTACAAACTTGCTAGGACTAGAAGTCATGAGT
         ─────▶
 1021    GCCTCGAAGGTAACTTCGGCAGGCACAAACTCAATACGGTCAATGTACACTTCATTGCCA
         CGGAGCTTCCATTGAAGCCGTCCGTGTTTGAGTTATGCCAGTTACATGTGAAGTAACGGT
                                                                  ◀─
 1081    GAATTGAACACATGAGCGCTAA
         CTTAACTTGTGTACTCGCGATT
         ─────
```

◀── ── ──▶ PRIMER REGION

──────── TaqMan PROBE REGION

FIG. 6

```
         →SS11b AMPLICON
    1   CTCCCAATCCTTTGACATCTGCTCCGAAGCAAAGTCAGAGCGCTGCAATGCAAAACGGAA
        GAGGGTTAGGAAACTGTAGACGAGGCTTCGTTTCAGTCTCGCGACGTTACGTTTTGCCTT

61   CGAGTGGGGGCAGCAGCGCGAGCACCGCCGCGCCGGTGTCCGGACCCAAAGCTGATCATC
        GCTCACCCCCGTCGTCGCGCTCGTGGCGGCGCGGCCACAGGCCTGGGTTTCGACTAGTAG
                                          ←   →P35S AMPLICON
  121   CATCAGCTCCTGTCACCAAGAGAGAAATCGACCTCTCCAAATGAAATGAACTTCCTTATA
        GTAGTCGAGGACAGTGGTTCTCTCTTTAGCTGGAGAGGTTTACTTTACTTGAAGGAATAT

181   TAGAGGAAGGGTCTTGCGAAGGATAGTGGGATTGTGCGTCATCCCTTACGTCAGTGGAGA
        ATCTCCTTCCCAGAACGCTTCCTATCACCCTAACACGCAGTAGGGAATGCAGTCACCTCT
                ← Srf1 site →NOS AMPLICON
  241   TATCACATCAATGCCCGGGCGAATCCTGTTGCCGGTCTTGCGATGATTATCATATAATTT
        ATAGTGTAGTTACGGGCCCGCTTAGGACAACGGCCAGAACGCTACTAATAGTATATTAAA 301   CTGTTGAATTACGTTAAGCATGTAATAATTAACATGTAATGCATGACGTTATTTATGAGA
        GACAACTTAATGCAATTCGTACATTATTAATTGTACATTACGTACTGCAATAAATACTCT 361   TGGGTTTTTATGATTAGAGTCCCGCAATTATACATTTAATACGCGATAGAAAACAAAATA
        ACCCAAAAATACTAATCTCAGGGCGTTAATATGTAAATTATGCGCTATCTTTTGTTTTAT
                     ← →GA21 AMPLICON
  421   TAGCGCGCAAACTAGGATAAATCCGGTTGGAAAGCGACTTGGACCCCGGCAGCTTGACGG
        ATCGCGCGTTTGATCCTATTTAGGCCAACCTTTCGCTGAACCTGGGGCCGTCGAACTGCC 481   TGCCGGAGATCTCCTTGATGGGCTGCAGCACGATCTCCTCGGCGCCGGCCATGCACCGGA
        ACGGCCTCTAGAGGAACTACCCGACGTCGTGCTAGAGGAGCCGCGGCCGGTACGTGGCCT
                                        ← →T25 AMPLICON
  541   TCCTTCCGCCGTTGCTGACGTTGCCGAGGCTTCTGAGCGAAACCCTATAAGAACCCTAAT
        AGGAAGGCGGCAACGACTGCAACGGCTCCGAAGACTCGCTTTGGGATATTCTTGGGATTA 601   TCCCTTATCTGGGAACTACTCACACATTATTATAGAGAGAGATAGATTTGTAGAGAGAGA
        AGGGAATAGACCCTTGATGAGTGTGTAATAATATCTCTCTCTATCTAAACATCTCTCTCT 661   CTGGTGATTTCAGCGGGCATGCCTGCAGGTCGACTCAGATCTGGGTAACTGGCCTAACTG
        GACCACTAAAGTCGCCCGTACGGACGTCCAGCTGAGTCTAGACCCATTGACCGGATTGAC
        ← →MON810 AMPLICON
  721   GCGGATGCACTCGTTGATGTTTGGGTTGTTGTCCATGGCCGCTTGGTATCTGCATTACAA
        CGCCTACGTGAGCAACTACAAACCCAACAACAGGTACCGGCGAACCATAGACGTAATGTT
                                                              ← →
  781   TGAAATGAGCAAAGACTATGTGAGTAACACTGGTCAACACTAGGGAGAAGGCATCGACTG
        ACTTTACTCGTTTCTGATACACTCATTGTGACCAGTTGTGATCCCTCTTCCGTAGCTGAC
        E176 AMPLICON
  841   ACTACTCCACTTTGTGCAGAACAGATCTAGAGCTCCTACACCTGATCGATGTGGTAGTCG
        TGATGAGGTGAAACACGTCTTGTCTAGATCTCGAGGATGTGGACTAGCTACACCATCAGC
                                                 ← →Bt11 AMPLICON
  901   GTCACGTCGGTCTTCAGGCCGATCTGGTTGCTGCTGGTGAACATCAATGCGTTCTCCACC
        CAGTGCAGCCAGAAGTCCGGCTAGACCAACGACGACCACTTGTAGTTACGCAAGAGGTGG 961   AAGTACTTCAACTTCTGGGTTACTCAAGCAGTTGTATGGAATGCATTCGTTGATGTTTGG
        TTCATGAAGTTGAAGACCCAATGAGTTCGTCAACATACCTTACGTAAGCAACTACAAACC 1021   GTTGTTGTCCATGGTCGACTCTAGAGGATCCGCGGCTTGTTGTGGTCTTTT  1071
        CAACAACAGGTACCAGCTGAGATCTCCTAGGCGCCGAACAACACCAGAAAA ←---------  ---------→ PRIMER REGION
                     _____ TaqMan PROBE REGION
```

FIG. 8

C-EP AMPLICON

1  CCTTTAGGATTTCAGCATCAGTGGCTACAGCCTGCATGCTTCACGGTGCAAGCAGCCGGC
   GGAAATCCTAAAGTCGTAGTCACCGATGTCGGACGTACGAAGTGCCACGTTCGTCGGCCG

61 CCGCAACCGCCCGCAAATCCTCTGGCCTTTCCGGAACCGTCCGCATTCCCGGCGACAAGT
   GGCGTTGGCGGGCGTTTAGGAGACCGGAAAGGCCTTGGCAGGCGTAAGGGCCGCTGTTCA

Le1 AMPLICON

121 CGCCCATCTGCAAGCCTTTTTGTGTCAGGGGCATAGAAGGTGAAGTTGAAGGAAGCGGCG
    GCGGGTAGACGTTCGGAAAAACACAGTCCCCGTATCTTCCACTTCAACTTCCTTCGCCGC

181 AAGCTGGCAACGCTACCGGTTTCTTTGTCCCAAATGTGGATGGGGGTGGAGTAGAGGGC
    TTCGACCGTTGCGATGGCCAAAGAAACAGGGTTTACACCTACCCCCACCTCATCTCCCG

◀— — —▶ PRIMER REGION
———————— TaqMan PROBE REGION

FIG. 9

→C-EP AMPLICON

```
  1  CCTTTAGGATTTCAGCATCAGTGGCTACAGCCTGCATGCTTCACGGTGCAAGCAGCCGGC
     GGAAATCCTAAAGTCGTAGTCACCGATGTCGGACGTACGAAGTGCCACGTTCGTCGGCCG
     ----------------------▶

61  CCGCAACCGCCCGCAAATCCTCTGGCCTTTCCGGAACCGTCCGCATTCCCGGCGACAAGT
     GGCGTTGGCGGGCGTTTAGGAGACCGGAAAGGCCTTGGCAGGCGTAAGGGCCGCTGTTCA
                                                  ◀----------------------
```

← →Le1 AMPLICON

```
121  CGCCCATCTGCAAGCCTTTTTGTGTCAGGGGCATAGAAGGTGAAGTTGAAGGAAGCGGCG
     GCGGGTAGACGTTCGGAAAAACACAGTCCCCGTATCTTCCACTTCAACTTCCTTCGCCGC
     -+----------------------▶

← →
181  AAGCTGGCAACGCTACCGGTTTCTTTGTCCCAAATGTGGATGGGGGTGGAGTAGAGGGCT
     TTCGACCGTTGCGATGGCCAAAGAAACAGGGTTTACACCTACCCCCACCTCATCTCCCGA
                                                  ◀----------------------
```

NOS AMPLICON

```
241  TATCCTAGTTTGCGCGCTATATTTTGTTTTCTATCGCGTATTAAATGTATAATTGCGGGA
     ATAGGATCAAACGCGCGATATAAAACAAAAGATAGCGCATAATTTACATATTAACGCCCT
                                  ----------------------▶

301  CTCTAATCATAAAAACCCATCTCATAAATAACGTCATGCATTACATGTTAATTATTACAT
     GAGATTAGTATTTTTGGGTAGAGTATTTATTGCAGTACGTAATGTACAATTAATAATGTA

←
361  GCTTAACGTAATTCAACAGAAATTATATGATAATCATCGCAAGACCGGCAACAGGATTC
     CGAATTGCATTAAGTTGTCTTTAATATACTATTAGTAGCGTTCTGGCCGTTGTCCTAAG
                        ◀----------------------
```

Srf I site →P35S AMPLICON

```
421  CCCGGGCATTGATGTGATATCTCCACTGACGTAAGGGATGACGCACAATCCCACTATCCT
     GGGCCCGTAACTACACTATAGAGGTGACTGCATTCCCTACTGCGTGTTAGGGTGATAGGA
                   ----------------------▶

←
481  TCGCAAGACCCTTCCTCTATATAAGGAAGTTCATTTCATTTGGAGAGG   528
     AGCGTTCTGGGAAGGAGATATATTCCTTCAAGTAAAGTAAACCTCTCC
                                  ◀----------------------
```

◀---------- ----------▶ PRIMER REGION
────────── TaqMan PROBE REGION

| PRIMER | zSSIIb DETECTION | | | CaMV 35S PROMOTER DETECTION | | | NOS terminator DETECTION | | | Bt11 DETECTION | | |
|---|---|---|---|---|---|---|---|---|---|---|---|---|
| TEMPLATE | SAMPLE | NO DNA | pMul4 BamHI DIGEST | SAMPLE | NO DNA | pMul4 BamHI DIGEST | SAMPLE | NO DNA | pMul4 BamHI DIGEST | SAMPLE | NO DNA | pMul4 BamHI DIGEST |
| EXISTENCE OF THE BAND | + | - | + | + | - | + | + | - | + | + | - | + |
| AMPLIFIED LENGTH | 151 | | 151 | 101 | | 101 | 151 | | 151 | 151 | | 151 |

(B)

| PRIMER | T25 DETECTION | | | GA21 DETECTION | | | Event176 DETECTION | | | MON810 DETECTION | | |
|---|---|---|---|---|---|---|---|---|---|---|---|---|
| TEMPLATE | SAMPLE | NO DNA | pMul4 BamHI DIGEST | SAMPLE | NO DNA | pMul4 BamHI DIGEST | SAMPLE | NO DNA | pMul4 BamHI DIGEST | SAMPLE | NO DNA | pMul4 BamHI DIGEST |
| EXISTENCE OF THE BAND | - | - | + | + | - | + | - | - | + | + | - | + |
| AMPLIFIED LENGTH | | | 149 | 141 | | 141 | | | 100 | 113 | | 113 |

FIG. 14
(A)
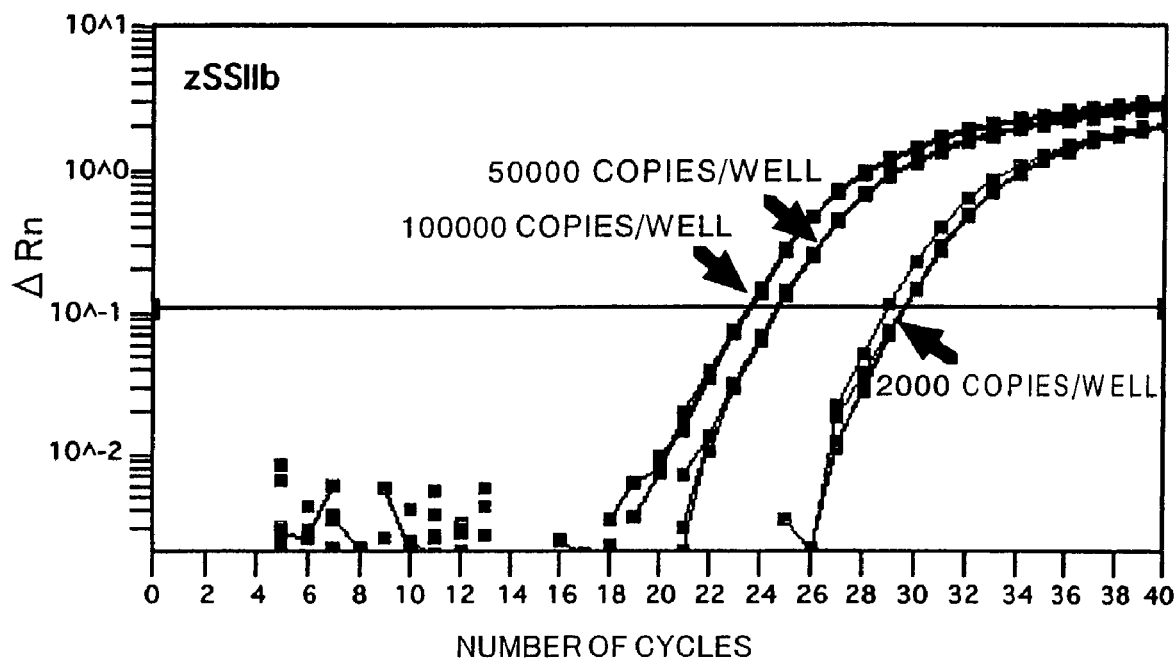
(B)
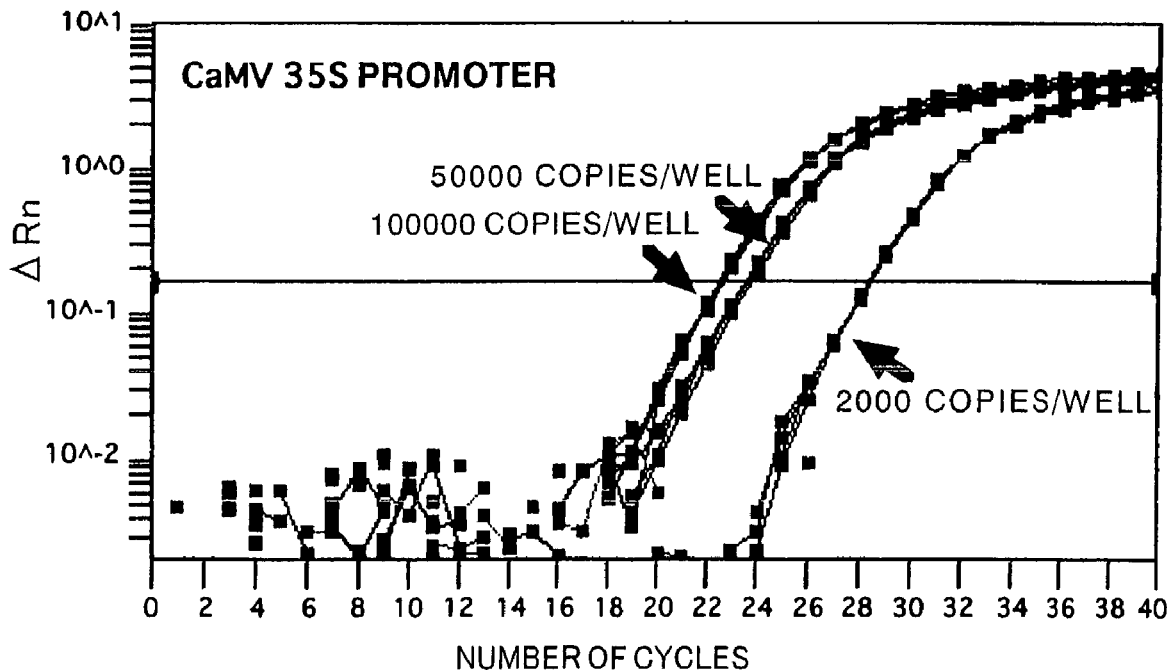

FIG. 15
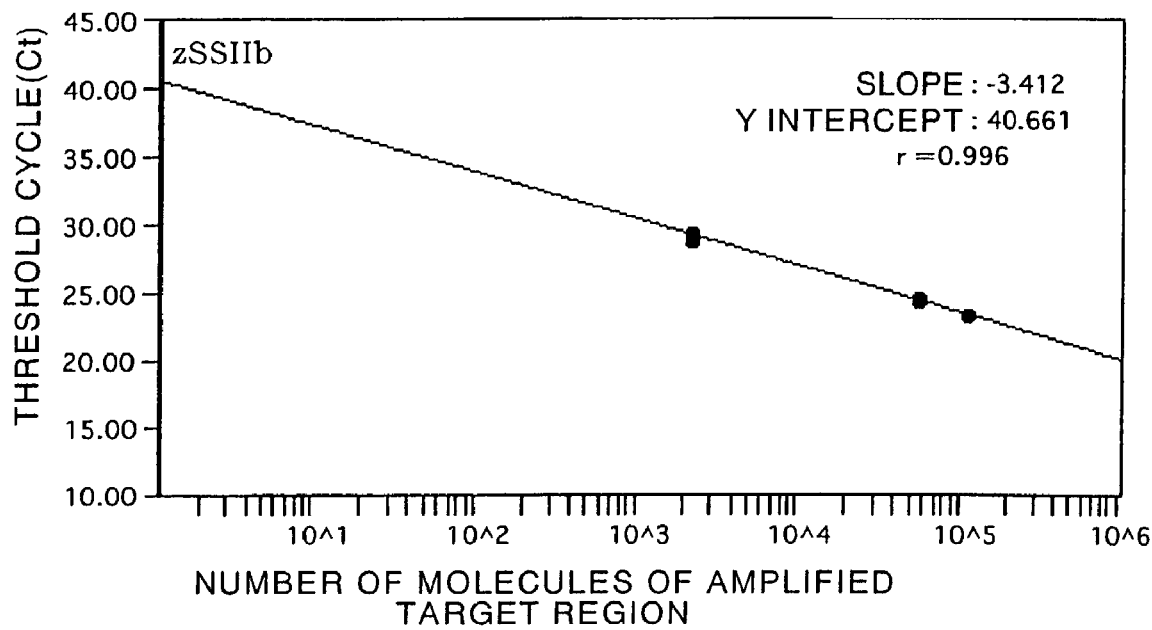
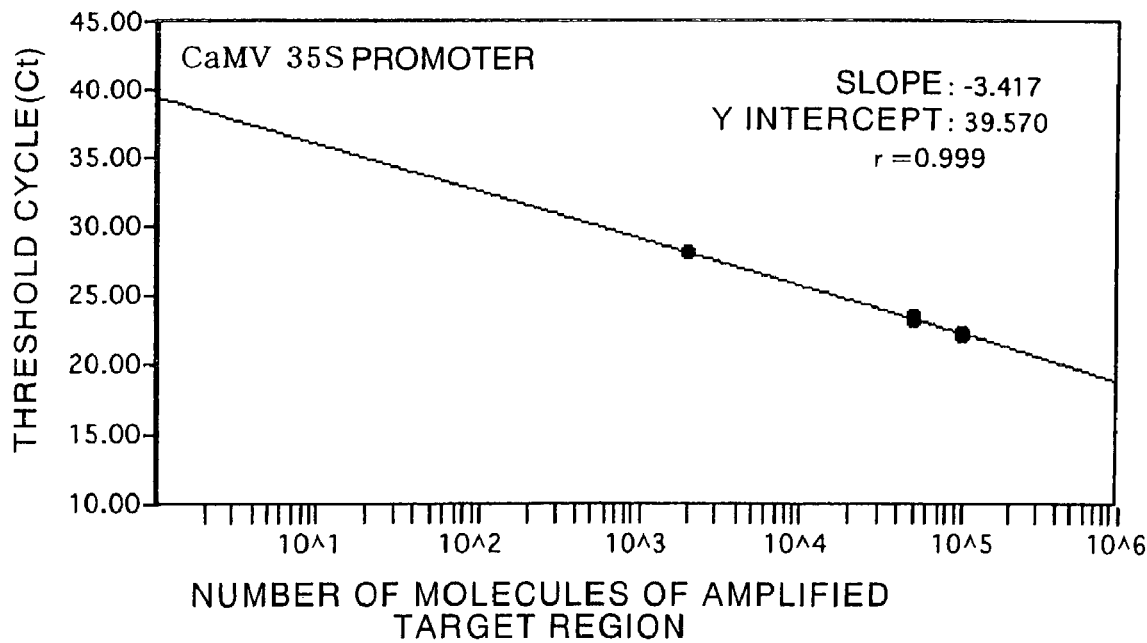

SEQUENCE LISTING

```
<160> NUMBER OF SEQ ID NOS: 80

<210> SEQ ID NO 1
<211> LENGTH: 22
<212> TYPE: DNA
<213> ORGANISM: Artificial Sequence
<220> FEATURE:
<223> OTHER INFORMATION: PCR primer

<400> SEQUENCE: 1
tggacaacaa cccaaacatc aa                                              22

<210> SEQ ID NO 2
<211> LENGTH: 26
<212> TYPE: DNA
<213> ORGANISM: Artificial Sequence
<220> FEATURE:
<223> OTHER INFORMATION: PCR primer

<400> SEQUENCE: 2
tggattttgg ttttaggaat tagaaa                                          26

<210> SEQ ID NO 3
<211> LENGTH: 19
<212> TYPE: DNA
<213> ORGANISM: Artificial Sequence
<220> FEATURE:
<223> OTHER INFORMATION: PCR primer

<400> SEQUENCE: 3
gcactgaatt tgtgaaccc                                                  19

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
ctatattttg ttttctatcg c                                               21

<210> SEQ ID NO 5
<211> LENGTH: 25
<212> TYPE: DNA
<213> ORGANISM: Artificial Sequence
<220> FEATURE:
<223> OTHER INFORMATION: PCR primer

<400> SEQUENCE: 5
attgatgtga tatctccact gacgt                                           25
```

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
ttatcctagt ttgcgcgcta                                         20

<210> SEQ ID NO 7
<211> LENGTH: 21
<212> TYPE: DNA
<213> ORGANISM: Artificial Sequence
<220> FEATURE:
<223> OTHER INFORMATION: PCR primer

<400> SEQUENCE: 7
atctttggcc ttggtagttt g                                       21

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
attgcgggac tctaatcata a                                       21

<210> SEQ ID NO 9
<211> LENGTH: 25
<212> TYPE: DNA
<213> ORGANISM: Artificial Sequence
<220> FEATURE:
<223> OTHER INFORMATION: PCR primer

<400> SEQUENCE: 9
attgatgtga tatctccact gacgt                                   25

<210> SEQ ID NO 10
<211> LENGTH: 26
<212> TYPE: DNA
<213> ORGANISM: Artificial Sequence
<220> FEATURE:
<223> OTHER INFORMATION: PCR primer

<400> SEQUENCE: 10
actaagggtt tcttatatgc tcaaca                                  26

<210> SEQ ID NO 11
<211> LENGTH: 25
<212> TYPE: DNA
<213> ORGANISM: Artificial Sequence
<220> FEATURE:
<223> OTHER INFORMATION: PCR primer

<400> SEQUENCE: 11
cactacaaat gccatcattg cgata                                   25

<210> SEQ ID NO 12
<211> LENGTH: 21
<212> TYPE: DNA
<213> ORGANISM: Artificial Sequence
<220> FEATURE:

```
<223> OTHER INFORMATION: PCR primer

<400> SEQUENCE: 12
gatgtttggg ttgttgtcca t                                              21

<210> SEQ ID NO 13
<211> LENGTH: 24
<212> TYPE: DNA
<213> ORGANISM: Artificial Sequence
<220> FEATURE:
<223> OTHER INFORMATION: PCR primer

<400> SEQUENCE: 13
ccttcgcaag acccttcctc tata                                           24

<210> SEQ ID NO 14
<211> LENGTH: 24
<212> TYPE: DNA
<213> ORGANISM: Artificial Sequence
<220> FEATURE:
<223> OTHER INFORMATION: PCR primer

<400> SEQUENCE: 14
atcctggcgc ccatggcctg catg                                           24

<210> SEQ ID NO 15
<211> LENGTH: 22
<212> TYPE: DNA
<213> ORGANISM: Artificial Sequence
<220> FEATURE:
<223> OTHER INFORMATION: PCR primer

<400> SEQUENCE: 15
ctcccaatcc tttgacatct gc                                             22

<210> SEQ ID NO 16
<211> LENGTH: 23
<212> TYPE: DNA
<213> ORGANISM: Artificial Sequence
<220> FEATURE:
<223> OTHER INFORMATION: PCR primer

<400> SEQUENCE: 16
tcgatttctc tcttggtgac agg                                            23

<210> SEQ ID NO 17
<211> LENGTH: 25
<212> TYPE: DNA
<213> ORGANISM: Artificial Sequence
<220> FEATURE:
<223> OTHER INFORMATION: probe for maize SSIIb
<220> FEATURE:
<221> NAME/KEY: modified_base
<222> LOCATION: (1)..(1)
<223> OTHER INFORMATION: Fam-a
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (25)..(25)
<223> OTHER INFORMATION: a-Tamra
<220> FEATURE:
<221> NAME/KEY: misc_feature
<222> LOCATION: (25)..(25)
<223> OTHER INFORMATION: n is a, c, g, or t

<400> SEQUENCE: 17
```
ngcaaagtca gagcgctgca atgcn                                      25

<210> SEQ ID NO 18
<211> LENGTH: 25
<212> TYPE: DNA
<213> ORGANISM: Artificial Sequence
<220> FEATURE:
<223> OTHER INFORMATION: PCR primer

<400> SEQUENCE: 18
attgatgtga tatctccact gacgt                                      25

<210> SEQ ID NO 19
<211> LENGTH: 25
<212> TYPE: DNA
<213> ORGANISM: Artificial Sequence
<220> FEATURE:
<223> OTHER INFORMATION: PCR primer

<400> SEQUENCE: 19
cctctccaaa tgaaatgaac ttcct                                      25

<210> SEQ ID NO 20
<211> LENGTH: 27
<212> TYPE: DNA
<213> ORGANISM: Artificial Sequence
<220> FEATURE:
<223> OTHER INFORMATION: probe for CaMV35S promoter
<220> FEATURE:
<221> NAME/KEY: modified_base
<222> LOCATION: (1)..(1)
<223> OTHER INFORMATION: Fam-c
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (27)..(27)
<223> OTHER INFORMATION: t-Tamra
<220> FEATURE:
<221> NAME/KEY: misc_feature
<222> LOCATION: (27)..(27)
<223> OTHER INFORMATION: n is a, c, g, or t

<400> SEQUENCE: 20
nccactatcc ttcgcaagac ccttccn                                    27

<210> SEQ ID NO 21
<211> LENGTH: 29
<212> TYPE: DNA
<213> ORGANISM: Artificial Sequence
<220> FEATURE:
<223> OTHER INFORMATION: PCR primer

<400> SEQUENCE: 21
gtcttgcgat gattatcata taatttctg                                  29

<210> SEQ ID NO 22
<211> LENGTH: 25
<212> TYPE: DNA
<213> ORGANISM: Artificial Sequence
<220> FEATURE:
<223> OTHER INFORMATION: PCR primer

<400> SEQUENCE: 22
cgctatattt tgttttctat cgcgt                                      25

```
<210> SEQ ID NO 23
<211> LENGTH: 30
<212> TYPE: DNA
<213> ORGANISM: Artificial Sequence
<220> FEATURE:
<223> OTHER INFORMATION: probe for NOS terminator
<220> FEATURE:
<221> NAME/KEY: modified_base
<222> LOCATION: (1)..(1)
<223> OTHER INFORMATION: Fam-a
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (30)..(30)
<223> OTHER INFORMATION: a-Tamra
<220> FEATURE:
<221> NAME/KEY: misc_feature
<222> LOCATION: (30)..(30)
<223> OTHER INFORMATION: n is a, c, g, or t

<400> SEQUENCE: 23
ngatgggttt ttatgattag agtcccgcan                                30

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
tgttcaccag cagcaaccag                                           20

<210> SEQ ID NO 25
<211> LENGTH: 25
<212> TYPE: DNA
<213> ORGANISM: Artificial Sequence
<220> FEATURE:
<223> OTHER INFORMATION: PCR primer

<400> SEQUENCE: 25
actccacttt gtgcagaaca gatct                                     25

<210> SEQ ID NO 26
<211> LENGTH: 25
<212> TYPE: DNA
<213> ORGANISM: Artificial Sequence
<220> FEATURE:
<223> OTHER INFORMATION: probe for Event176
<220> FEATURE:
<221> NAME/KEY: modified_base
<222> LOCATION: (1)..(1)
<223> OTHER INFORMATION: Fam-c
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (25)..(25)
<223> OTHER INFORMATION: a-Tamra
<220> FEATURE:
<221> NAME/KEY: misc_feature
<222> LOCATION: (25)..(25)
<223> OTHER INFORMATION: n is a, c, g, or t

<400> SEQUENCE: 26
ncgacgtgac cgactaccac atcgn                                     25
```

```
<210> SEQ ID NO 27
<211> LENGTH: 23
<212> TYPE: DNA
<213> ORGANISM: Artificial Sequence
<220> FEATURE:
<223> OTHER INFORMATION: PCR primer

<400> SEQUENCE: 27
ttagcgctca tgtgttcaat tct                                              23

<210> SEQ ID NO 28
<211> LENGTH: 22
<212> TYPE: DNA
<213> ORGANISM: Artificial Sequence
<220> FEATURE:
<223> OTHER INFORMATION: PCR primer

<400> SEQUENCE: 28
cggcaacagg attcaatctt aa                                               22

<210> SEQ ID NO 29
<211> LENGTH: 29
<212> TYPE: DNA
<213> ORGANISM: Artificial Sequence
<220> FEATURE:
<223> OTHER INFORMATION: probe for Bt11
<220> FEATURE:
<221> NAME/KEY: modified_base
<222> LOCATION: (1)..(1)
<223> OTHER INFORMATION: Fam-a
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (29)..(29)
<223> OTHER INFORMATION: c-Tamra
<220> FEATURE:
<221> NAME/KEY: misc_feature
<222> LOCATION: (29)..(29)
<223> OTHER INFORMATION: n is a, c, g, or t

<400> SEQUENCE: 29
ncattgaccg tattgagttt gtgcctgcn                                        29

<210> SEQ ID NO 30
<211> LENGTH: 21
<212> TYPE: DNA
<213> ORGANISM: Artificial Sequence
<220> FEATURE:
<223> OTHER INFORMATION: PCR primer

<400> SEQUENCE: 30
gaccttcccc gactacttcg a                                                21

<210> SEQ ID NO 31
<211> LENGTH: 18
<212> TYPE: DNA
<213> ORGANISM: Artificial Sequence
<220> FEATURE:
<223> OTHER INFORMATION: PCR primer

<400> SEQUENCE: 31
atcgcaagac cggcaaca                                                    18

<210> SEQ ID NO 32
```

```
<211> LENGTH: 27
<212> TYPE: DNA
<213> ORGANISM: Artificial Sequence
<220> FEATURE:
<223> OTHER INFORMATION: probe for GA21
<220> FEATURE:
<221> NAME/KEY: modified_base
<222> LOCATION: (1)..(1)
<223> OTHER INFORMATION: Fam-c
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (27)..(27)
<223> OTHER INFORMATION: t-Tamra
<220> FEATURE:
<221> NAME/KEY: misc_feature
<222> LOCATION: (27)..(27)
<223> OTHER INFORMATION: n is a, c, g, or t

<400> SEQUENCE: 32
ngaatttccc cgatcgttca aacattn                                       27

<210> SEQ ID NO 33
<211> LENGTH: 21
<212> TYPE: DNA
<213> ORGANISM: Artificial Sequence
<220> FEATURE:
<223> OTHER INFORMATION: PCR primer

<400> SEQUENCE: 33
gccagttagg ccagttaccc a                                             21

<210> SEQ ID NO 34
<211> LENGTH: 24
<212> TYPE: DNA
<213> ORGANISM: Artificial Sequence
<220> FEATURE:
<223> OTHER INFORMATION: PCR primer

<400> SEQUENCE: 34
tgagcgaaac cctataagaa ccct                                          24

<210> SEQ ID NO 35
<211> LENGTH: 26
<212> TYPE: DNA
<213> ORGANISM: Artificial Sequence
<220> FEATURE:
<223> OTHER INFORMATION: probe for T25
<220> FEATURE:
<221> NAME/KEY: modified_base
<222> LOCATION: (1)..(1)
<223> OTHER INFORMATION: Fam-c
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (26)..(26)
<223> OTHER INFORMATION: t-Tamra
<220> FEATURE:
<221> NAME/KEY: misc_feature
<222> LOCATION: (26)..(26)
<223> OTHER INFORMATION: n is a, c, g, or t

<400> SEQUENCE: 35
natgcccgct gaaatcacca gtctcn                                        26
```

```
<210> SEQ ID NO 36
<211> LENGTH: 22
<212> TYPE: DNA
<213> ORGANISM: Artificial Sequence
<220> FEATURE:
<223> OTHER INFORMATION: PCR primer

<400> SEQUENCE: 36
gatgccttct ccctagtgtt ga                                            22

<210> SEQ ID NO 37
<211> LENGTH: 21
<212> TYPE: DNA
<213> ORGANISM: Artificial Sequence
<220> FEATURE:
<223> OTHER INFORMATION: PCR primer

<400> SEQUENCE: 37
ggatgcactc gttgatgttt g                                             21

<210> SEQ ID NO 38
<211> LENGTH: 26
<212> TYPE: DNA
<213> ORGANISM: Artificial Sequence
<220> FEATURE:
<223> OTHER INFORMATION: probe for MON810
<220> FEATURE:
<221> NAME/KEY: modified_base
<222> LOCATION: (1)..(1)
<223> OTHER INFORMATION: Fam-a
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (26)..(26)
<223> OTHER INFORMATION: a-Tamra
<220> FEATURE:
<221> NAME/KEY: misc_feature
<222> LOCATION: (26)..(26)
<223> OTHER INFORMATION: n is a, c, g, or t

<400> SEQUENCE: 38
ngataccaag cggccatgga caacan                                        26

<210> SEQ ID NO 39
<211> LENGTH: 23
<212> TYPE: DNA
<213> ORGANISM: Artificial Sequence
<220> FEATURE:
<223> OTHER INFORMATION: PCR primer

<400> SEQUENCE: 39
caatgcgttc tccaccaagt act                                           23

<210> SEQ ID NO 40
<211> LENGTH: 20
<212> TYPE: DNA
<213> ORGANISM: Artificial Sequence
<220> FEATURE:
<223> OTHER INFORMATION: PCR primer

<400> SEQUENCE: 40
aaaagaccac aacaagccgc                                               20

<210> SEQ ID NO 41
<211> LENGTH: 27
<212> TYPE: DNA
```

```
<213> ORGANISM: Artificial Sequence
<220> FEATURE:
<223> OTHER INFORMATION: probe for Bt11
<220> FEATURE:
<221> NAME/KEY: modified_base
<222> LOCATION: (1)..(1)
<223> OTHER INFORMATION: Fam-c
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (27)..(27)
<223> OTHER INFORMATION: a-Tamra
<220> FEATURE:
<221> NAME/KEY: misc_feature
<222> LOCATION: (27)..(27)
<223> OTHER INFORMATION: n is a, c, g, or t

<400> SEQUENCE: 41
ngaccatgga caacaaccca aacatcn                                    27

<210> SEQ ID NO 42
<211> LENGTH: 20
<212> TYPE: DNA
<213> ORGANISM: Artificial Sequence
<220> FEATURE:
<223> OTHER INFORMATION: PCR primer

<400> SEQUENCE: 42
atccggttgg aaagcgactt                                            20

<210> SEQ ID NO 43
<211> LENGTH: 18
<212> TYPE: DNA
<213> ORGANISM: Artificial Sequence
<220> FEATURE:
<223> OTHER INFORMATION: PCR primer

<400> SEQUENCE: 43
gaagcctcgg caacgtca                                              18

<210> SEQ ID NO 44
<211> LENGTH: 20
<212> TYPE: DNA
<213> ORGANISM: Artificial Sequence
<220> FEATURE:
<223> OTHER INFORMATION: probe for GA21
<220> FEATURE:
<221> NAME/KEY: modified_base
<222> LOCATION: (1)..(1)
<223> OTHER INFORMATION: Fam-a
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (20)..(20)
<223> OTHER INFORMATION: g-Tamra
<220> FEATURE:
<221> NAME/KEY: misc_feature
<222> LOCATION: (20)..(20)
<223> OTHER INFORMATION: n is a, c, g, or t

<400> SEQUENCE: 44
naggatccgg tgcatggccn                                            20

<210> SEQ ID NO 45
<211> LENGTH: 19
```

```
<212> TYPE: DNA
<213> ORGANISM: Artificial Sequence
<220> FEATURE:
<223> OTHER INFORMATION: PCR primer

<400> SEQUENCE: 45
gccctctact ccaccccca                                                    19

<210> SEQ ID NO 46
<211> LENGTH: 20
<212> TYPE: DNA
<213> ORGANISM: Artificial Sequence
<220> FEATURE:
<223> OTHER INFORMATION: PCR primer

<400> SEQUENCE: 46
gcccatctgc aagccttttt                                                   20

<210> SEQ ID NO 47
<211> LENGTH: 26
<212> TYPE: DNA
<213> ORGANISM: Artificial Sequence
<220> FEATURE:
<223> OTHER INFORMATION: probe for soy 1e1
<220> FEATURE:
<221> NAME/KEY: modified_base
<222> LOCATION: (1)..(1)
<223> OTHER INFORMATION: Fam-a
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (26)..(26)
<223> OTHER INFORMATION: c-Tamra
<220> FEATURE:
<221> NAME/KEY: misc_feature
<222> LOCATION: (26)..(26)
<223> OTHER INFORMATION: n is a, c, g, or t

<400> SEQUENCE: 47
ngcttcgccg cttccttcaa cttcan                                            26

<210> SEQ ID NO 48
<211> LENGTH: 24
<212> TYPE: DNA
<213> ORGANISM: Artificial Sequence
<220> FEATURE:
<223> OTHER INFORMATION: PCR primer

<400> SEQUENCE: 48
cctttaggat ttcagcatca gtgg                                              24

<210> SEQ ID NO 49
<211> LENGTH: 18
<212> TYPE: DNA
<213> ORGANISM: Artificial Sequence
<220> FEATURE:
<223> OTHER INFORMATION: PCR primer

<400> SEQUENCE: 49
gacttgtcgc cgggaatg                                                     18

<210> SEQ ID NO 50
<211> LENGTH: 19
<212> TYPE: DNA
<213> ORGANISM: Artificial Sequence
<220> FEATURE:
```

<223> OTHER INFORMATION: probe for Roundup Reay Soy
<220> FEATURE:
<221> NAME/KEY: modified_base
<222> LOCATION: (1)..(1)
<223> OTHER INFORMATION: Fam-a
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (19)..(19)
<223> OTHER INFORMATION: c-Tamra
<220> FEATURE:
<221> NAME/KEY: misc_feature
<222> LOCATION: (19)..(19)
<223> OTHER INFORMATION: n is a, c, g, or t

<400> SEQUENCE: 50
ngcaaccgcc cgcaaatcn                                            19

<210> SEQ ID NO 51
<211> LENGTH: 27
<212> TYPE: DNA
<213> ORGANISM: Artificial Sequence
<220> FEATURE:
<223> OTHER INFORMATION: PCR primer

<400> SEQUENCE: 51
catttggaga ggtcgatttc tctcttg                                   27

<210> SEQ ID NO 52
<211> LENGTH: 27
<212> TYPE: DNA
<213> ORGANISM: Artificial Sequence
<220> FEATURE:
<223> OTHER INFORMATION: PCR primer

<400> SEQUENCE: 52
gagagaaatc gacctctcca aatgaaa                                   27

<210> SEQ ID NO 53
<211> LENGTH: 35
<212> TYPE: DNA
<213> ORGANISM: Artificial Sequence
<220> FEATURE:
<223> OTHER INFORMATION: PCR primer

<400> SEQUENCE: 53
tatcacatca atgcccgggc gaatcctgtt gccgg                          35

<210> SEQ ID NO 54
<211> LENGTH: 36
<212> TYPE: DNA
<213> ORGANISM: Artificial Sequence
<220> FEATURE:
<223> OTHER INFORMATION: PCR primer

<400> SEQUENCE: 54
ggcaacagga ttcgcccggg cattgatgtg atatct                         36

<210> SEQ ID NO 55
<211> LENGTH: 27
<212> TYPE: DNA
<213> ORGANISM: Artificial Sequence
<220> FEATURE:
<223> OTHER INFORMATION: PCR primer

<400> SEQUENCE: 55
aaactaggat aaatcgcaag accggca                      27

<210> SEQ ID NO 56
<211> LENGTH: 27
<212> TYPE: DNA
<213> ORGANISM: Artificial Sequence
<220> FEATURE:
<223> OTHER INFORMATION: PCR primer

<400> SEQUENCE: 56
tcggggaagc tctgagcgaa accctat                      27

<210> SEQ ID NO 57
<211> LENGTH: 27
<212> TYPE: DNA
<213> ORGANISM: Artificial Sequence
<220> FEATURE:
<223> OTHER INFORMATION: PCR primer

<400> SEQUENCE: 57
ggcctaactg gcggatgcac tcgttga                      27

<210> SEQ ID NO 58
<211> LENGTH: 27
<212> TYPE: DNA
<213> ORGANISM: Artificial Sequence
<220> FEATURE:
<223> OTHER INFORMATION: PCR primer

<400> SEQUENCE: 58
acgagtgcat ccgccagtta ggccagt                      27

<210> SEQ ID NO 59
<211> LENGTH: 27
<212> TYPE: DNA
<213> ORGANISM: Artificial Sequence
<220> FEATURE:
<223> OTHER INFORMATION: PCR primer

<400> SEQUENCE: 59
ggagaaggca tcgactgact actccac                      27

<210> SEQ ID NO 60
<211> LENGTH: 27
<212> TYPE: DNA
<213> ORGANISM: Artificial Sequence
<220> FEATURE:
<223> OTHER INFORMATION: PCR primer

<400> SEQUENCE: 60
gagtagtcag tcgatgcctt ctcccta                      27

<210> SEQ ID NO 61
<211> LENGTH: 27
<212> TYPE: DNA
<213> ORGANISM: Artificial Sequence
<220> FEATURE:
<223> OTHER INFORMATION: PCR primer

<400> SEQUENCE: 61
tgctggtgaa cacggcaaca ggattca                      27

<210> SEQ ID NO 62
<211> LENGTH: 27
<212> TYPE: DNA

<213> ORGANISM: Artificial Sequence
<220> FEATURE:
<223> OTHER INFORMATION: PCR primer

<400> SEQUENCE: 62
atcctgttgc cgtgttcacc agcagca                27

<210> SEQ ID NO 63
<211> LENGTH: 27
<212> TYPE: DNA
<213> ORGANISM: Artificial Sequence
<220> FEATURE:
<223> OTHER INFORMATION: PCR primer

<400> SEQUENCE: 63
cggcgacaag tcgcccatct gcaagcc                27

<210> SEQ ID NO 64
<211> LENGTH: 27
<212> TYPE: DNA
<213> ORGANISM: Artificial Sequence
<220> FEATURE:
<223> OTHER INFORMATION: PCR primer

<400> SEQUENCE: 64
ttgcagatgg gcgacttgtc gccggga                27

<210> SEQ ID NO 65
<211> LENGTH: 27
<212> TYPE: DNA
<213> ORGANISM: Artificial Sequence
<220> FEATURE:
<223> OTHER INFORMATION: PCR primer

<400> SEQUENCE: 65
aaactaggat aaatccggtt ggaaagc                27

<210> SEQ ID NO 66
<211> LENGTH: 27
<212> TYPE: DNA
<213> ORGANISM: Artificial Sequence
<220> FEATURE:
<223> OTHER INFORMATION: PCR primer

<400> SEQUENCE: 66
ttccaaccgg atttatccta gtttgcg                27

<210> SEQ ID NO 67
<211> LENGTH: 27
<212> TYPE: DNA
<213> ORGANISM: Artificial Sequence
<220> FEATURE:
<223> OTHER INFORMATION: PCR primer

<400> SEQUENCE: 67
tgccgaggct tctgagcgaa accctat                27

<210> SEQ ID NO 68
<211> LENGTH: 27
<212> TYPE: DNA
<213> ORGANISM: Artificial Sequence
<220> FEATURE:
<223> OTHER INFORMATION: PCR primer

<400> SEQUENCE: 68
gggtttcgct cagaagcctc ggcaacg                27

<210> SEQ ID NO 69
<211> LENGTH: 27
<212> TYPE: DNA
<213> ORGANISM: Artificial Sequence
<220> FEATURE:
<223> OTHER INFORMATION: PCR primer

<400> SEQUENCE: 69
tgctggtgaa catcaatgcg ttctcca                                27

<210> SEQ ID NO 70
<211> LENGTH: 27
<212> TYPE: DNA
<213> ORGANISM: Artificial Sequence
<220> FEATURE:
<223> OTHER INFORMATION: PCR primer

<400> SEQUENCE: 70
agaacgcatt gatgttcacc agcagca                                27

<210> SEQ ID NO 71
<211> LENGTH: 27
<212> TYPE: DNA
<213> ORGANISM: Artificial Sequence
<220> FEATURE:
<223> OTHER INFORMATION: PCR primer

<400> SEQUENCE: 71
ggagtagagg gcttatccta gtttgcg                                27

<210> SEQ ID NO 72
<211> LENGTH: 27
<212> TYPE: DNA
<213> ORGANISM: Artificial Sequence
<220> FEATURE:
<223> OTHER INFORMATION: PCR primer

<400> SEQUENCE: 72
aaactaggat aagccctcta ctccacc                                27

<210> SEQ ID NO 73
<211> LENGTH: 1102
<212> TYPE: DNA
<213> ORGANISM: Artificial Sequence
<220> FEATURE:
<223> OTHER INFORMATION: amplification region of the standard molecule
      for quantitative detection of maize transformants

<400> SEQUENCE: 73
ctcccaatcc tttgacatct gctccgaagc aaagtcagag cgctgcaatg caaaacggaa      60
cgagtggggg cagcagcgcg agcaccgccg cgccggtgtc cggacccaaa gctgatcatc     120
catcagctcc tgtcaccaag agagaaatcg acctctccaa atgaaatgaa cttccttata     180
tagaggaagg gtcttgcgaa ggatagtggg attgtgcgtc atcccttacg tcagtggaga     240
tatcacatca atgcccgggc gaatcctgtt gccggtcttg cgatgattat catataattt     300
ctgttgaatt acgttaagca tgtaataatt aacatgtaat gcatgacgtt atttatgaga     360 tgggtttta tgattagagt cccgcaatta tacatttaat acgcgataga aaacaaaata     420
tagcgcgcaa actaggataa atcgcaagac cggcaacagg attcaatctt aagaaacttt     480
attgccaaat gtttgaacga tcggggaaat tcgtcgaagc ttcttctaga gcttaattct     540
tgacgaaagt gctcagcaca tcgaagtagt cggggaaggt ctgagcgaaa ccctataaga     600

```
accctaattc ccttatctgg gaactactca cacattatta tagagagaga tagatttgta    660
gagagagact ggtgatttca gcgggcatgc ctgcaggtcg actcagatct gggtaactgg    720
cctaactggc ggatgcactc gttgatgttt gggttgttgt ccatggccgc ttggtatctg    780
cattacaatg aaatgagcaa agactatgtg agtaacactg gtcaacacta gggagaaggc    840
atcgactgac tactccactt tgtgcagaac agatctagag ctcctacacc tgatcgatgt    900
ggtagtcggt cacgtcggtc ttcaggccga tctggttgct gctggtgaac acggcaacag    960
gattcaatct taagaaactt tattgccaaa tgtttgaacg atcctgatct tcagtactca   1020
gcctcgaagg taacttcggc aggcacaaac tcaatacggt caatgtacac ttcattgcca   1080
gaattgaaca catgagcgct aa                                             1102
```

```
<210> SEQ ID NO 74
<211> LENGTH: 1071
<212> TYPE: DNA
<213> ORGANISM: Artificial Sequence
<220> FEATURE:
<223> OTHER INFORMATION: amplification region of the standard molecule
      for quantative detection of maize transformants

<400> SEQUENCE: 74
ctcccaatcc tttgacatct gctccgaagc aaagtcagag cgctgcaatg caaaacggaa     60
cgagtggggg cagcagcgcg agcaccgccg cgccggtgtc cggacccaaa gctgatcatc    120
catcagctcc tgtcaccaag agagaaatcg acctctccaa atgaaatgaa cttccttata    180
tagaggaagg gtcttgcgaa ggatagtggg attgtgcgtc atcccttacg tcagtggaga    240
tatcacatca atgcccgggc gaatcctgtt gccggtcttg cgatgattat catataattt    300
ctgttgaatt acgttaagca tgtaataatt aacatgtaat gcatgacgtt atttatgaga    360
tgggttttta tgattagagt cccgcaatta tacatttaat acgcgataga aaacaaaata    420
tagcgcgcaa actaggataa atccggttgg aaagcgactt ggaccccggc agcttgacgg    480
tgccggagat ctccttgatg ggctgcagca cgatctcctc ggcgccggcc atgcaccgga    540
tccttccgcc gttgctgacg ttgccgaggc ttctgagcga aaccctataa gaaccctaat    600
tcccttatct gggaactact cacacattat tatagagaga gatagatttg tagagagaga    660
ctggtgattt cagcgggcat gcctgcaggt cgactcagat ctgggtaact ggcctaactg    720
gcggatgcac tcgttgatgt ttgggttgtt gtccatggcc gcttggtatc tgcattacaa    780
tgaaatgagc aaagactatg tgagtaacac tggtcaacac tagggagaag gcatcgactg    840
actactccac tttgtgcaga acagatctag agctcctaca cctgatcgat gtggtagtcg    900
gtcacgtcgg tcttcaggcc gatctggttg ctgctggtga acatcaatgc gttctccacc    960
aagtacttca acttctgggt tactcaagca gttgtatgga atgcattcgt tgatgtttgg   1020
gttgttgtcc atggtcgact ctagaggatc cgcggcttgt tgtggtcttt t            1071
```

```
<210> SEQ ID NO 75
<211> LENGTH: 239
<212> TYPE: DNA
<213> ORGANISM: Artificial Sequence
<220> FEATURE:
<223> OTHER INFORMATION: amplification region of the standard molecule
      for quantitative detection of soy transformants

<400> SEQUENCE: 75
cctttaggat ttcagcatca gtggctacag cctgcatgct tcacggtgca agcagccggc     60
```

-continued

```
ccgcaaccgc cgcaaatcc tctggccttt ccggaaccgt ccgcattccc ggcgacaagt    120
cgcccatctg caagccttt tgtgtcaggg gcatagaagg tgaagttgaa ggaagcggcg    180
aagctggcaa cgctaccggt ttctttgtcc caaatgtgga tgggggtgga gtagagggc    239
```

<210> SEQ ID NO 76
<211> LENGTH: 528
<212> TYPE: DNA
<213> ORGANISM: Artificial Sequence
<220> FEATURE:
<223> OTHER INFORMATION: amplification region of the standard molecule
      for quantitative detection of soy transformants

<400> SEQUENCE: 76

```
cctttaggat ttcagcatca gtggctacag cctgcatgct tcacggtgca agcagccggc    60
ccgcaaccgc cgcaaatcc tctggccttt ccggaaccgt ccgcattccc ggcgacaagt    120
cgcccatctg caagccttt tgtgtcaggg gcatagaagg tgaagttgaa ggaagcggcg    180
aagctggcaa cgctaccggt ttctttgtcc caaatgtgga tgggggtgga gtagagggct    240
tatcctagtt tgcgcgctat attttgtttt ctatcgcgta ttaaatgtat aattgcggga    300
ctctaatcat aaaaacccat ctcataaata acgtcatgca ttacatgtta attattacat    360
gcttaacgta attcaacaga aattatatga taatcatcgc aagaccggca acaggattcg    420
cccgggcatt gatgtgatat ctccactgac gtaagggatg acgcacaatc ccactatcct    480
tcgcaagacc cttcctctat ataaggaagt tcatttcatt tggagagg                528
```

<210> SEQ ID NO 77
<211> LENGTH: 22
<212> TYPE: DNA
<213> ORGANISM: Artificial Sequence
<220> FEATURE:
<223> OTHER INFORMATION: PCR primer

<400> SEQUENCE: 77

```
tcccaatcct ttgacatctg ct                                             22
```

<210> SEQ ID NO 78
<211> LENGTH: 23
<212> TYPE: DNA
<213> ORGANISM: Artificial Sequence
<220> FEATURE:
<223> OTHER INFORMATION: PCR primer

<400> SEQUENCE: 78

```
gacaggagct gatggatgat cag                                            23
```

<210> SEQ ID NO 79
<211> LENGTH: 22
<212> TYPE: DNA
<213> ORGANISM: Artificial Sequence
<220> FEATURE:
<223> OTHER INFORMATION: PCR primer

<400> SEQUENCE: 79

```
ccaatccttt gacatctgct cc                                             22
```

<210> SEQ ID NO 80
<211> LENGTH: 19
<212> TYPE: DNA
<213> ORGANISM: Artificial Sequence
<220> FEATURE:
<223> OTHER INFORMATION: PCR primer

```
<400> SEQUENCE: 80
gatcagcttt gggtccgga                                                    19
```

METHODS OF QUANTITATIVE DETECTION OF GENETIC RECOMBINANTS AND STANDARD MOLECULES FOR THE METHODS

CROSS-REFERENCE TO RELATED APPLICATION

The present application is a continuation of International Application No. PCT/JP01/09344, which designates the U.S., filed on Oct. 24, 2001, and which claims priority to Japanese Application No. 2000-326738, filed on Oct. 26, 2000.

TECHNICAL FIELD OF THE INVENTION

The present invention relates to a method of detecting a genetic recombinant by using PCR (polymerase chain reaction). Particularly, the present invention relates to a molecular biological method of detecting a DNA sequence which is specific to a genetic recombinant using PCR. More specifically, the present invention relates to a method of detecting the content ratio of each genetic recombinant line which may be exist in a population containing various genetic recombinants harboring various recombinant DNA sequences. Furthermore, the present invention relates to a standard molecule which is used in such a molecular biological method of detecting the genetic recombinant.

BACKGROUND OF THE INVENTION

The worldwide practical use of genetic recombinants, which are produced by using genetic recombinant techniques, is in progress. As the genetic recombinants which have been already practically used, genetic recombinant microorganisms such as those represented by interferon producing bacteria and genetic recombinant crops such as those represented by insect-resistant maize have been known. For example, an insect-resistant gene such as the CryIA(b) protein coding region (herein after, cryIA(b)) from *Bacillus thuringiensis* or herbicide-resistant gene such as phosphinotricin acetyl transferase(PAT) protein coding region (hereinafter, pat) has been used in the previously developed genetic recombinant crops. In such cases, these transgenes were introduced as the expression units combined with various DNA sequences such that the transgenes can express in the crops.

The DNA sequences which can be used include 35S promoter from cauliflower mosaic virus (hereinafter, CaMV35S promoter), the promoter of phosphoenolpyruvate carboxykinase (PEPC) gene from maize, the promoter of calcium dependent protein kinase (CDPK) from maize, the introns such as the region containing the sixth intron of alcohol dehydrogenase 1S gene from maize (Adh1-S IVS6), the region containing the second intron of alcohol dehydrogenase 1S gene from maize (Adh1-S IVS2), the 9th intron of PEPC (PEPC#9) or the intron region of heat-shock protein 70 (hsp70) from maize, and the terminators such as nopaline synthase terminator (herein after, NOS terminator) from *Agrobacterium tumefaciens* or 35S terminator from cauliflower mosaic virus. The actually commercially distributed genetic recombinant crops include, for example, the progeny varieties from Bt11 line of Novartis, the progeny varieties from Event 176 of Novartis, the progeny varieties from MON810 line of Monsanto, the progeny varieties from GA21 line of Monsanto and the progeny varieties from T25 line of Aventis, for maize. For soybean, they include, for example, progeny varieties from Roundup Ready Soy line. The constructions of DNAs that had been introduced into these varieties are shown in FIG. 1.

Generally, a genetic recombinant has been developed to impart an industrially preferable property to an original organism compared with the original organism. The major approach for such purpose is isolating a gene expressing the property from an organism which intrinsically exhibits the property, and introducing the gene into the interested organism such that the gene can be expressed in the organism. Thus, the DNAs from genetic recombinants include such recombinant DNA sequences which have been introduced into the recombinants.

For example, genetic recombinant crops have been developed to impart them preferable properties as agricultural products, such as insect-resistance as well as herbicide-resistance and the like, and which crops are produced by introducing the gene responsible for insect-resistance or herbicide-resistance and the like into the original crops, in the form where the gene can be expressed in the crops. Thus, the DNAs from genetic recombinants include such recombinant DNA sequences that have been introduced into the recombinants.

However, when such crops are actually commercialized, it is likely that the crops are the progeny hybrids of the genetic recombinant crops. Therefore, it should be confirmed that the introduced DNA sequences stably exist in such crops.

Additionally, European Community (EU) has enacted the regulation affecting the labeling of genetic recombinants and processed foods produced from them (Regulation (EC) No. EC/258/97, Council Regulation (EC) No. 1139/98), and the regulation affecting the labeling of genetic recombinants and processed foods produced from them was also issued in Japan, which arose the need in the food industry and its relating filed for the information about the existence and the content of recombinants in crops or in foods.

Thus, there is a need for a technique which allows the determination of the existence of genetic recombinants or the content thereof in foods, feeds and in the source crops thereof, particularly the content ratio thereof in the raw materials. When plural genetic recombinant lines are expected to be contained, a techniques is desired which makes it possible to detect them individually and to define the content ratio of each line, that is, the development of a practical technique having high sensitivity and quantitativity to detect the individual line of genetic recombinants is desired.

Although there are many reports showing that it is advantageous to use the molecular biological techniques using polymerase chain reaction (PCR) (Science Vol. 230, 1350-1354 (1985), Science Vol. 239, 487-491 (1988)) for detecting genetic recombinants, these techniques qualitatively determine whether the genetic recombinants exist or not and they do not generate the information about the content ratio of the genetic recombinants contained in the samples (see, for example, Z. Lebensm Unters Forsch A., Vol.203, 339-344 (1996), Mitt. Gebiete Lebensm. Hyg., Vol.87, 307-367 (1996), Deutsche Lebensmittel-Rundschau, Vol.93, Jahrg., Heft 2, 35-38 (1997), Z. Lebensm Unters Forsch A., Vol.205, 442-445 (1997), Zeitschrift fur Ernahrungwissenscaft Vol.36, 155-160 (1997), BGVV Hefte 1, 115-117 (1997), Mitt. Gebiete Lebensm. Hyg., Vol.88, 164-175 (1997), Mitt. Gebiete Lebensm. Hyg., Vol.88, 515-524 (1997), Food Additives and Contaminants, Vol.15, No.7, 767-774 (1998), Lebensm.—Wiss. u.—Technol., Vol.31, 664-667 (1998), Z. Lebensm Unters Forsch A., Vol.206, 203-207 (1998), Z. Lebensm Unters Forsch A., Vol.206, 237-242 (1998), Z. Lebensm Unters Forsch A., Vol.207, 264-267 (1998), BioSci. Biotecnol. Biochem. Vol.62, No.7, 1461-1464 (1998), Deutsche Lebensmittel-Rundschau, Vol.95, Jahrg., Heft 2, 44-48 (1999), Deutsche Lebensmittel-Rundschau, Vol.95, Jahrg., Heft 2, 48-51 (1999), Deutsche Lebensmittel-Rundschau, Vol.95, Jahrg., Heft 2, 52-56 (1999), Deutsche Lebensmittel-Rundschau, Vol.95, Jahrg., Heft 7, 275-278 (1999), Journal of AOAC International Vol.82, No.4, 923-928 (1999), GIT Labor-Fachzetschrift, 2/99, 156-160 (1999), Bio Industry Vol.16, No.4, 17-21 (1999), Eur. Food Res. Technol. Vol.209, 77-82 (1999), Analytica Chimica Acta Vol.393, 177-179 (1999), Food Control Vol.10, 339-349 (1999), Journal of Agricultural and Food Chemistry, Vol.47, No.12, 5038-5043 (1999), Journal of Food Hygienic Society of Japan, Vol.41, No.2, 137-143 (2000)).

There are also several reports for known techniques that can provide the information of the content ratio of each genetic recombinant contained in the sample such as the reports for techniques for quantitatively determining the recombinant DNA sequences form soybean and maize.

For example, Deutsche Lebensmittel-Rundschau, Vol.95, Jahrg., Heft 2, 57-59 (1999) and Eur. Food. Res. Technol, Vol.209, 83-87 (1999) reports the quantitative detecting techniques for soybean using competitive PCR. These techniques, however, were limited to only a single line of genetic recombinant soybean. Moreover, the accuracy of quantification was relatively low due to the use of competitive PCR and, the purity and yield of the DNA solution extracted from samples affected the result of quantification because they do not use an internal standard.

The quantitative detection technique for genetic recombinant maize using competitive PCR was also reported in Z. Lebensm Unters Forsch A, Vol.207, No.3, 207-213 (1998), but the target of the detection was also limited to only a single line of genetic recombinant maize, which is similar to the above-mentioned case. Furthermore, similarly to the above-described case, the competitive PCR and the lack of internal standard made the reliability of the result of quantification insufficient.

Food Control Vol.10, 353-358 (1999) reports a quantitative detection technique using competitive PCR for genetic recombinant maize and genetic recombinant soybean, but both techniques were limited to only a single line, respectively. Furthermore, the use of competitive PCR and the lack of an internal standard made the reliability of the result of quantification insufficient, as above described.

Quantitative PCR using a fluorescent probe and the like (also referred to as real time PCR or in line PCR etc.) is known as a quantitative analysis which is superior to competitive PCR in the accuracy of quantification. There are several reports regarding the quantitative detection techniques using quantitative PCR for recombinant DNA sequences.

For example, Journal of Agricultural and Food Chemistry, Vol.47, No.12, 5261-5266 (1999) reports that the quantification of recombinant soybean and maize can be performed by quantitative PCR with fluorescent probes. In this reports, the internal standard procedure was employed, which improved the reliability of the quantification result. The target of detection, however, was a single line for genetic recombinant soybean and also a single line for genetic recombinant maize.

Food Control Vol.10, 385-389 (1999) also reports two techniques, the quantitative detection techniques for genetic recombinant soybean using quantitative PCR with fluorescent probes and the quantitative detection techniques for genetic recombinant soybean using competitive PCR. The internal standard procedures were also used in these reports, which improved the reliability of the result of quantification. In contrast to the above-referred reports, the plasmid DNA containing a DNA sequence for internal standard and the plasmid DNA containing the target DNA sequence to be examined were used as a standard molecule. However, since both plasmids were provided separately, there remained the possibility that the manner of diluting the plasmid DNA and the amount of plasmid DNA added into the reaction system affected the result of quantification. Again the target of detection was limited to a single line of genetic recombinant soybean. Chemie in Labor und Biotechnik. Vol.50, Jahrg., Heft 1, 6-8 (1999) is similar to the above-mentioned reports.

Furthermore, since the genetic recombinants that are commercially available as the standard materials are only two lines for maize and one line for soybean, it is very difficult for the analysts to analyze other lines.

A technique for quantifying the content of genetic recombinants was also reported where the protein expressed from a the recombinant DNA sequence is determined by Enzyme Linked Immunosorbent Assay (ELISA), but this technique was also the technique of quantitative quantification for a particular single line.

SUMMARY OF THE INVENTION

As above described, the previously reported quantitative detection techniques for genetic recombinants are those which quantitatively detect only limited lines or those which lack the accuracy in quantification.

On the other hand, it is very difficult to quantitatively examine the content ratio of genetic recombinants in a sample when the techniques for detecting only particular one of such lines, because the crops which are conventionally distributed are in the sate where various varieties are mixed during the distribution process. For example, the genetic recombinant maize lines distributed in Japan are up to 7 lines as of July, 2000. Therefore, the analysis would be insufficient if only a particular single line of genetic recombinant maize in the sample is quantitatively determined. Thus, it is understand that it should be noticed that the technique for detecting only a particular single line as well as the technique lacking the accuracy of quantification is insufficient as a quantitative analysis method and lacks the actual utility.

One of the factors limiting the number of the target lines to be detected is the insufficient supply of the assay standards. It is very difficult to obtain a pure standard sample which contains only a particular single line of genetic recombinants and which does not contain any other lines. The currently provided genetic recombinants as standard samples for conventional analysts are only two lines for maize and one line for soybean. Indeed, in the previously mentioned prior reports regarding the quantitative detection techniques, all the targets were limited to those for which the respective standard samples can be available (This is also mentioned in the previously referred reference, for example, in Food Control Vol.10, 385-389 (1999)). Namely, the availability of the standard samples leads to the result that the applicability of the above-mentioned detection techniques is limited.

Additionally, since the type and copy number of the introduced recombinant DNA sequence per genome in each line of the genetic recombinants differ among the lines, if the analysis is carried out assuming that only particular line(s) is/are contained in the sample without considering the effects of such differences, it is likely to obtain the results far from the actual content ratio of the genetic recombinants. Thus, even if all the genetic recombinants lines are provided as the standard samples for the analysis, these techniques could not be considered as actual quantitative detection techniques for genetic recombinants unless any means are figured out to take the diversity of recombinant DNA sequences among lines into account.

As mentioned above, it is desired to develop a sensitive and quantitative practical detection technique for genetic recombinants and the development thereof has been actively attempted, but the development and popularization of molecular biological detection techniques for recombinant DNA sequences and/or genetic recombinants are difficult due to the conventional distribution manners, the availability of the standard samples and the diversity of the recombinant DNA sequences among lines.

Accordingly, the object of the present invention is to provide a molecular biological method of detecting genetic recombinants, wherein the accurate total content ratio of genetic recombinants in a population containing plural lines of genetic recombinants can be quantitatively determined by strictly taking the diversity of the recombinant DNA sequences among the plural genetic recombinant lines into account.

Particularly, the object of the present invention is to provide a molecular biological method of detecting genetic recombinants, wherein the accurate individual content ratio of each of the genetic recombinant in a population containing plural lines of genetic recombinants can be quantitatively determined by strictly taking the diversity of the recombinant DNA sequences among the plural genetic recombinant lines into account.

Another object of the present invention is to provide a recombinant DNA molecule as a standard sample used for the above-mentioned quantitative detection method, which especially has the property of being able to be unlimitedly supplied, wherein the molecule is designed so that the quantification can be performed by strictly taking the diversity of the recombinant DNA sequences among the plural genetic recombinant lines into account.

The inventors of the present invention produced a molecule containing, on a single molecule, five genetic recombinant maize line specific DNA sequences, two DNA sequences which are frequently used for the genetic recombinants but are not line-specific and additional one DNA sequence of endogenous maize gene, a molecule containing, on a single molecule, one genetic recombinant soybean line specific DNA sequence and one DNA sequence of endogenous soybean gene and a molecule containing, on a single molecule, one genetic recombinant soybean line specific DNA sequence, one DNA sequence of endogenous soybean gene and two DNA sequences which are frequently used for the genetic recombinants but are not line-specific and found that the previous qualitative and quantitative detection methods can be remarkably improved by using these molecules as the standard molecules in PCR, which allow the inventors to establish the present invention.

Accordingly, the present invention is a quantitative detection method for quantitatively determining a content ratio of a genetic recombinant in a sample containing at least one genetic recombinant lines, which comprises: (i) performing quantitative PCR for a DNA sequence specific to the genetic recombinant(s) which may exist in a DNA sample derived from genetic recombinants in the sample and quantitative PCR for an endogenous DNA sequence shared by the species corresponding to the genetic recombinant using, as a standard molecule, a molecule containing, on a single molecule, the DNA sequence specific to the genetic recombinant and the endogenous DNA sequence; (ii) determining the number of the DNA sequence specific to the genetic recombinant(s) in the sample based on the result of the quantitative PCR; (iii) determining the number of the endogenous DNA sequence in the sample based on the result of the quantitative PCR; and (iv) determining the content ratio of the genetic recombinant(s) according to formula (I):

(content ratio of the genetic recombinant(s) in the sample)=100×[(the number of molecules of the DNA sequence specific to the genetic recombinant(s) in the sample)/(the number of molecules of the endogenous DNA sequence in the sample)]/(quantification ratio)(%)   (I)

wherein the quantification ratio is any of the values which is pre-calculated according to formula (II):

(quantification ratio)(%)=(the number of molecules of the DNA sequence specific to a genetic recombinant from the individual genetic recombinant line)/(the number of molecules of the endogenous DNA sequence in the genetic recombinant)   (II).

More specifically, the present invention is a quantitative detection method for quantitatively determining an individual content ratio of an individual genetic recombinant line in a sample containing at lest one genetic recombinant line, which comprises: (i) performing quantitative PCR for a DNA sequence specific to the individual genetic recombinant line which may exist in a DNA sample derived from genetic recombinants in the sample and quantitative PCR for an endogenous DNA sequence shared by the species corresponding to the genetic recombinants using, as a standard molecule, a molecule containing, on a single molecule, the DNA sequence specific to the individual genetic recombinant line and the endogenous DNA sequence; (ii) determining the number of the DNA sequence specific to the individual genetic recombinant line in the sample based on the result of said quantitative PCR; (iii) determining the number of the endogenous DNA sequence in the sample based on the result of the quantitative PCR; and (iv) determining content ratio of the genetic recombinant according to formula (III):

(content ratio of the individual genetic recombinant line in the sample)=100×[(the number of molecules or the DNA sequence corresponding to each genetic recombinant in the sample)/(the number of molecules of the endogenous DNA sequence in the sample)]/(quantification ratio)(%)   (III)

wherein the quantification ratio is calculated according to the above-identified formula (II).

The recombinant DNA molecule of the present invention is the recombinant DNA molecule characterized in that it contains, on a single molecule, a DNA sequence specific to the line(s) of genetic recombinant and at least one endogenous DNA sequence shared by the species corresponding to the genetic recombinants. Particularly, the DNA molecule of the present invention is the recombinant DNA molecule characterized in that it contains, on a single molecule, two or more DNA sequences specific to the individual line of genetic recombinants respectively, and at least one endogenous DNA sequence shared by two or more non-transformants corresponding to said genetic recombinants.

BRIEF DESCRIPTION OF DRAWINGS

FIG. 1 shows the construction of the recombinant DNA sequence introduced into each genetic recombinant line and the location of the designed primers for the molecular biological analysis, respectively. Each primer pair for amplifying the DNA sequence specific to each genetic recombinant line was designed so that it can amplify the region extending over the plural DNA sequences. The primer pair for amplifying the DNA sequence which is not line-specific but which is frequently used for genetic recombinants was designed so that it can be reacted with all of the corresponding lines.

FIG. 2 shows the result of specificity verification test using the primer pair designed for detecting T25 line progeny variety. The amplification reaction was not observed for the DNA extracted from the samples other than those from T25 line progeny varieties and the amplified product was observed only with the DNA extracted from the progeny varieties from T25 line. The molecular weight of the amplified product was consistent with the designed one.

FIG. 5 shows the nucleotide sequence of the standard molecule for maize (SEQ ID No:73). The locations of each amplification target in the combined DNA sequences were shown in the figure. The binding regions of the primers and probe used in the experiment were also shown in the figure.

FIG. 6 shows the nucleotide sequence of another standard molecule for maize (SEQ ID No:74). The locations of the combined DNA sequences for each amplification target were shown in the figure. The binding regions of the primers and the probe used in the experiment were also shown in the figure.

FIG. 8 shows the nucleotide sequence of the standard molecule for soybean (SEQ ID No:75). The locations of each target of amplification in the combined DNA sequences were shown in the figure. The binding regions of the primers and the probe used in the experiment were also shown in the figure.

FIG. 9 shows the nucleotide sequence of the standard molecule for soybean (SEQ ID No:76). The locations of each target of amplification in the combined DNA sequences were shown in the figure. The binding regions of the primers and probe used in the experiment were also shown in the figure.

FIG. 12 confirmed the genetic recombinant maize contained in the blind maize sample. The progeny varieties from Bt11 line (A) and the progeny varieties form GA21 line and MON810 line (B) were detected. BamHI digest of pMul4 was used as a control.

FIGS. 14A and 14B show the graph of (cycles—fluorescence intensity) during the quantitative PCR for maize standard recombinant DNA sequence.

FIGS. 15A and 15B show the standard curve obtained by the quantitative PCR for maize standard recombinant DNA sequence. The standard curve was derived in FIGS. 15A and 15B were derived from FIGS. 14A and 14B, respectively.

PREFERRED EMBODIMENTS OF THE INVENTION

Figure 3:
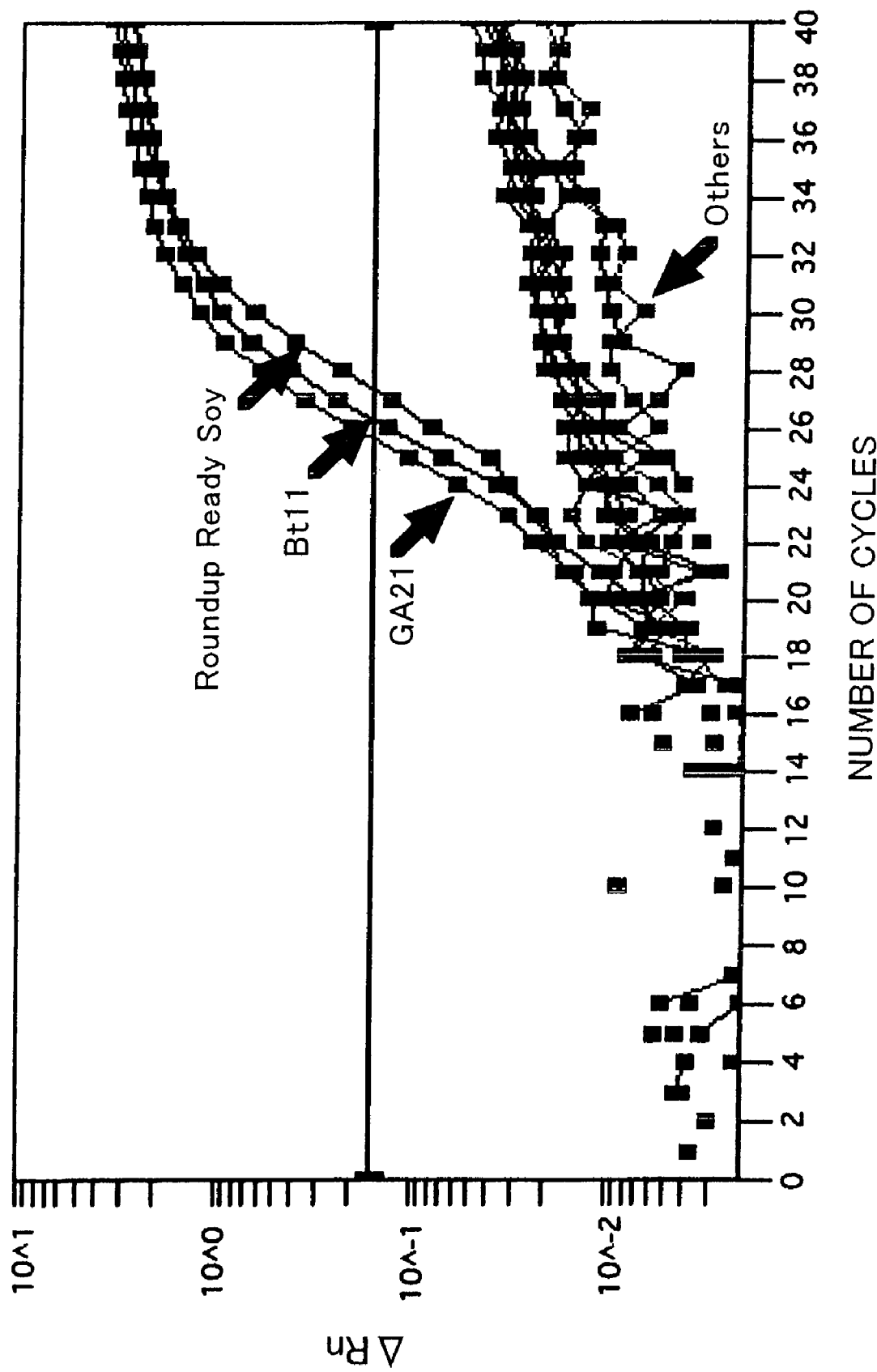
FIG. 3 shows the result of specificity verification test using the primer pair and the probe designed for detecting NOS terminator. The experiments were performed with 11 DNA templates. As can be seen in FIG. 1, NOS terminator is introduced into the progeny varieties from Bt11 line, the progeny varieties from GA21 line and the progeny varieties from Roundup Ready Soy line. The experimental results showed that the amplified products were observed only with the template DNAs extracted from these three varieties and were not observed when other template DNAs were subjected to the reaction, which confirmed the designed specificity.

The present invention will be illustrated in the following description by genetic recombinant crops as the example of genetic recombinants, but the application of the present invention are not limited to crops and the present invention does not exclude other genetic recombinants including genetic recombinant animals, plants, microorganisms and the like. In one embodiments of the present invention, recombinant DNA sequences are detected by using PCR method with nucleic acids from test plants to specifically detect various genetic recombinants. Accordingly, it is required to design the primer pair to detect the DNA sequence which is specific to the genetic recombinant line, the primer pair to detect a DNA sequence which is not line-specific but is frequently used for genetic recombinants and the primer pair to detect a DNA sequence which is specific to the crops which may be either a genetic recombinant or a non-recombinant.

The test plant samples may be any samples from which the nucleic acids such as genome DNA can be extracted, including raw seeds, dry seeds, processed materials such as corn grits and soybean flour. Such samples can be used after grinding, if necessary.

According to the present invention, it is possible to determine the content ratio of the genetic recombinants, especially the content ratio of the individual genetic recombinant, in the sample which may possibly contains one or two or more genetic recombinant lines, based on the number of molecules of the recombinant DNA sequences, the number of molecules of the endogenous gene and the quantification ratio calculated for the individual genetic recombinant in the sample.

According to the present invention, content ratio of a genetic recombinant is calculated by the following procedure: (i) performing quantitative PCR using a molecule as a standard molecule, which contains, on a single molecule, a DNA sequence specific to the genetic recombinant(s) which may exist in a sample and an endogenous DNA sequence shared by the species corresponding to the genetic recombinant; (ii) determining the number of the DNA sequence specific to the genetic recombinant(s) in the sample based on the result of the quantitative PCR; (iii) determining the number of the endogenous DNA sequence in the sample based on the result of the quantitative PCR; and (iv) determining the content ratio of the genetic recombinant(s) according to formula (I):

(content ratio of the genetic recombinant(s) in the sample)=100×[(the number of molecules of the DNA sequence specific to the genetic recombinant(s) in the sample)/(the number of molecules of the endogenous DNA sequences in the sample)]/(quantification ratio)(%)   (I)

wherein the quantification ratio is any of the values which is pre-calculated according to the formula (II):

(quantification ratio)(%)=(the number of molecules of the DNA sequence specific to a genetic recombinant from the individual genetic recombinant line)/(the number of molecules of the endogenous DNA sequence in the genetic recombinant)     (II).

Particularly, when the individual content ratio of each genetic recombinant is determined, formula (III) will be used instead of formula (I):

(content ratio of the individual genetic recombinant line in the sample)=100×[(the number of molecules of the DNA sequence specific to the individual genetic recombinant in the sample)/(the number of molecules of the endogenous DNA sequence in the sample)]/(quantification ratio) (%)     (III)

The term "DNA sequence" and "DNA sequence or the partial region thereof" as used herein are used interchangeably. Thus, for example, "DNA sequence specific to a genetic recombinant line" means a full length DNA or at least one partial region thereof, all of which are specific to the genetic recombinant line. This is similar in other context. This is also applied to the meaning of "gene sequence".

The term "genetic recombinant" includes the whole organism into which an exogenous gene has been introduced or a portion of organism into which an exogenous gene has been introduced such as organs, tissue explants, cells (including culture cells), seeds, pollens or embryos from such organisms.

The term "quantitative PCR" generally means a series of reactions which uses PCR for quantifying the template DNA which existed at the beginning of the amplifying reaction. Quantitative PCR includes Internal Standard Method which employs an endogenous sequence as a standard and Competitive Method which employs a molecule competing the amplification reaction. In the present invention, the internal method and PCR were employed where the template DNA which is referred to as a standard molecule and which serves as a standard to determine the number of molecules of each sequence accurately and easily, and the progression of the reaction, namely the extent of amplification, is monitored at any time during the reaction. Thus, "Quantitative PCR" herein used refers to the PCR for quantitatively determining the amount of the template DNA which existed at the beginning of the reaction, wherein the target molecule to be amplified can be monitored for its amplification at any time during the reaction. For the quantification, such PCR and a standard curve is generally combined where the standard curve can associate the number of DNA molecule which existed at the beginning of the reaction with the signal indicating the extent of the amplification of the molecule. The standard curve can be generated by using a standard molecule of which number is known.

Sample DNA, primers, probes, conditions for PCR, and the number of the recombinant DNA molecules, the number of molecules of endogenous gene, and the methods for calculating the quantification ratio, which may be used in the present invention, will be described in detail hereinafter.

The nucleic acids from test plants are preferably the genome DNA from the test plants. The methods of extracting the nucleic acids from the test plants are not limited and any methods of extracting nucleic acids from test plant samples can be used as long as the sufficient quality for PCR is obtained. For example, commercially available kit such as QIAGEN Plant Maxi Kit (QIAGEN GmbH) may be used. Additionally, the methods can be modified, if necessary.

The nucleic acids extracted by such methods are preferably kept in a form which is suitable to be used as a template in PCR, for example, in the form of a solution in a buffer. The purity of the obtained nucleic acids can be estimated by the known methods, for example by determining the absorbance at 230 nm, 260 nm and 280 nm. In such a way, it is preferable for performing PCR method that the ratio of 260 nm/230 nm is more than 2 and the ratio of 260 nm/280 nm is between 1.8 and 2.

The amplification by PCR may be performed using primers corresponding to the endogenous gene in order to confirmed that the prepared DNA solution is purified sufficient to be subjected to PCR and is not degraded.

PCR is performed using thus obtained nucleic acids obtained from test plants. The primer used in the PCR is the pair of primers that can amplify the region containing the entire recombinant DNA sequence or a portion thereof. By using these primers, it is possible to specifically detect a recombinant DNA sequence depending on the structure of the recombinant DNA sequence. Such primer pairs may be designed as described below depending on the genetic recombinants to be detected.

The target genetic recombinant to be detected may be any of the aforementioned genetic recombinants and the types thereof are not limited. Any genetic recombinant may be the target of detection as long as the construct of the introduced DNA sequence is determined. Such a genetic recombinant may not be restricted to the generation where the gene introduction was performed but it may be a variety from its progenies.

Firstly, the nucleotide sequence of the recombinant DNA contained in the genetic recombinant to be tested should be obtained. The nucleotide sequence is not necessary the entire sequence of the recombinant DNA and it may be a nucleotide sequence located in the neighborhood of the target region. Many of such nucleotide sequences are available in the known literatures. Even if the nucleotide sequence is not available from the known literatures, the sequence can be obtained by an experiment if the information of the partial nucleotide sequence thereof is available. In designing a line specific primer pair, it would be easy to select the pair with high specificity by selecting the region extending over plural types of DNA sequences (for example, the region extending from CaMV 35S promoter to cryIA(b)). Each primer pair may be any primer pair as long as it can specifically amplify the target DNA sequence, but it is preferable that the amplified fragment is between 80 bp and 200 bp and the GC content of each primer is between 40% to 60%, respectively, and it is more preferable that each primer does not form intramolecular high-order structures and does not form base pairing over 3 or more contiguous nucleotides.

For example, the primers can be designed from the region shown in FIG. 1 when the progeny varieties from Bt11 line, the progeny varieties from Event176 line, the progeny varieties from MON810 line, the progeny varieties form GA21 line, the progeny varieties from T25 line or the progeny varieties from Roundup Ready Soy line are intended to be specifically and individually detected.

It is also known that the number of the amplified region which existed at the beginning of the reaction, and which is amplified by the primers, can be quantified by quantitative PCR method. Several quantitative PCR methods have been known, but it is required in many cases to prepare a probe complementary to the region which is encompassed by the primer pair. The probe may be any probe which generates a signal corresponding with the number of the molecules which were produced by the amplification, for example, a substance which is suitable to detect, during PCR, the formation of double strand formation of DNA or the dissociation reaction from double strand to single strand, or the extension reaction of nucleic acids. Generally, fluorescence-labeled nucleic acids are used for probes. Specifically, it is preferable that the probe may specifically hybridize to the template DNA under the condition used for the extension reaction by polymerase during the amplification reaction by PCR and may cause the changes in the fluorescence intensity depending on the extension of the DNA strand, that is, the amplification of the template DNA, and said changes preferably indicate the extent of the amplification, more preferably, the probe degrades depending on the amplification of the template DNA to release a fluorophor, which leads to the increase in fluorescent intensity in the reaction mixture and furthermore the increase in florescent intensity is preferably the index of the extent of the amplification. By using such probes, the progress of amplification during PCR may be easily monitored in real time. Such fluorescence-labeled probes are known to those skilled in the art, and suitable fluorescent probes having such properties may also be synthesized. Additionally, it is preferable that the probe has the Tm value about 10° C. higher than the corresponding primer pair and the full length of the probe is preferably between about 18 nucleotides and about 25 nucleotides, and that the probe does not have G at its terminal. In one embodiment of the methods of the present invention, a probe is used where the probe degrades as the amplification progresses, which causes the increase in the fluorescent intensity, and the increase in the fluorescent intensity is the indicator of the amplification.

The qualitative PCR can be performed using the nucleic acids from the test plant sample as the template and using the primer pair designed as described above. Furthermore, the quantitative PCR can be performed using the nucleic acids from the test plant sample as the template and using the primer pair and the probe thus designed. There are not any limitations for the reaction mixture, because the reaction mixture can be easily prepared by those skilled in the art. For example, the reaction mixture can be prepared by using an appropriate amount of template nucleic acids, the primer pair, PCR buffer solution, dNTP, magnesium chloride, DNA polymerase, etc. For example, about 50 ng of DNA extracted from the sample can be used, the reaction can be performed with a final primer concentration of about 0.2-0.5 μm in a total volume of 25. μl. The conditions for PCR are also not limited and it can be performed by maintaining 10 minutes at 95° C., 40 cycles of 30 seconds at 95° C., 30 seconds at 58° C., 30 seconds at 72° C., and maintaining 7 minutes at 72° C. after the 40 cycles and keeping at 4° C. Those skilled in the art could easily optimize the condition and thus, the temperature and the time for each step can be optionally changed. Moreover, such a reaction can be performed using a well-known device.

The number of molecules of the recombinant DNA in the sample can be obtained by performing quantitative PCR. Regarding quantitative PCR, it is known that the value obtained by the determination of the initial amount of the target DNA sequence(s) to be amplified does not always directly indicate the content of the genetic recombinant(s). For example, as is indicated in FIG. 1, since the DNA sequences introduced into genetic recombinants highly differs among lines and the copy number per plant genome of each genetic recombinant has diversity, the content ratio can not be simply calculated. For example, the coding region for cryIA(b) is introduced into Event176 line and Bt11 line as well as MON810 line, and the developers report that two or more copies has been introduced into Event176, one copy for Bt11 and at least one copy has been introduced into MON810. Additionally, PCR is likely to be inhibited by contaminants in the reaction system.

According to the present invention, the number of molecules of a recombinant DNA sequence is determined by, for example, preparing a standard curve by performing quantitative PCR using a known amount of an internal standard, performing the similar quantitative PCR for the sample and determining said number of the molecules using the standard curve.

The number of molecules of the endogenous sequence may be determined by the similar procedure. On the other hand, for pure genetic recombinant, the number of molecules of the DNA sequence in the genetic recombinant and the number of molecules of the internal DNA sequence are predetermined by quantitative PCR to define the ratio of these determined values as the "quantification ratio". Since the quantification ratio represents the unique value depending on the number and type of the recombinant DNA sequence which has been introduced into each genetic recombinant, the diversity of recombinant DNA sequences among the lines is strictly taken into account by converting the quantitative value to the content ratio of the genetic recombinant using Formula (1). According to the present invention, it becomes possible to avoid the errors in the determined values due to, for example, the deranging factor as to the reaction system itself such as PCR inhibitor which may be contained in the sample DNA solution and the differences of yield during the DNA extraction.

The quantification ratio is preferably calculated for each of all of the genetic recombinants which may be possibly contained in the sample, but it is also acceptable that the quantification ratio is obtained only for a part of them. Once the value of quantification ratio is obtained, the content ratio of the genetic recombinant in the original sample can be obtained from the initial amount of the target DNA sequence to be amplified and the initial amount of the internal standard sequence at the beginning of the reaction by using the value of quantification ratio as a coefficient, because the value of the quantification ratio is unique for the target region to be amplified by PCR and the line of the genetic recombinant.

Such an internal standard may be, for example, the specific internal DNA sequence which are share by maize, especially, an internal gene sequence, a specific internal DNA sequence which are share by soybean, especially, an internal gene sequence or an artificially constructed standard molecule.

The standard molecule suitable for the present invention is the recombinant DNA molecule which include, on a single molecule, at least one recombinant DNA sequence which is specific to at least one, preferably two or more lines of genetic recombinants and at least one internal DNA sequences which are shared by the corresponding species to the recombinants. A recombinant DNA molecule which contains, on a single molecule, at least one recombinant DNA which is not specific to each line of the genetic recombinant but is frequently use for genetic recombinants and at least one internal DNA sequences shared by the corresponding species can also be used in the present invention. The recombinant DNA molecule may further contain various sequences to be used for replication in a suitable host or a marker gene for selecting hosts harboring the standard molecule and in addition to the aforementioned sequences. Only the minimum region which can be used as the standard molecule can also be obtained from the recombinant DNA molecule by using appropriate restriction enzymes or by amplifying the part of the molecule by PCR. The recombinant DNA molecule according to the present invention, however, should have the feature that the number of molecules to be subjected to PCR can be easily controlled. For example, when the entire nucleotide sequence according to the present invention is known or the molecular weight is known, the number of molecules to be applied to PCR can be controlled. The nucleotide sequence or the molecular weight of the recombinant DNA molecule can be determined, if necessary.

As the internal DNA sequence, for example, the specific internal gene sequence shared by maize or a part thereof, or the specific internal gene sequence shared by soybean or a part thereof can be used, as described above. As the recombinant DNA sequence which is shared by the genetic recombinants, for example, CaMV 35S promoter sequence, Nos terminator sequence, and a part thereof may be used. As the DNA sequence specific to the individual recombinant line, for example, the DNA sequence derived from the individual gene which has been introduced into each line may be used.

Such a standard molecule may be constructed according to the molecular biological techniques which are well known to those skilled in the art. For example, the molecule may be constructed by sequentially cloning the restriction fragments or repeatedly combining the PCR products using tailed primers. Preferably the molecule is constructed as a recombinant DNA molecule being capable of self-replicating in suitable hosts such as microorganisms, animal cells, and plant cells. When the standard molecule is constructed as a plasmid, it is preferably to use it as a linear molecule after cleaving it by a restriction enzyme because supercoil formation may destabilize the PCR reaction system. In such cases, any restriction enzymes can be used for cleaving as long as the enzymes do not cleave the target DNA sequence to be amplified.

Particularly, in one embodiment of the present invention, the standard molecule contains a part of le1 gene sequence from soybean as the internal DNA sequence, and contains Roundup Ready Soy line specific DNA sequence as the recombinant DNA to be detected. In another embodiment of the present invention, the standard molecule contains a part of zSSIIb gene sequence from maize as the internal standard and contains the DNA sequences specific to GA21, T25, MON810, Event176 and Bt11 line, that it, m-epsps-NOS terminator region, pat-35S terminator region, adh1-1S-cryIA(b) region, cryIA(b)-PEPC#9 region and cryIA(b)-NOS terminator region, respectively. In these embodiments, the standard molecules are the DNA molecules which can self-replicate in *Escherichia coli*.

Particularly, the quantitative PCR according to the present invention and the determination of the number of molecules of the interested DNA sequence may be performed, for example, according to the following.

(i) Preparation of Standard Curve

PCR is performed using different numbers of the standard molecule, the primers for amplifying the DNA sequence specific to the genetic recombinant line or the internal DNA sequence shared by the corresponding species to the recombinant under the presence of the probe which increases fluorescent intensity depending on the progress of the amplification of the internal DNA sequence or of the amplification of the DNA sequence specific to the genetic recombinant. The fluorescence intensity is monitored every pre-determined number of times of cycles for each reaction which uses the defined number of the standard molecules as the template DNA which existed at the beginning of the reaction (FIGS. 14(A),(B)). Then the threshold of fluorescence increase ($\Delta$Rn) is determined in the phase where an exponential relationship is observed between fluorescence intensity and the cycle numbers. For example, $\Delta$Rn is set to $10^{-1}$ in FIG. 14.

The number of PCR cycles reaching the threshold may be plotted against the number of molecules of the DNA template which existed at the beginning of the reaction by taking the number of PCR cycles as a vertical axis and the number of molecules of the template DNA existing at the beginning of the reaction as a horizontal axis to generate the standard curve (FIG. 15).

(ii) PCR for Sample DNAs

Regarding with the DNA sequence specific to a line of a genetic recombinant and an internal DNA sequence shared by the corresponding species to the genetic recombinant, which may be contained in the sample, the quantitative PCR is performed for the DNA sequence specific to the genetic recombinant in the sample and for the internal DNA sequence, respectively. The DNA sequence specific to the genetic recombinant(s) may be the sequence which is specific to each of the genetic recombinant lines or it may be commonly shared by two or more genetic recombinant lines. The PCR for the DNA sequence specific to each genetic recombinant and for the internal DNA sequence may be performed in the same reaction or in the separate reaction as long as it is assured that the template DNA molecule should be identical in the both reactions.

(iii) Determination of the Number of Molecules of the DNA Sequence Specific to the Genetic Recombinant(s) and the Number of Molecules of the Internal DNA Sequence(s)

PCR may be performed for each individual sequence as described above with monitoring the signal as the indicator of the amplification to determine the number of cycles where the signal reaches to the threshold defined in step (i). Then the obtained number of cycles is converted to the number of molecules which existed at the beginning of the reaction by using the standard curve generated in step (i).

When the standard curve as defined in (i) has already obtained, the standard curve may be used for the procedures after step (ii).

Once the number of molecules of the recombinant specific DNA sequence in the sample, the number of molecules of the internal DNA sequence and the quantification ratio for each individual recombinant are obtained, the total content ratio of the genetic recombinants or the individual content ratio of each line contained in the sample can be calculated according to the aforementioned formula (I) or formula (III). In formula (I) or formula (III), either of the DNA sequence which is specific to each of the genetic recombinant lines or the DNA sequence which is not line-specific but which is frequently used for genetic recombinants may be selected as the recombinant DNA sequence to be quantified.

When the former is selected, the total content ratio of the genetic recombinants in the sample may be exactly quantified by summing up the content ratio of each line in the sample after repeatedly analyzing all of the genetic recombinant lines, because the individual content ratio of each individual line in the sample can be exactly defined. Such a method may be a suitable method in many cases for a distribution mode where the samples to be analyzed are the mixture of plural lines in the distribution channel.

When the latter is selected, since the approximate content ratio can be simultaneously determined for plural lines, it may be a suitable standard sample for conveniently quantifying the approximate total content ratio of the entire genetic recombinants in the sample. In such cases, any value of the quantification ratios calculated for the genetic recombinant lines can be selected as the quantification ratio in formula (I), but it is preferable to use the minimal quantification ratio among these values. This will make it possible to estimate the possible maximum value as the content ratio of the genetic recombinants.

EXAMPLES

The following examples may illustrate the present invention but these examples are only for explanation and the scope of the present invention should not be limited to these examples.

In the following examples, the following samples, reagents and devices were employed.

(1) Samples

The dry seeds of the following six varieties were used for maize (*Zea mays*): Genetic recombinant maize: progeny varieties from BT 11 line, Event176 line, MON810 line, T25 line and GA21 line.

Non-recombinant maize: Dairyland 1412

The dry seeds of the following two varieties were used for soybean (*Glycine max*):

Genetic recombinant soybean: progeny varieties from Roundup Ready Soy.

Non-recombinant soybean: species Murayutaka

The dry seeds of the following variety were used for rice (*Oryza sativa*):

Non-recombinant rice: species Kinuhikari

The dry seeds of the following variety were used for wheat (*Triticum aestivum*):

Non-recombinant wheat: species Haruyutaka

The dry seeds of the following variety were used for barely (*Hordeum vulgare*):

Non-recombinant barley: species Harrington (2) Reagents

The following reagents were used for DNA extraction:
Sodium lauryl sulfate (SDS) (guaranteed reagent) (Sigma Chemical Co.)
QIAGEN DNeasy Plant Maxi Kit (QIAGEN GmbH)
QIAGEN DNeasy Plant Mini Kit (QIAGEN GmbH)
The following reagents were used for electrophoresis:
Acetic acid (guaranteed reagent) (Wako Pure Chemical Industries, Ltd.)
Tris[hydroxymethyl]aminomethane (Tris) (guaranteed reagent) (Sigma Chemical Co.)
Ethylene-diamine-teraacetic acid (EDTA) (guaranteed reagent) (Sigma Chemical Co.)
Agarose powder "LO3 ₁TaKaRa┘" (TaKaRa Shuzo Co., Ltd.)
Ethidium bromide (Sigma Chemical Co.)
Ficoll 400 (Sigma Chemical Co.)
Bromphenol blue (Sigma Chemical Co.)
Xylene cyanol (Sigma Chemical Co.)
DNA marker "HindIII digest of lambda" (New England Biolabs Inc.)
DNA marker "1 kb ladder" (New England Biolabs Inc.)
DNA marker "100 bp ladder" (New England Biolabs Inc.)
The following reagents were used for qualitative PCR:
DNA polymerase "AmpliTaq Gold" (PE Biosystems)
×10 PCR buffer II (PE Biosystems)
The following reagents were used for producing and purifying plasmids:
DNA polymerase "AmpliTaq Gold" (PE Biosystems)
×10 PCR buffer II (PE Biosystems)
DNA polymerase "KOD" (TOYOBO Co., Ltd.)
×10 PCR buffer II (TOYOBO Co., Ltd.)
TOPO TA Cloning Kit with TOP10F' Cells (Invitrogen Co.)
Yeast Extract (Difco Laboratories)
Tryptone Peptone (Difco Laboratories)
NaCl (guaranteed reagent) (Wako Pure Chemical Industries, Ltd.)
Agar powder (Syoei Kanten Ltd.)
D[−]-α-Aminobenzylpenicillin (Ampicillin) Sodium Salt (Sigma Chemical Co.)
QIAGEN Plasmid Maxi Kit (QIAGEN GmbH)
ethanol (guaranteed reagent) (Wako Pure Chemical Industries, Ltd.)
2-propanol (guaranteed reagent) (Wako Pure Chemical Industries, Ltd.)
Tris[hydroxymethyl]aminomethane (Tris) (guaranteed reagent) (Sigma Chemical Co.)
Ethylene-diamine-teraacetic acid (EDTA) (guaranteed reagent) (Sigma Chemical Co.)
Restriction Enzyme "HindIII" (TaKaRa Shuzo Co., Ltd.)
Restriction Enzyme "BamHI" (TOYOBO Co., Ltd.)
Restriction Enzyme "SmaI" (New England Biolabs Inc.)
Restriction Enzyme "SrfI" (New England Biolabs Inc.)
Phenol (guaranteed reagent) (Wako Pure Chemical Industries, Ltd.)
chloroform (guaranteed reagent) (Wako Pure Chemical Industries, Ltd.)
isoamyl alcohol (guaranteed reagent) (Wako Pure Chemical Industries, Ltd.)
The following reagent was use for quantitative PCR:
TaqMan Universal PCR Master Mix (PE Biosystems)

(3) Devices

The following devices were used for extracting DNA from samples:
Granulator "Multi Beads Shocker MB301" (Yasui Kikai Co.)
Granulator "DM-6" (Yu Chi Machinery Co., Ltd.)
Touch-Mixer "Tube mixer" (Yamato Scientific Co., Ltd.)
Ultrademineralizer "CPW-200" (ADVANTEC Toyo Kaisya Ltd.)
Incubator "Thermo Minder SD mini" (TAITEC Co.)
Centrifuge "himac CT13" (Hitachi Koki Co., Ltd.)
Centrifuge "himac CF15D2" (Hitachi Koki Co., Ltd.)
Centrifuge "Allegra™ 6KR" (Beckman Coulter, Inc.)
Spectrophotometer "DU7400" (Beckman Coulter, Inc.)
The following devices were used for DNA electrophoresis:
Electrophoresis apparatus "Mupid 2" (Advance Co., Ltd.)
Imaging analyzer "Molecular Imager$^R$ FX" (BioRad Laboratories Inc.)
The following devices were used for qualitative PCR:
Thermal Cycler "PTC-200" (MJ Research Inc.)
Thermal Cycler "PCR System 9700" (PE Biosystems)
The following devices were used for producing and purifying plasmids:
Shaking incubator "Thermostat Shaking Incubator AT24R" (Thomas Kagaku Co., Ltd.)
Thermal Cycler "PTC-200" (MJ Research Inc.)
Thermal Cycler "PCR System 9700" (PE Biosystems)
Centrifuge "himac CT13" (Hitachi Koki Co., Ltd.)
Centrifuge "himac CF15D2" (Hitachi Koki Co., Ltd.)
The following devices were used for quantitative PCR:
Quantitative PCR apparatus "ABI PRISM 7700 Sequence Detector System" (PE Biosystems)
Quantitative PCR apparatus "ABI PRISM 5700 Sequence Detector System" (PE Biosystems)

(4) Others

The primer synthesis was consigned to Greiner Japan K.K.
The probe synthesis was consigned to PE Biosystems Japan K.K.
The verification of DNA sequences was consigned to Greiner Japan K.K.

Example 1

DNA Extraction

The extraction of DNA from maize, soybean, rice, wheat, barley was carried out according to the following procedures. Firstly, the samples were ground to powder by granulator "DM-6" (Yu Chi Machinery Co., Ltd.), then 500-1,000 mg was weighed from the ground products and the DNAs were extracted from the ground products using QIAGEN DNeasy Plant Maxi Kit (QIAGEN GmbH) according to the manufacturer's protocol.

To extract the DNA from a single grain of maize or soybean, the surface of the grain was firstly washed well with 1% SDS before crushing by granulator "Multi Beads Shocker MB301" (Yasui Kikai Co.), and then the whole ground product was used for DNA extraction.

The DNA extraction from the blind samples described in Examples 12, 13 and 14 was carried out according to the following procedure. This will be described for maize as an example, but the similar procedure can be carried out for soybean. Firstly the genetic recombinant maize and non-recombinant maize were washed by 1% SDS solution, respectively, before drying. After that, they are ground separately by granulator "DM-6" (Yu Chi Machinery Co., Ltd.) and 1 g from each of the ground products was weighed, the genetic recombinant maize and non-recombinant maize were mixed by using granulator "DM-6" (Yu Chi Machinery Co., Ltd.). 500-1,000 mg was weighed from the mixed sample and the DNA was extracted form the ground products using QIAGEN DNeasy Plant Maxi Kit (QIAGEN GmbH) according to the manufacturer's protocol. 1 μL each from all of the extracted DNA solutions was subjected to electrophoresis after mixing with 1 μL of 10× loading buffer (20% Ficoll 400, 0.1 M EDTA, 1.0% SDS, 0.25 bromphenol blue, 0.25% Xylene Cyanol) to confirm that the degradation was not occurred during the extraction process. Namely, the electrophoresis was carried out by using electrophoresis apparatus "Mupid 2" (Advance Co., Ltd.) and 0.8% agarose gel containing 50 μg of ethidium bromide (Sigma Chemical Co.) in TAE buffer (0.04M Tris, 0.04M Acetic Acid, 0.001M EDTA) at 100V for 15 minutes. The DNAs in the gel were confirmed by imaging analyzer "Molecular Imager$^R$ FX" (BioRad Laboratories Inc.).

Additionally, 1 μL each from all of the extracted DNA solutions was subjected to spectrophotometry to determine the concentration and the purity thereof. Namely, the absorbance of the sample at 230 nm, 260 nm, 280 nm which was diluted with 49 μL TE buffer to bring a 50-fold dilution and the concentration and the purity thereof was calculated using 1 $A_{260}$ Unit=50 μg.

All the extracted DNA was stored at −20° C.

Example 2

Selection of the Regions for Detection (Designing the Primer Pairs and Probes The recombinant DNA sequences are determined by using the DNA extracted from each progeny variety of the genetic recombinant lines with the sequencing primers shown in Table 1.

TABLE 1

Sequencing Primer

| Primer | SEQ ID NO | nucleotide sequence (5'->3') |
|---|---|---|
| cry1A 1-5' | 1 | TGG ACA ACA ACC CAA ACA TCA A |
| T35S 2-3' | 2 | TGG ATT TTG GTT TTA GGA ATT AGA AA |
|  |  |  |
| adh1 1-5' | 3 | GCA CTG AAT TTG TGA ACC C |
| NOS ter 1-3' | 4 | CTA TAT TTT GTT TTC TAT CGC |
|  |  |  |
| P35S-5' | 5 | ATT GAT GTG ATA TCT CCA CTG ACG T |
| NOS ter 2-3' | 6 | TTA TCC TAG TTT GCG CGC TA |
|  |  |  |
| rAct pro-5' | 7 | ATC TTT GGC CTT GGT AGT TTG |
| NOS ter-3' | 8 | ATT GCG GGA CTC TAA TCA TAA |
|  |  |  |
| P35S-5' | 9 | ATT GAT GTG ATA TCT CCA CTG ACG T |
| T35S-3' | 10 | ACT AAG GGT TTC TTA TAT GCT CAA CA |
|  |  |  |
| CM01 | 11 | CAC TAC AAA TGC CAT CAT TGC GAT A |
| CR01 | 12 | GAT GTT TGG GTT GTT GTC CAT |
|  |  |  |
| CaM03-5' | 13 | CCT TCG CAA GAC CCT TCC TCT ATA |
| EPSPS01-3' | 14 | ATC CTG GCG CCC ATG GCC TGC ATG |

TABLE 1-continued

Sequencing Primer

| Primer | Region | Target for amplification | Length of amplified region |
|---|---|---|---|
| Cry1A 1-5'<br>T35S 2-3' | cry1A(b)/sense<br>35S ter/anti-sense | Event176 | 2.1 kb |
| adh1 1-5'<br>NOS ter 1-3' | Adh1-1S IVS6/sense<br>NOS ter/anti-sense | Bt11 | 2.1 kb |
| P35S-5'<br>NOS ter 2-3' | P35S/sense<br>NOS ter/anti-sense | Bt11 | 1.1 kb |
| rAct pro-5'<br>NOS ter-3' | rActin pro/sense<br>NOS ter/anti-sense | GA21 | 2.3 kb |
| P35S-5'<br>T35S-3' | P35S/sense<br>35S ter/anti-sense | T25 | 0.8 kb |
| CM01<br>CR01 | CaMV/sense<br>cry1A(b)/anti-sense | MON810 | 1.4 kb |
| CaM03-5'<br>EPSPS01-3' | P35S/sense<br>CP-4-epsps anti-sense | Roundup Ready Soy | 513 bp |

<Sequence Listing Free Text>

SEQ ID NO: 1-14: PCR primer

The primer pair for amplifying the DNA sequence which is specific to the genetic recombinant line was designed to amplify the region extending over plural DNA sequence contained in the introduced DNA sequence. Namely, the primer pairs were designed for amplifying cryIA(b)—Nos terminator and adh1-S-cryIA(b) for the progeny varieties from Bt11 lline, cryIA(b)—PEPC#9 for the progeny varieties from Event 176 line, hsp 70-cryIA(b) for the progeny varieties from MON810 line, pat-35S for the progeny varieties from T25 line, m-epsps-NOS and OPT-m-epsps for the progeny varieties from GA21 line and CPT4-CP4-epsps for the progeny varieties from Roundup Ready Soy line.

The primer pair for amplifying the DNA sequence which is not line-specific but frequently used for the genetic recombinants was designed to amplify an internal sequence of CaMV 35S promoter sequence or an internal sequence of NOS terminator sequence.

Additionally, an internal sequence of zSSIIb gene for maize or the internal sequence of le1 gene for soybean was selected as the DNA sequence of the specific endogenous gene which the organism possesses. These sequences were obtained by searching over genome database to design the primers.

The probe having the Tm value about 10° C. higher than the Tm values of the primers was designed between the primers (Table 2A and 2B).

TABLE 2A

Primers/Probes for maize

| SEQ ID NO | Primer/Probe | Amplified region<br>Amplification target | Amplified length |
|---|---|---|---|
| 15 | SSIIb 1-5' | zSSIIb/sense | 151 bp |
| 16 | SSIIb 1-3' | zSSIIb/anti-sense | |
| 17 | SSIIb-Taq | maize intrinsic | |
| 18 | P35S 1-5' | 35S-pro/sense | 101 bp |
| 19 | P35S 1-3' | 35S-pro/anti-sense | |
| 20 | P35S-Taq | CaM35S-pro | |
| 21 | NOS ter 2-5' | NOS-ter/sense | 151 bp |
| 22 | NOS ter 2-3' | NOS-ter/anti-sense | |
| 23 | NOS-Taq | NOS ter | |
| 24 | E176 2-5' | cry1A(b)/sense | 100 bp |
| 25 | E176 2-3' | PEPC#9 intron/anti-sense | |

TABLE 2A-continued

| | Primers/Probes for maize | | |
|---|---|---|---|
| 26 | E176-Tag | Event176 | |
| 27 | Bt11 2-5' | cry1A(b)/sense | 151 bp |
| 28 | Bt11 2-3' | NOSter/anti-sense | |
| 29 | Bt11-Taq | Bt11 | |
| 30 | GA21 2-5' | m-epsps/sense | 141 bp |
| 31 | GA21 2-3' | NOS ter/anti-s | |
| 32 | GA21-Taq | GA21 | |
| 33 | T25 1-5' | pat/sense | 149 bp |
| 34 | T25 1-3' | 35S-ter/anti-sense | |
| 35 | T25-Taq | T25 | |
| 36 | M810 2-5' | hsp70/sense | 113 bp |
| 37 | M8102-3' | cry1A(b)/anti-sense | |
| 38 | M810-Tag | MON810 | |
| 39 | Bt11 3-5' | adh1-S1VS6/sense | 128 bp |
| 40 | Bt11 3-3' | cry1A(b)/anti-sense | |
| 41 | Bt11 2-Tag | Bt11 | |
| 42 | GA21 3-5' | OTP/sense | 133 bp |
| 43 | GA21-3-3' | m-epsps/anti-sense | |
| 44 | GA21 2-Tag | GA21 | |
| 77 | SSIIb 2-5' | zSSIIb/sense | 133 bp |
| 78 | SSIIb 2-3' | zSSIIb/anti-sense | |
| 79 | SSIIb 3-5' | zSSIIb/sense | 114 bp |
| 80 | SSIIb 3-3' | zSSIIb/anti-sense | |

| SEQ ID NO | |
|---|---|
| 15 | CTC CCA ATC CTT TGA CAT CTG C |
| 16 | TCG ATT TCT CTC TTG GTG ACA GG |
| 17 | 5'-Fam-AGC AAA GTC AGA GCG CTG CAA TGC A-Tamra-3' |
| 18 | ATT GAT GTG ATA TCT CCA CTG ACG T |
| 19 | CCT CTC CAA ATG AAA TGA ACT TCC T |
| 20 | 5'-Fam-CCC ACT ATC CTT CGC AAG ACC CTT CCT-Tamra-3' |
| 21 | GTC TTG CGA TGA TTA TCA TAT AAT TTC TG |
| 22 | CGC TAT ATT TTG TTT TCT ATC GCG T |
| 23 | 5'-Fam-AGA TGG GTT TTT ATG ATT AGA GTC CCG CAA-Tamra-3' |
| 24 | TGT TCA CCA GCA GCA ACC AG |
| 25 | ACT CCA CTT TGT GCA GAA CAG ATC T |
| 26 | 5'-Fam-CCG ACG TGA CCG ACT ACC ACA TCG A-Tamra-3' |
| 27 | TTA GCG CTC ATG TGT TCA ATT CT |
| 28 | CGG CAA CAG GAT TCA ATC TTA A |
| 29 | 5'-Fam-ACA TTG ACC GTA TTG AGT TTG TGC CTG CC-Tamra-3' |
| 30 | GAC CTT CCC CGA CTA CTT CGA |
| 31 | ATC GCA AGA CCG GCA ACA |
| 32 | 5'-Fam-CGA ATT CCC CGA TCG TT CAA ACA TTT-Tamra-3' |
| 33 | GCC AGT TAG GCC AGT TAC CCA |
| 34 | TGA GCG AAA CCC TAT AAG AAC CCT |
| 35 | 5'-Fam-CAT GCC CGC TGA AAT CAC CAG TCT CT-Tamra-3' |
| 36 | GAT GCC TTC TCC CTA GTG TTG A |
| 37 | GGA TGC ACT CGT TGA TGT TTG |

TABLE 2A-continued

Primers/Probes for maize

| | |
|---|---|
| 38 | 5'-Fam-AGA TAC CAA GCG GCC ATG GAC AAC AA -Tamra-3' |
| 39 | CAA TGC GTT CTC CAC CAA GTA CT |
| 40 | AAA AGA CCA CAA CAA GCC GC |
| 41 | 5'-Fam-CGA CCA TGG ACA ACA ACC CAA ACA TCA-Tamra-3' |
| 42 | ATC CGG TTG GAA AGC GAC TT |
| 43 | GAA GCC TCG GCA ACG TCA |
| 44 | 5'-Fam-AAG GAT CCG GTG CAT GGC CG-Tamra-3' |
| 77 | TCC CAA TCC TTT GAC ATC TGC T |
| 78 | GAC AGG AGC TGA TGG ATG ATC AG |
| 79 | CCA ATC CTT TGA CAT CTG CTC C |
| 80 | GAT CAG CTT TGG GTC CGG A |

<Sequence Listing Free Text>
SEQ ID NOs: 15, 16, 18, 19, 21, 22, 24, 25, 27, 28, 30, 31, 33, 34, 36, 37, 39, 40, 42, 43, 77, 78, 79, 80: PCR primer
SEQ ID NO:17: Probe for maize zSSIIB
SEQ ID NO:20: Probe for CaMV 35S promoter
SEQ ID NO:23: Probe for NOS terminator
SEQ ID NO:26: Probe for Event176
SEQ ID NO:29: Probe for Bt11
SEQ ID NO:32: Probe for GA21
SEQ ID NO:35: Probe for T25
SEQ ID NO:38: Probe for MON810
SEQ ID NO:41: Probe for Bt11
SEQ ID NO:44: Probe for GA21

TABLE 2B

Primers/Probes for soybean

| SEQ ID NO | Primer/Probe | Designed region Amplification target | Amplified length |
|---|---|---|---|
| 45 | Le1n02-5' | le1/sense | 118 bp |
| 46 | Le1n 02-3' | le1/anti-sense | |
| 47 | Le1-Taq | soy intrinsic | |
| 48 | RRS 01-5' | CTP4/sens | 121 bp |
| 49 | RRS 01-3' | CP4-_epsps_/anti-sense | |
| 50 | RRS-Taq | Roundup Ready Soy | |
| 18 | P35S 1-5' | 35S-pro/sense | 101 bp |
| 19 | P35S 1-3' | 35S-pro/anti-sense | |
| 20 | P35S-Taq | CaM35S-pro | |
| 21 | NOS ter 2-5' | NOS-ter/sense | 151 bp |
| 22 | NOS ter 2-3' | NOS-ter/anti-sense | |
| 23 | NOS-Taq | NOS ter | |

| SEQ ID NO | Nucleotide sequence (5'->3') |
|---|---|
| 45 | GCC CTC TAC TCC ACC CCC A |
| 46 | GCC CAT CTG CAA GCC TTT TT |
| 47 | 5'-Fam-AGC TTC GCC GCT TCC TTC AAC TTC AC-Tamra-3' |
| 48 | CCT TTA GGA TTT CAG CAT CAG TGG |
| 49 | GAC TTG TCG CCG GGA ATG |
| 50 | 5'-Fam-CGC AAC CGC CCG CAA ATC C-Tamra-3' |
| 18 | ATT GAT GTG ATA TCT CCA CTG ACG T |
| 19 | CCT CTC CAA ATG AAA TGA ACT TCC T |
| 20 | 5'-Fam-CCC ACT ATC CTT CGC AAG ACC CTT CCT-Tamra-3' |

TABLE 2B-continued

Primers/Probes for soybean

| 21 | GTC TTG CGA TGA TTA TCA TAT AAT TTC TG |
| 22 | CGC TAT ATT TTG TTT TCT ATC GCG T |
| 23 | 5'-Fam-AGA TGG GTT TTT ATG ATT AGA GTC CCG CAA-Tamra-3' |

<Sequence Listing Free Text>
SEQ ID NOs: 45, 46, 48, 49: PCR primer
SEQ ID NO: 47: Probe for soybean le1
SEQ ID NO: 50: Probe for Roundup Ready Soy Example 3

Confirmation of Specificity of Primer Pairs (Qualitative PCR)

Confirmation was made whether the primer pairs designed in Example 2 were capable of specifically detecting only their target sequences in qualitative PCR.

As the maize samples, progeny varieties from Bt11 line, Event176 line, MON810 line, GA21 line and T25 line and a non-recombinant maize Dairyland 1412 were used. As the soybean samples, a progeny variety from Roundup Ready Soy line and a non-recombinant soybean Murayutaka were used. In total eight kinds of DNA were extracted from the individual sample in the same manner as in Example 1.

Since there is a possibility of contamination with main crops other than maize and soybean in real assay samples, three kinds of DNA were also extracted from rice (species Kinuhikari), wheat (species Haruyutaka) and barley (species Harrington), respectively, in the same manner as in Example 1.

The eleven kinds in total of DNA extracted above were used as the PCR templates and distilled water was used as a negative control in the qualitative PCR. The reaction was performed using Thermal Cycler "PTC-200" (MJ Research Inc.). In the experiment, each of the primers was used in the PCR solution at a final concentration of 0.5 µM. The DNA extracted from the individual samples (templates) was used in an amount of 25 ng per reaction system. As a PCR enzyme, a DNA polymerase "AmpliTaq Gold" (PE Biosystems) was used in an amount of 0.625 Unit per reaction system. As a reaction buffer, ×10 PCR Buffer II (PE Biosystems) was used in a volume of 2.5 µL, and $MgCl_2$ and dNTPs were used in concentrations of 1.5 mM and 200 µM, respectively, per reaction system. The reaction system was made up to 20 µL with distilled water.

The reaction conditions employed were as follows: maintaining for 10 minutes at 95° C., 40 cycles of 30 seconds at 95° C., 30 seconds at 58° C. and 30 seconds at 72° C., followed by maintaining for 7 minutes at 72° C. and keeping at 4° C.

After the reaction was completed, 5 µL was sampled from the reaction solution, mixed with 1 µL of a 10× loading buffer, and then subjected to electrophoresis on 3% agarose gel in TAE buffer at 100V for 15 minutes using an electrophoresis apparatus "Mupid 2" (Advance Co., Ltd.). After the gel was stained with ethidium bromide (Sigma Chemicals Co.) for 15 minutes, the presence of PCR amplification products was confirmed using an image analyzer "Molecular Imager$^R$ FX" (BioRad Laboratories Inc.).

An example of the results of the experiment is shown in FIG. 2. It was confirmed that the primer pair designed for the detection of progeny variety from T25 line were capable of specifically detecting only the progeny variety from T25 line and showed no cross reaction with other samples.

All of the results confirmed in the same manner are summarized in Table 3. As shown in Table 3, it was confirmed that all of the primer pairs were capable of specifically detecting only their target progeny varieties from genetic recombinant lines, respectively.

TABLE 3

Specificities of the primer pairs and the probes

| | Amplified Region | | | | |
|---|---|---|---|---|---|
| Template DNA | zSSIIb | CaMV 35S Promoter | NOS terminator | Bt11 specific | T25 specific |
| non-recombinant maize | + | – | – | – | – |
| Bt11 | + | + | + | + | – |
| T25 | + | + | – | – | + |
| GA21 | + | – | + | – | – |
| Event176 | + | + | – | – | – |
| MON810 | + | + | – | – | – |
| non-recombinant soybean | – | – | – | – | – |
| RRS*[1] | – | + | + | – | – |
| Barley | – | – | – | – | – |
| Wheat | – | – | – | – | – |
| Rice | – | – | – | – | – |

| | Amplified Region | | | | |
|---|---|---|---|---|---|
| Template DNA | GA21 specific | Event176 Specific | MON810 specific | le1 | RRS*[1] specific |
| non-recombinant maize | – | – | – | – | – |
| Bt11 | – | – | – | – | – |
| T25 | – | – | – | – | – |
| GA21 | + | – | – | – | – |
| Event176 | – | + | – | – | – |
| MON810 | – | – | + | – | – |
| non-recombinant soybean | – | – | – | + | – |
| RRS*[1] | – | – | – | + | + |
| Barley | – | – | – | – | – |
| Wheat | – | – | – | – | – |
| Rice | – | – | – | – | – |

*[1] Roundup Ready Soy, +: positive, –: Negative

Example 4

Confirmation of Specificity of Primer Pairs and Probes (Quantitative PCR)

Confirmation was made whether the primer pairs and primers designed in Example 2 were capable of specifically detecting only their target sequences in the quantitative PCR.

As in the case of Example 3, as the maize samples, progeny varieties from Bt11 line, Event176 line, MON810 line, GA21 line and T25 line and a non-recombinant maize Dairyland 1412 were used; and, as the soybean samples, a progeny variety from Roundup Ready Soy line and a non-recombinant soybean Murayutaka were used. In total eight kinds of DNA were extracted from the individual samples in the same manner as in Example 1.

Since there is a possibility of contamination with main crops other than maize and soybean in real assay samples, three kinds of DNA were also extracted from rice (species Kinuhikari), wheat (species Haruyutaka) and barley (species Harrington) in the same manner as in Example 1.

The 11 kinds in total of DNA extracted above were used as the PCR templates and distilled water was used as a negative control in the quantitative PCR. The reaction was performed using a quantitative PCR apparatus "ABI PRISM 7700 Sequence Detector System" (PE Biosystems). In the experiment, each of the primers was used in a final concentration of 0.5 μM and the primer was used in a final concentration of 0.2 μM in the reaction solution. The DNA extracted from the individual sample (template) was used in an amount of 50 ng per reaction system, and TaqMan Universal PCR Master Mix (PE Biosystems; hereinafter, simply referred to as "Master Mix") was used in a volume of 12.5 μL per reaction system. The reaction system was made up to 25 μL.

The reaction conditions employed were as follows: maintaining the reaction solution for 2 minutes at 50° C. and then 10 minutes at 95° C., 40 cycles of 30 seconds at 95° C. and 1 minute at 59° C., followed by keeping at 25° C.

During the reaction, the fluorescent intensity in each reaction well was measured over time. Wells which show the increase in fluorescent intensity can be identified by analyzing the time course of change in fluorescent intensity in each well after the reaction is completed. The fluorescent intensity increased as a result of the degradation of the probe in association with the PCR amplification. Accordingly, in a well in which the increase in fluorescent intensity is observed, it is deemed that PCR amplification occurs and the probe is degraded.

An example of the results of the experiment is shown in FIG. 3. It was confirmed that the primer pair and probe designed for detection of NOS terminator were capable of specifically detecting only the progeny varieties from Bt11 line, Event176 line and Roundup Ready Soy line and showed no cross reaction with other samples.

All of the results confirmed in the same manner are summarized in Table 4. As shown in Table 4, it was confirmed that all of the primers and probes were capable of specifically detecting only their target progeny varieties from genetic recombinant lines, respectively.

TABLE 4

Specificities of the probes and the primer pairs

| Template DNA | Amplified Region | | | | |
|---|---|---|---|---|---|
| | zSSIIb | CaMV 35S promoter | NOS terminator | Bt11 specific | T25 specific |
| non-recombinant maize | + | − | − | − | − |
| Bt11 | + | + | + | + | − |
| T25 | + | + | − | − | + |
| GA21 | + | − | + | − | − |
| Event176 | + | + | − | − | − |
| MON810 | + | + | − | − | − |
| non-recombinant soybean | − | − | − | − | − |
| RRS*[1] | − | + | + | − | − |
| Barley | − | − | − | − | − |
| Wheat | − | − | − | − | − |
| Rice | − | − | − | − | − |

| Template DNA | Amplified Region | | | | |
|---|---|---|---|---|---|
| | GA21 specific | Event176 specific | MON810 specific | le1 | RRS*[1] specific |
| non-recombinant maize | − | − | − | − | − |
| Bt11 | − | − | − | − | − |
| T25 | − | − | − | − | − |
| GA21 | + | − | − | − | − |
| Event176 | − | + | − | − | − |
| MON810 | − | − | + | − | − |
| non-recombinant soybean | − | − | − | + | − |
| RRS*[1] | − | − | − | + | + |
| Barley | − | − | − | − | − |
| Wheat | − | − | − | − | − |
| Rice | − | − | − | − | − |

*[1]Roundup Ready Soy, +: positive, −: negative

Example 5

Production of Standard Molecules (Maize)

Figure 4:
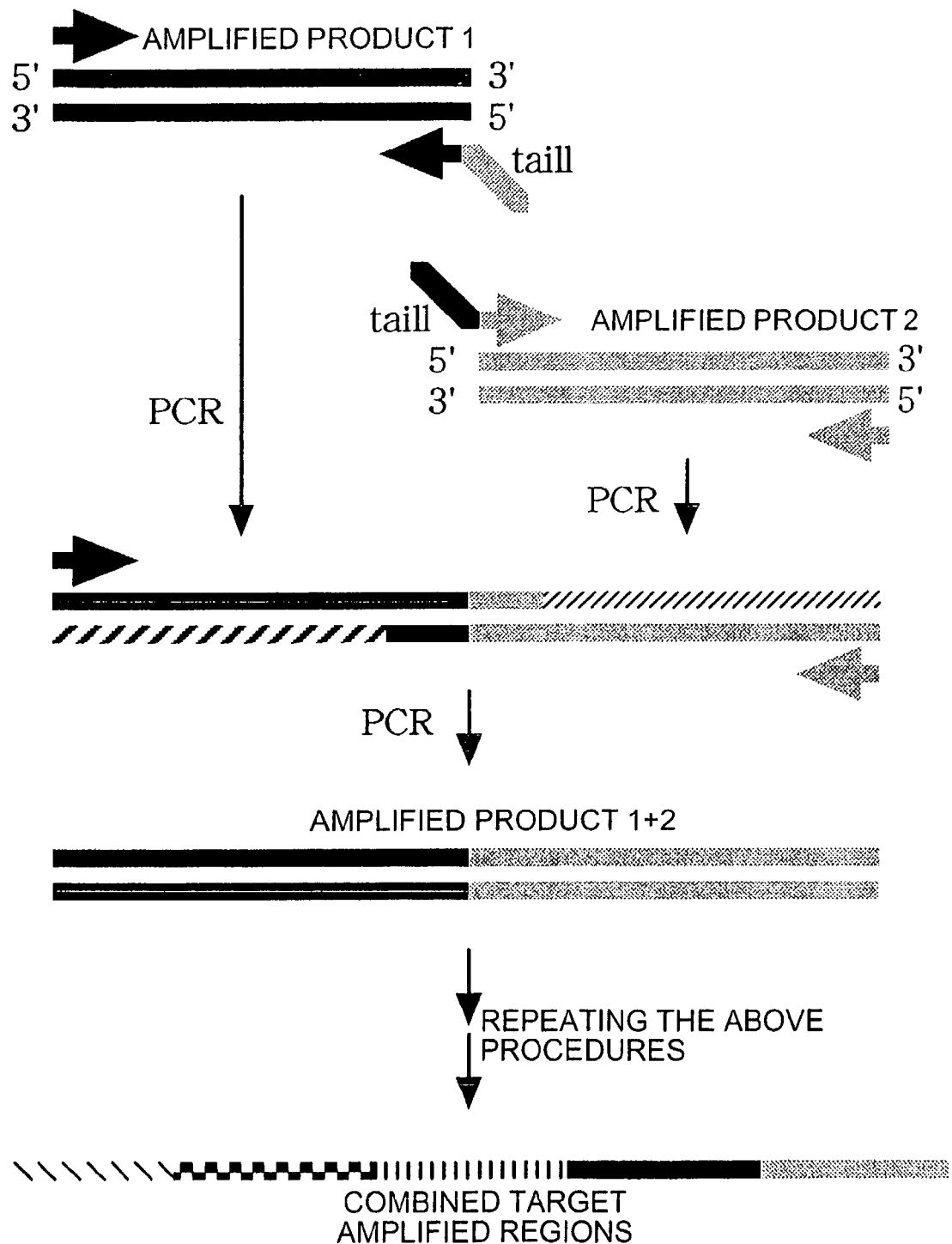
FIG. 4 shows the scheme of the procedure for combining the PCR products.

Integration of the regions to be detected which were selected in Example 2 was performed according to the procedure schematically shown in FIG. 4.

Namely, PCR was performed using the tailed primers shown in Table 5 and the DNA extracted from the corresponding genetic recombinant lines as templates successively to give PCR products having on their terminus other sequences complementary to the target regions to be detected.

PCR was performed using a reaction system containing 10 ng of DNA from maize as a template, 0.5 μM of each tailed primer, 0.156 Unit of DNA polymerase "KOD", (TOYOBO Co., Ltd.), 160 μM of dNTPs, 1.5 mM of $MgCl_2$ and 2.5 μL of ×10 PCR buffer II (TOYOBO Co., Ltd.), which was made up to a total volume of 25 μL with distilled water.

The reaction conditions employed were as follows: maintaining for 1 minute at 98° C. and then 35 cycles of 30 seconds at 98° C., 30 seconds at 54° C. and 1 minute at 74° C., followed by maintaining for 2 minutes at 74° C. and keeping at 4° C.

Each of the resulting PCR products, together with one of the PCR product in which a region to be adjacent to the region contained in that PCR product was amplified, was subjected to integration reaction utilizing PCR. Namely, 0.25 μL of the individual PCR products amplified previously were mixed with 0.156 Unit of DNA polymerase "KOD" (TOYOBO Co., Ltd.), 160 μM of dNTPs, 1.5 mM of $MgCl_2$ and 2.5 μL of ×10 PCR buffer II (TOYOBO Co., Ltd.), which was made up to a total volume of 24.5 PL with distilled water. First, the reaction system was subjected to PCR amplification without any primer.

The reaction conditions employed were as follows: maintaining for 1 minute at 98° C. and then 8 cycles of 30 seconds at 98° C., 30 seconds at 56° C. and 1 minute at 74° C., at which point of time the reaction was terminated.

Next, the individual outmost primers were added to the reaction system in an amount of 0.5 μM, and the PCR amplification was further performed to give an amplification product having the two regions combined.

The reaction conditions employed in the second reaction were as follows: maintaining for 1 minute at 98° C. and then 35 cycles of 30 seconds at 98° C., 30 seconds at 56° C. and 1 minute at 74° C., followed by maintaining for 2 minutes at 74° C. and keeping at 4° C.

By repeating the integration reaction in the similar manner, molecules shown in FIGS. 5 and 6 were produced. The molecule shown in FIG. 5 has a zSSIIb (GENBANK Accession No. AF019297) DNA sequence of amplification target integrated between nucleotide 1 to 151, a CaMV 35S promoter DNA sequence of amplification target integrated between nucleotide 152 to 252, a NOS terminator DNA sequence of amplification target integrated between nucleotide 275 to 425, a GA21 line-specific DNA sequence of amplification target integrated between nucleotide 441 to 581, a T25 line-specific DNA sequence of amplification target integrated between nucleotide 582 to 730, a MON810 line-specific DNA sequence of amplification target integrated between nucleotide 731 to 843, a Event176 line-specific DNA sequence of amplification target integrated between nucleotide 844 to 951 and a Bt11 line-specific DNA sequence of amplification target integrated between nucleotide 952 to 1102. The sequence of this region is shown in SEQ ID NO:57. The nucleotide sequence of the molecule of FIG. 5 is shown in SEQ ID NO:73.

The molecule shown in FIG. 6 has a zSSIIb DNA sequence of amplification target integrated between nucleotide 1 to 151, a CaMV 35S promoter DNA sequence of amplification target integrated between nucleotide 152 to 252, a NOS terminator DNA sequence of amplification target integrated between nucleotide 275 to 425, a GA21 line-specific DNA sequence of amplification target integrated between nucleotide 441 to 573, a T25 line-specific DNA sequence of amplification target integrated between nucleotide 574 to 722, a MON810 line-specific DNA sequence of amplification target integrated between nucleotide 723 to 835, a Event176 line-specific DNA sequence of amplification target integrated between nucleotide 836 to 943 and a Bt11 line-specific DNA sequence of amplification target integrated between nucleotide 944 to 1071. The nucleotide sequence of the molecule of FIG. 6 is shown in SEQ ID NO:74.

TABLE 5

| SEQ ID NO | Primer | |
|---|---|---|
| 51 | SSIIB-P35S-5' | CATTTGGAGAGGTCG ATT TCT CTC TTG |
| 52 | SSIIB-P35S-3' | GAGAGAAATCGACCT CTC CAA ATG AAA |
| 53 | P35S-SrfI-NOS-5' | TATCACATCAATGCCCGGGCG AAT CCT GTT GCC GG |
| 54 | P35S-SrfI-NOS-3' | GGCAACAGGATTCGCCCGGGCATT GAT GTG ATA TCT |
| 55 | NOS-EPN-5' | AAACTAGGATAAATC GCA AGA CCG GCA |
| 56 | EPN-T25-5' | TCGGGGAAGCTCTGA GCG AAA CCC TAT |
| 57 | T25-M810-5' | GGCCTAACTGGCGGA TGC ACT CGT TGA |
| 58 | T25-M810-3' | ACGAGTGCATCCGCC AGT TAG GCC AGT |
| 59 | M810-E176-5' | GGAGAAGGCATCGACTGACTA CTC CAC |
| 60 | M810-E176-3' | GAGTAGTCAGTCGAT GCC TTC TCC CTA |
| 61 | E176-Bt11-5' | TGCTGGTGAACACGG CAA CAG GAT TCA |
| 62 | E176-Bt11-3' | ATCCTGTTGCCGTGT TCA CCA GCA GCA |
| 63 | Le1n-C-EP-3' | CGGCGACAAGTCGCC CAT CTG CAA GCC |
| 64 | C-EP-Le1n-3' | TTGCAGATGGGCGAC TTG TCG CCG GGA |
| 65 | NOS-GA21(OTP)-5' | AAACTAGGATAA ATC CGG TTG GAA AGC |
| 66 | GA21(OTP)-NOS-3' | TTCCAACCGGATTTA TCC TAG TTT GCG |
| 67 | GA21(OTP)-T25-5' | TGCCGAGGCTTC TGA GCG AAA CCC TAT |
| 68 | T25-GA21(OTP)-3' | GGGTTTCGCTCAGAA GCC TCG GCA ACG |
| 69 | E176-Bt11(adh)-5' | TGCTGGTGAACA TCA ATG CGT TCT CCA |
| 70 | Bt11(adb)-E176-3' | AGAACGCATTGA TGT TCA CCA GCA GCA |
| 71 | Le1-NOS-5' | GGAGTAGAGGGCTTA TCC TAG TTT GCG |
| 72 | NOS-Le1-3' | AAACTAGGATAAGCC CTC TAC TCC ACC |

TABLE 5-continued

Pro: Promoter

| SEQ ID NO | Combined Region |
|---|---|
| 51 | SSIIb+35S Pro |
| 52 | SSIIb+35SPro |
| 53 | 35S Pro+NOS |
| 54 | 35S Pro+NOS |
| 55 | NOS+GA21 |
| 56 | GA21+T25 |
| 57 | T25+M810 |
| 58 | T25+M810 |
| 59 | M810+E176 |
| 60 | M810+E176 |
| 61 | E176+Bt11 |
| 62 | E176+Bt11 |
| 63 | le1+RRS |
| 64 | le1+RRS |
| 65 | NOS+GA21 |
| 66 | NOS+GA21 |
| 67 | GA21-T25 |
| 68 | GA21+T25 |
| 69 | E176+Bt11 |
| 70 | E176+Bt11 |
| 71 | Le1+NOS |
| 72 | NOS+Le1 |

<Sequence Listing Free Text>

SEQ ID NOs: 51-72: PCR primers;

SEQ ID NOs: 73-74: Target regions for amplification of standard molecules to be used for quantitative detection of maize genetic recombinants; and SEQ ID NO: 75: A target region for amplification of a standard molecule to be used for quantitative detection of soybean genetic recombinants.

Each of the integrated molecules prepared above was re-amplified using DNA polymerase "AmpliTaq Gold" (PE Biosystems), and ligated into a plasmid vector using TOPO TA Cloning Kit with TOP 10F' Cells (Invitrogen Co.). An *E. coli* host vector system was used, so that the molecules could be supplied readily and infinitely.

Namely, 1 μL of each of the integrated molecules prepared above (template) was subjected to PCR amplification under the same conditions as in Example 3. After the reaction, 1 μL of the reaction solution was mixed with 1 μL of plasmid vector pCR2.1 TOPO and 1 μL of salt buffer, and the mixture was allowed to stand at room temperature for 5 minutes. Two μL of the reaction solution was mixed with *E. coli* strain TOP 10F' Cells included in the kit, allowed to stand on ice for 5 minutes, and then subjected to heat shock treatment at 42° C. for 30 seconds to perform transformation.

One hundred μL of the solution containing the transformants was plated on a LB (ampicillin) plate [composition per L: 10 g of tryptone peptone (Difco Laboratories), 5 g of yeast extract (Difco Laboratories), 5 g of NaCl (Wako Pure Chemical Industries, Ltd.), 15 g of agar powder (Syoei Kanten Ltd.) and 50 mg of sodium D[−]-α-aminobenzylpenicillin (Ampicillin) (Sigma Chemical Co.)], and then allowed to stand at 37° C. overnight to give transformants.

Each colony of the resulting transformants was subjected to colony direct PCR to select correct transformants. Namely, M13 forward primer and M13 reverse primer (0.5 μM each) were mixed with 0.625 Unit of DNA polymerase "AmpliTaq Gold" (PE Biosystems) and 2.5 μL of ×10 PCR buffer II (PE Biosystems) as a reaction buffer. Each reaction system was also added with $MgCl_2$ and dNTPs in concentrations of 1.5 mM and 200 μM, respectively. The reaction system was made up to a total volume of 25 μL with distilled water. The colony was picked up with a toothpick and then suspended in the reaction system.

The reaction conditions employed were as follows: maintaining for 5 minutes at 95° C., 35 cycles of 30 seconds at 95° C., 30 seconds at 50° C. and 90 seconds at 72° C., followed by maintaining for 90 seconds at 72° C. and keeping at 4° C.

The resulting PCR amplification products were subjected to agarose gel electrophoresis. Colonies containing amplification products that had be found to conform to the intended design were cultured in 40 mL of LB (ampicillin) liquid medium [composition per L: 10 g of tryptone peptone (Difco Laboratories), 5 g of yeast extract (Difco Laboratories), 5 g of NaCl (Wako Pure Chemical Industries, Ltd.) and 50 mg of sodium D[−]-α-aminobenzylpenicillin (Ampicillin) (Sigma Chemical Co.)] at 37° C. overnight.

Plasmids were extracted from a large-scale culture of *E. coli* transformants using QIAGEN Plasmid Maxi Kit (QIAGEN GmbH). The extraction of the plasmids was performed following the protocol attached to the kit.

Figure 7:
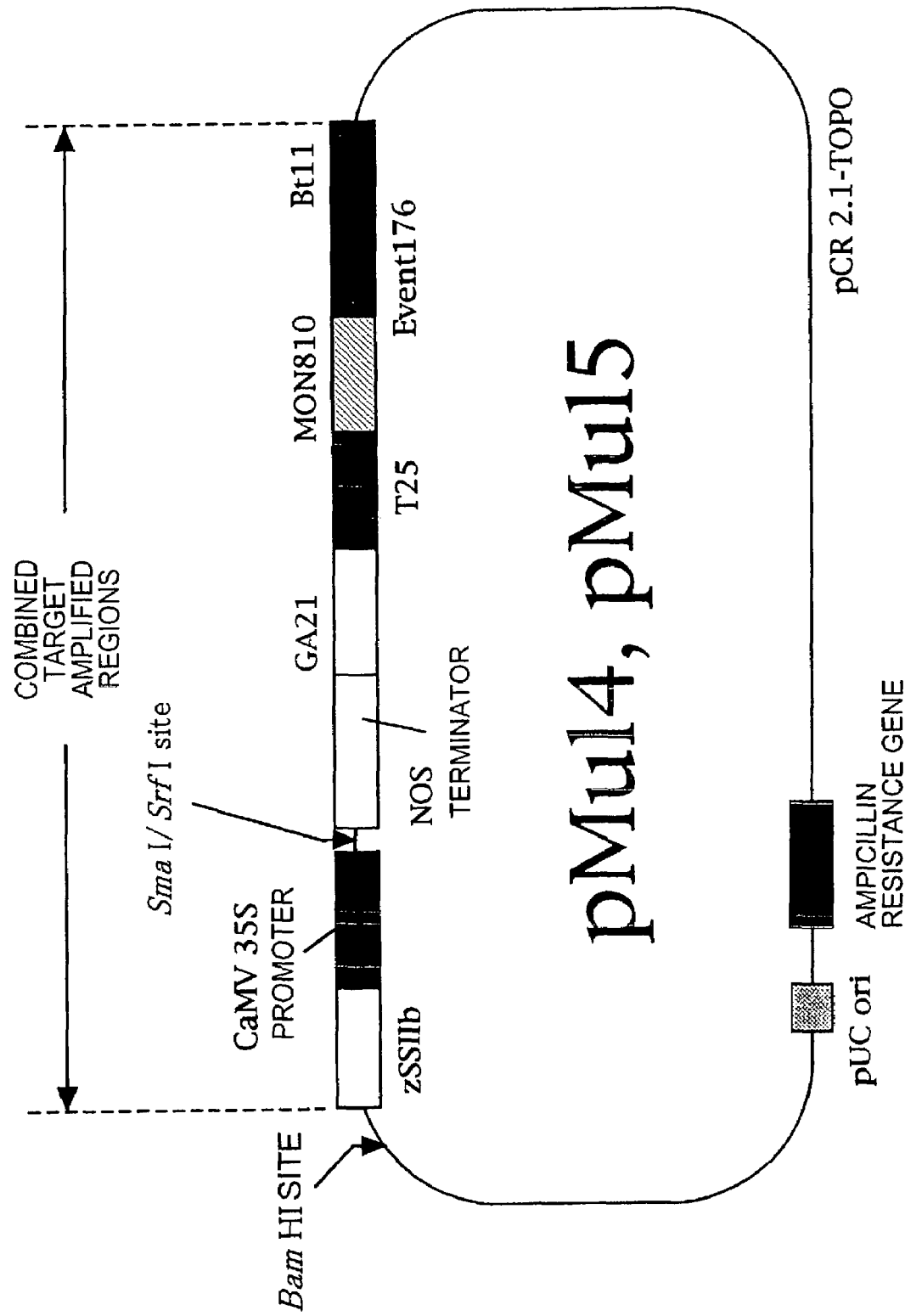
FIG. 7 shows the schemes of the plasmids pMul4 and pMul5. For pMul4 the DNA shown in FIG. 5 was inserted into the vector. For pMul5 the DNA sequence shown in FIG. 6 was inserted into the vector.

The resulting plasmids were confirmed the correct nucleotide sequence and used as standard molecules (pMul4 and pMul5: FIG. 7). Both of *E. coli*-ASN-pMul4 which carries plasmid pMul4 and *E. coli*-ASN-pMul5 which carries plasmid pMul5 have been deposited at Research Institute of Biotechnological & Industrial Science, Institute of Industrial Science and Technology, Ministry of International Trade and Industry, at 1-3, Higashi 1-chome, Tsukuba-shi, Ibaragi-ken, 305-8566 Japan (currently named "Independent Administrative Institution, National Institute of Advanced Industrial Science and Technology, International Patent Organism Depository", at 1-1-1 Higashi, Tsukuba-shi, Ibaragi-ken, Tsukuba Central 6, 305-8566 Japan) under Accession Nos. FERM BP-7319 and FERM BP-7320 on Oct. 12, 2000.

When these molecules were used in quantitative PCR, they were used in the form of a linearized molecule prepared by digesting with restriction enzyme BamHI. In the examples below, a BamHI digest of pMul4 (hereinafter, pMul4 BamHI digest) was used as the standard molecule.

Example 6

Production of Standard Molecule (Soybean)

The integration of the target regions to be detected which had been selected in Example 2 was performed according to the procedure schematically shown in FIG. 4, as in the case of Example 5.

Namely, PCR was performed using the tailed primers shown in Table 5 and the DNA extracted from the corresponding genetic recombinant line (a template) to give a PCR product having on the terminus other sequence complementary to the region to be detected. The resulting PCR product was, together with the PCR product in which the region to be adjacent to the region contained in that PCR product was amplified, was subjected to integration reaction utilizing PCR.

The detailed conditions employed in the experiment above were the same as those employed in Example 5.

As a result of the integration reaction, molecules shown in FIGS. 8 and 9 were obtained. The molecule shown in FIG. 8 has a Roundup Ready Soy line-specific DNA sequence of amplification target integrated between nucleotide 1 and 121 and a le1 (GENBANK Accession No. K00821 M30884) DNA sequence of amplification target integrated between nucleotide 122 to 239. The nucleotide sequence of the molecule of FIG. 8 is shown in SEQ ID NO:75.

The molecule shown in FIG. 9 has a Roundup Ready Soy line-specific DNA sequence of amplification target integrated between nucleotide 1 and 121, a le1 DNA sequence to be amplified integrated between nucleotide 122 to 239, a NOS terminator DNA sequence of amplification target integrated between nucleotide 240 to 419 and a CaMV 35S promoter DNA sequence of amplification target integrated between nucleotide 428 to 528. The nucleotide sequence of the molecule of FIG. 9 is shown in SEQ ID NO:75.

<Sequence Listing Free Text>

SEQ ID NOs: 75 and 76: Target regions for amplification of standard molecules to be used for quantitative detection of soybean genetic recombinants.

Figure 10:
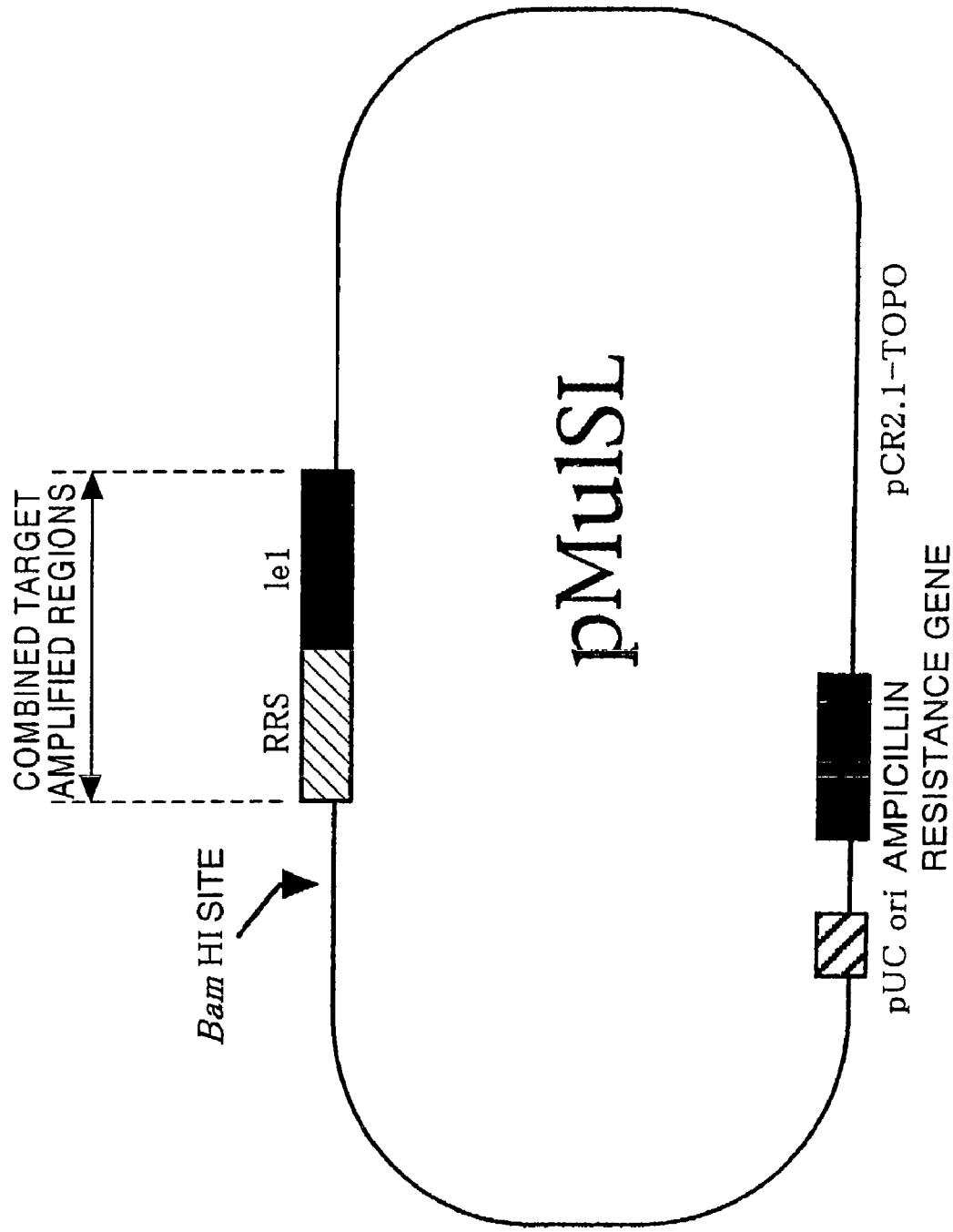
FIG. 10 shows the scheme of the plasmid pMulSL. The sequence introduced into the vector is the DNA sequence shown in FIG. 8.
Figure 11:
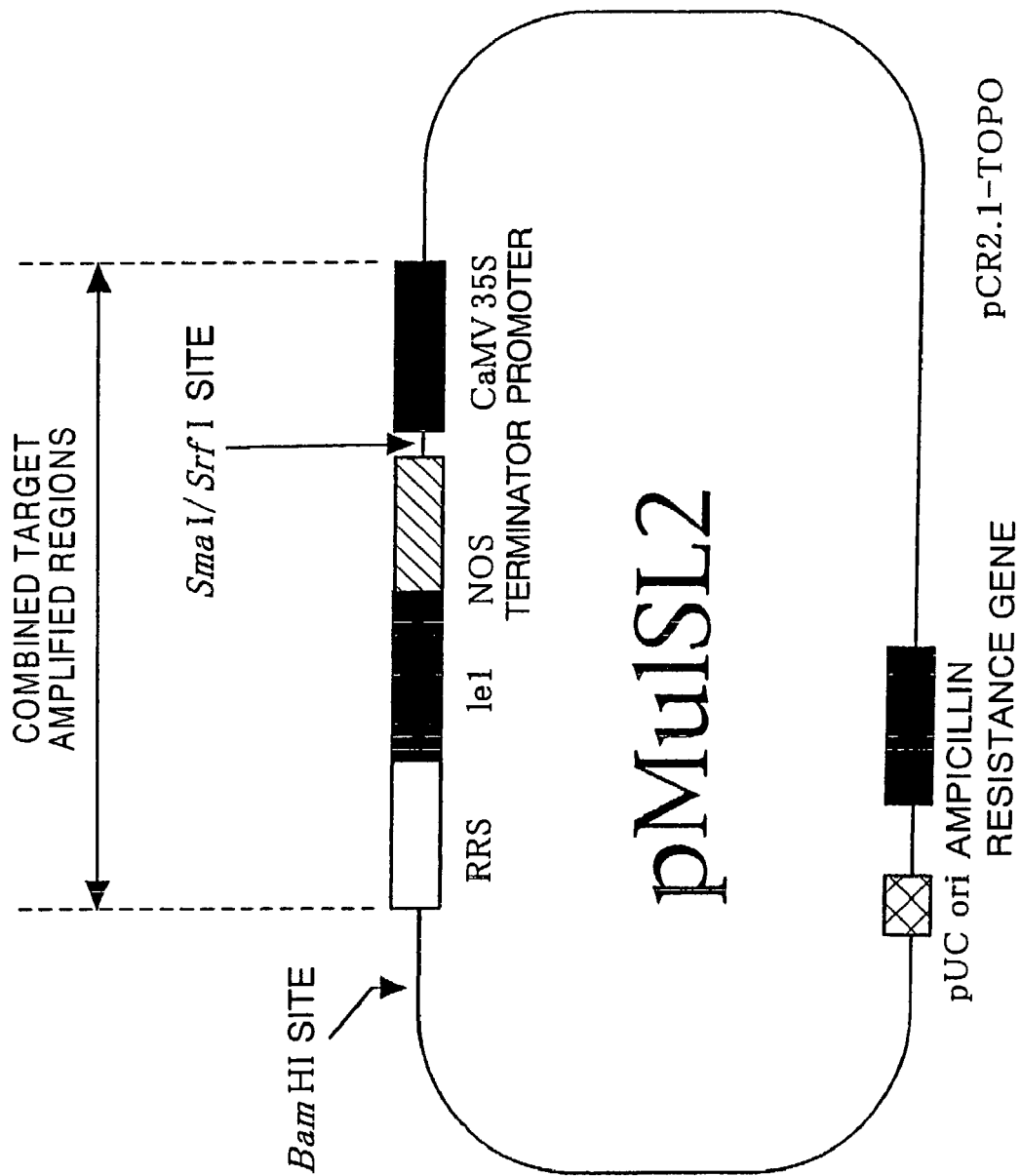
FIG. 11 shows the scheme of the plasmid pMulSL2. The sequence introduced into the vector is the DNA sequence shown in FIG. 9.

Each of the integrated molecules prepared above was ligated into a plasmid vector using TOPO TA Cloning Kit with TOP 10F' Cells (Invitrogen Co.), and an *E. coli* host vector system was used so that the molecule could be supplied readily and infinitely, in the same manner as in Example 5. The resulting plasmids were confirmed the correct nucleotide sequence and used as standard molecules (pMulSL and pMulSL2: FIGS. 10 and 11). Both of *E. coli*-ASN-pMulSL which carries plasmid pMulSL and *E. coli*-ASN-pMulSL2 which carries plasmid pMulSL2 have been deposited at Research Institute of Biotechnological & Industrial Science, Institute of Industrial Science and Technology, Ministry of International Trade and Industry, at 1-3, Higashi 1-chome, Tsukuba-shi, Ibaragi-ken, 305-8566 Japan (currently called "Independent Administrative Institution, National Institute of Advanced Industrial Science and Technology, International Patent Organism Depository", 1-1-1 Higashi, Tsukuba-shi, Ibaragi-ken, Tsukuba Central 6, 305-8566 Japan) under Accession Nos. FERM BP-7321 and FERM BP-7322 on Oct. 12, 2000.

When these molecules were used in quantitative PCR, they were used in the form of a linearized molecule prepared by digesting with restriction enzyme BamHI. In the examples below, a BamHI digest of pMulSL (hereinafter, pMulSL BamHI digest) was used as the standard molecule.

Example 7

Use as Positive Control for Qualitative Analysis

DNA samples extracted from 1 g each of progeny varieties from Bt11 line, GA21 line and MON810 line were mixed together in equal amounts. A DNA solution was prepared using the DNA mixture in a DNA concentration of 20 ng/μL. The DNA solution was used as a blind maize sample, and the presence of genetic recombinant maize in the sample was examined by qualitative PCR using the standard molecule as a positive control.

Devices and conditions (e.g., compositions of reaction solutions) employed in the experiment were the same as those employed in Example 3. Qualitative PCR was conducted for all of the primer pairs shown in Table 2. In the experiment, the DNA solution prepared above was used as a PCR template, the standard molecule pMul4 BamHI digest described in Example 5 was used as a positive control, and distilled water was used as a negative control. The standard molecule pMul4 BamHI digest was used in an amount of 500 molecules per reaction system.

As in the case of Example 3, after the reaction was completed, 5 μL was sampled from the reaction solution and subjected to electrophoresis on 3% agarose gel and stained with ethidium bromide, and the presence of a PCR amplification product was confirmed using an image analyzer.

As a result of the experiment, as shown in FIG. 12, it was confirmed that progeny varieties from Bt11 line, GA21 line and MON810 line were contained in the sample as genetic recombinant maize. It was also confirmed that the standard molecule pMul4 BamHI digest could be used suitably as a positive control for qualitative analysis.

In particular, with respect to the progeny varieties from GA21 line and MON810 line, since no standard sample is commercially available at present, positive controls for these lines have been unavailable to ordinary analysts.

Example 8

Determination of Quantification Ratio (Preliminary Test—Maize)

Since maize is a heterotic hybrid, a genetically uniform F1 seed population or a seed population equivalent thereto is required for determining a correct quantification ratio. Thus, as the preliminary test, genetic uniformity of seeds was first confirmed by quantitative PCR.

As the samples of the preliminary test, F1 seeds were used for the progeny varieties from Bt11 line, Event176 line, MON810 line and GA21 line. For the progeny variety from T25 line, since F1 seeds was not available, F2 seeds were used instead. The details of the experiment are described in the following.

Figure 13:
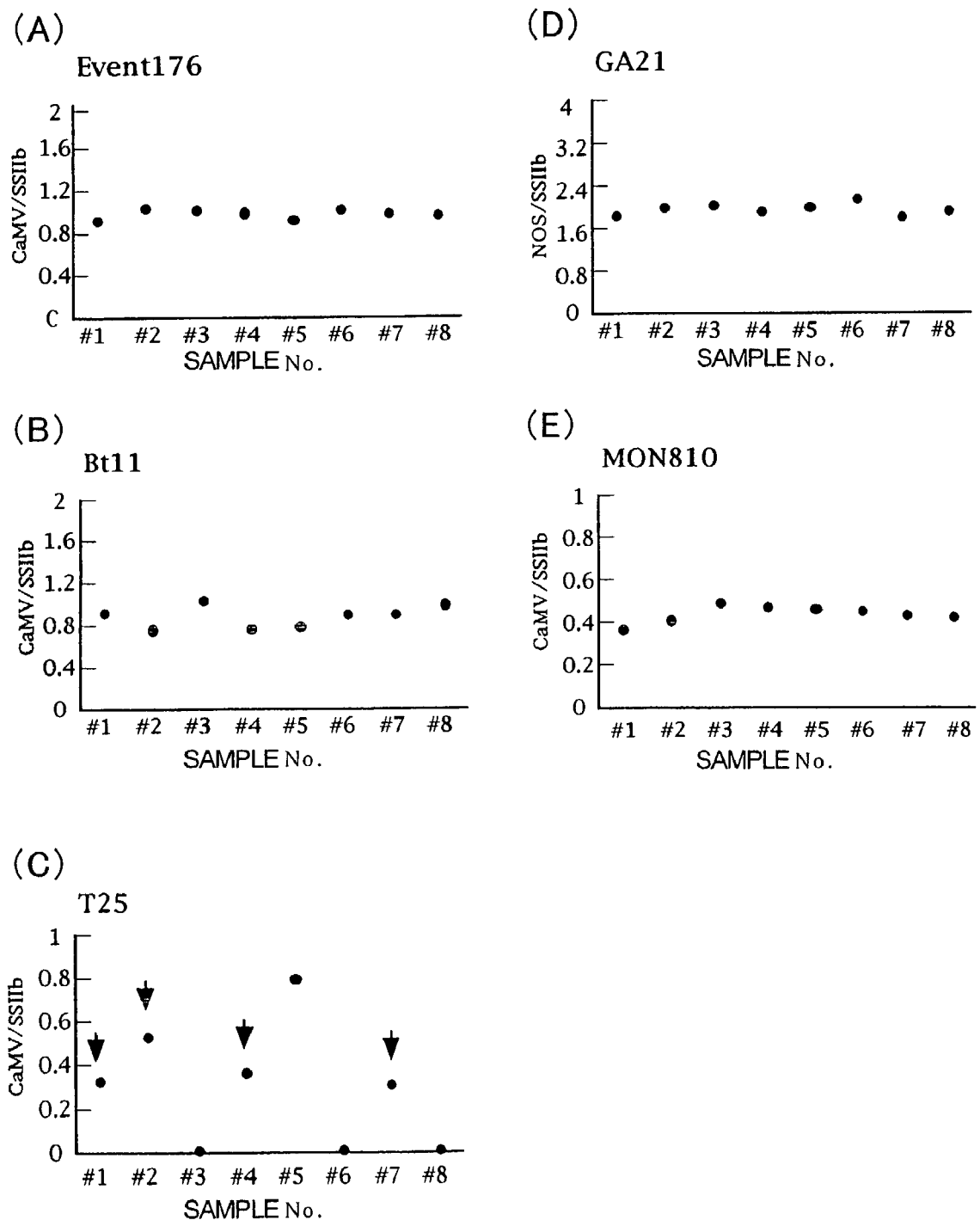
FIGS. 13A to 13E show the result confirming the quantification ratio by performing PCR using the DNA extracted from a single maize sample and calculating the ratio according to formula (II). The arrows in the FIG. 13C indicate the predicted values which F1 seed from the progeny varieties from T25 line may exhibit.

DNA was extracted from each of eight seeds of the individual five varieties above, and the numbers of molecules of the target regions to be detected (which were selected in Example 2) in the extracted DNA were determined using the pMul4 BamHI digest described in Example 5 as a standard sample. Namely, for the DNA sequence of maize endogenous gene zSSIIb to be amplified, quantitative PCR was performed using the DNA extracted from each of the five varieties as a template to determine the number of molecule of the region in the sample. For the DNA sequence of CaMV 35S promoter to be amplified, quantitative PCR was performed using the DNA extracted from each of progeny varieties from Bt11 line, Event176 line, MON810 line and T25 line as a template to determine the number of molecule of the region in the sample. For the DNA sequence of NOS terminator to be amplified, quantitative PCR was performed using the DNA extracted from each of the progeny varieties from Bt11 line and GA21 line as a template to determine the number of molecule of the region in the sample. The measurement values given by the experiment were used to calculate quantification ratio for the individual lines according to the formula (II) (FIG. 13)

The experiments were performed using a quantitative PCR apparatus "ABI PRISM 7700 Sequence Detector System" (PE Biosystems). In the experiment, the final primer concentration of each PCR solution was 0.5 μM for all of the primers used for quantification of CaMV 35S promoter, NOS terminator and zSSIIb; and the final probe concentration was 0.2 μM for all of the probes used for quantification of CaMV 35S promoter, NOS terminator and zSSIIb. The DNA extracted from each sample as a template was used in an amount of 50 ng per reaction system, and TaqMan Universal PCR Master Mix (PE Biosystems; simply referred to as "Master Mix" hereinafter) was used in a volume of 12.5 μL per reaction system. Each reaction system was made up to 25 μL. The same reaction was performed in tetraplicate and the measurement values were averaged.

The conditions employed in the reaction were as follows: maintaining the reaction solution for 2 minutes at 50° C. and then for 10 minutes at 95° C., 40 cycles of 30 seconds at 95° C. and 1 minute at 59° C., followed by keeping at 25° C.

For the quantitative determination of CaMV 35S promoter, a reaction tube was charged with each of 12 kinds of samples consisting of: the standard molecule pMul4 BamHI digest prepared in three concentrations (250 molecules, 1,000 molecules and 50,000 molecules per reaction system) as a standard recombinant DNA sequence; the DNA solutions extracted from the individual seeds (eight samples in total for each variety) as test samples; and a salmon spermary DNA solution as a negative control. A primer pair and a probe for quantification of CaMV 35S promoter and Master Mix were added to each of the test tubes in the final concentrations indicated above to give a reaction solution.

Similarly, for the quantitative determination of NOS terminator, a reaction tube was charged with each of 12 kinds of samples consisting of: the standard molecule pMul4 BamHI digest prepared in three concentrations (250 molecules, 1,000 molecules and 50,000 molecules per reaction system) as a standard recombinant DNA sequence; the DNA solutions extracted from the individual seeds (eight samples in total for each variety) as test samples; and a salmon spermary DNA solution as a negative control. A primer pair and a probe for quantification of NOS terminator and Master Mix were added to each of the test tubes in the final concentrations indicated above to give a reaction solution.

Similarly, for the quantitative determination of endogenous gene zSSIIb, a reaction tube was charged with each of 12 kinds of samples consisting of: the standard molecule pMul4 BamHI digest prepared in three final concentrations (250 molecules, 1,000 molecules and 50,000 molecules per reaction system) as a standard recombinant DNA sequence; the DNA solutions extracted from the individual seeds (eight samples in total for each variety) as test samples; and a salmon spermary DNA solution as a negative control. A primer pair and a probe for quantification of zSSIIb and Master Mix were added to each of the test tubes in the final concentrations indicated above to give a reaction solution.

During the reaction, the degree of degradation of the probe caused by the PCR amplification was determined over time in terms of the increase in fluorescent intensity. Accordingly, by generating a graph (cycles—fluorescent intensity) for the three kinds of samples provided as the standards for the quantification (×4) (see FIG. 14), a correlation function between the number of molecules of a target DNA sequence to be amplified and the number of cycles required for the fluorescent intensity to reach a specified value (i.e., threshold cycle) can be obtained (see FIG. 15). Using the correlation function as a standard curve, the numbers of molecule of the DNA sequence of CaMV 35S promoter to be amplified, the DNA sequence of NOS terminator to be amplified and the DNA sequence of zSSIIb to be amplified present in a quantification sample at the beginning of the reaction can be determined (Table 6).

TABLE 6

The number of molecules of zSSIIB, CaMV 35S promoter and NOS, respectively

| Sample | zSSIIb | CaMV | NOS |
|---|---|---|---|
| Bt11 | | | |
| #1 | 34700 | 31800 | |
| #2 | 56500 | 43000 | |
| #3 | 26200 | 27000 | |
| #4 | 38400 | 29400 | |
| #5 | 38100 | 29600 | |
| #6 | 34000 | 30300 | |
| #7 | 32300 | 28900 | |
| #8 | 31800 | 31200 | |

TABLE 6-continued

The number of molecules of zSSIIB, CaMV 35S promoter and NOS, respectively

| Sample | zSSIIb | CaMV | NOS |
|---|---|---|---|
| T25 | | | |
| #1 | 35200 | 11500 | |
| #2 | 40900 | 21600 | |
| #3 | 29800 | 200 | |
| #4 | 33700 | 12300 | |
| #5 | 22900 | 18000 | |
| #6 | 27100 | 0 | |
| #7 | 30400 | 9400 | |
| #8 | 44300 | 100 | |
| Event176 | | | |
| #1 | 37000 | 33800 | |
| #2 | 38800 | 40000 | |
| #3 | 33800 | 34300 | |
| #4 | 32800 | 32300 | |
| #5 | 36800 | 33500 | |
| #6 | 31500 | 31800 | |
| #7 | 36000 | 35000 | |
| #8 | 36300 | 34500 | |
| MON810 | | | |
| #1 | 30600 | 13700 | |
| #2 | 34700 | 14100 | |
| #3 | 32900 | 11900 | |
| #4 | 30700 | 14600 | |
| #5 | 30300 | 12500 | |
| #6 | 33600 | 14400 | |
| #7 | 31600 | 13100 | |
| #8 | 25000 | 10300 | |
| GA21 | | | |
| #1 | 15100 | | 27600 |
| #2 | 14700 | | 29300 |
| #3 | 14100 | | 28500 |
| #4 | 17400 | | 33700 |
| #5 | 15100 | | 29900 |
| #6 | 10600 | | 22700 |
| #7 | 14300 | | 25700 |
| #8 | 13500 | | 25700 |

As shown in FIG. 13, for the progeny varieties from Bt11 line, Event176 line, MON810 line and GA21 line, the quantification ratios were almost constant among the DNA samples from the eight seeds, and the seed samples were confirmed to be genetically uniform F1 populations. For the progeny variety from T25 line of which F1 seeds were not available, however, the integrated DNA sequence showed a progeny distribution following Mendel's Laws as expected. Thus, for the progeny variety from T25 line, only the seeds which had been confirmed to have the identical genetic structure to that of the F1 population (marked with arrows in FIG. 13) were selected, and a population of the seeds was used in the subsequent experiments as the seed population equivalent to a genetically uniform F1 seed population.

Example 9

Determination of Quantification Ratio (Preliminary Test—Soybean)

The preliminary test was performed on soybean in the same manner as in Example 8. F1 seeds of a progeny variety from Roundup Ready Soy line were used as the samples for the preliminary test.

DNA was extracted from eight F1 seeds of the progeny variety from Roundup Ready Soy line separately in the same manner as in Example 8, and the numbers of molecules of the target regions to be detected (which had been selected in Example 2) in the extracted DNA samples were determined using the pMulSL BamHI digest described in Example 6 as a standard sample.

Namely, quantitative PCR using the extracted DNA as a template was performed for a DNA sequence of soybean endogenous gene le1 of amplification target and a DNA sequence specific to Roundup Ready Soy line of amplification target separately, and the numbers of molecules of the individual regions in the samples were determined. The measurement values obtained in the experiment were used to calculate the quantification ratios according to the formula (II) (FIG. 16).

The devices and conditions (e.g., compositions of reaction solutions) employed in the experiment are the same as those in Example 8, except that primers and probes corresponding to the DNA sequence of soybean endogenous gene Le1 to be amplified and the DNA sequence specific to Round Ready Soy line to be amplified were used.

Figure 16:
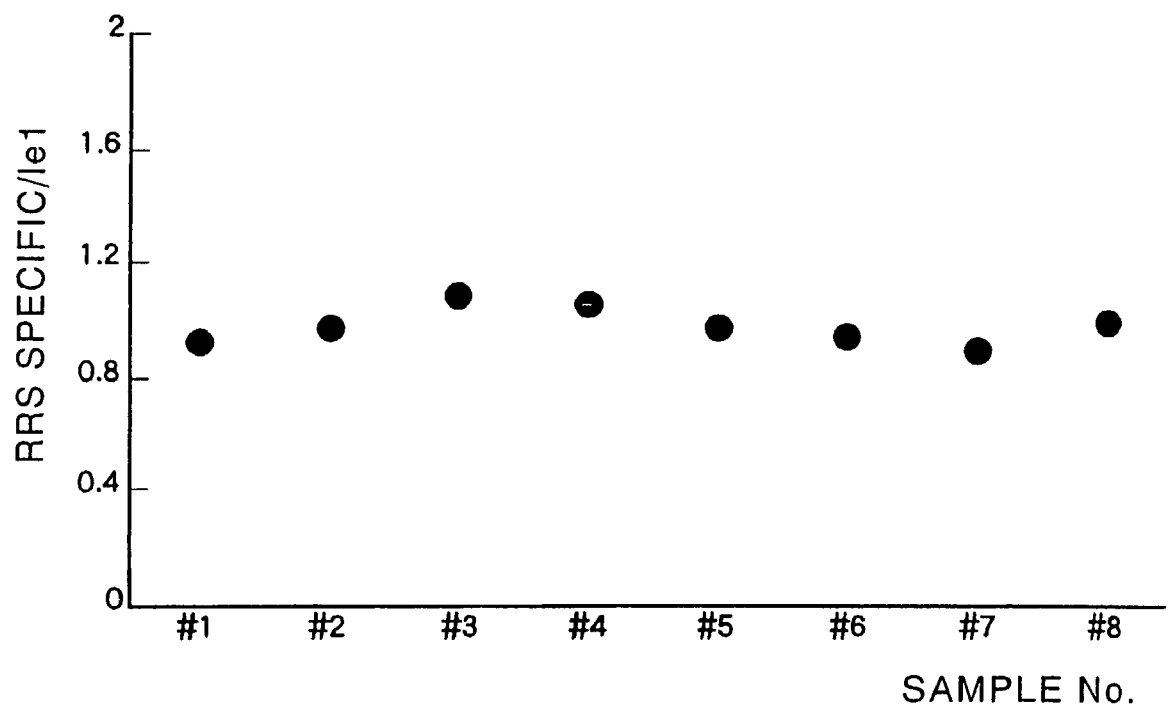
FIG. 16 shows the result confirming the quantification ratio by conducting PCR using the DNA extracted from a single soybean seed and calculating the quantification ratio according to formula (II).

As a result of the experiment, as shown in FIG. 16, for the progeny variety from Roundup Ready Soy line, the calculated quantification ratios was almost constant among the DNA samples from the eight seeds, and the seed samples were confirmed to be a genetically uniform F1 population, which were used in the subsequent experiments.

Example 10

Determination of Quantification Ratio (Maize)

Test for determining the quantification ratio was performed using the genetically uniform F1 seed populations and the equivalent seed population obtained in the preliminary tests. For each variety, the numbers of molecules of the target regions to be detected (selected in Example 2) in the extracted DNA were determined using the DNA samples extracted from the genetically uniform populations as templates and the pMul4 BamHI digest described in Example 5 as a standard sample in the same manner as in the preliminary test.

In the test, in addition to the DNA sequences of amplification target quantified in the preliminary test, the variety-specific DNA sequences of amplification target were also examined. For the variety-specific DNA sequences of amplification target, the numbers of molecules of the target regions in the sample were determined for the individual corresponding varieties.

As in the case of Example 9, the devices and conditions (e.g., compositions of reaction solutions) employed in the experiment were the same as those in Example 8, except that different primers and probes were used for different targets to be amplified.

As in the case of the preliminary test, the measurement values were used to calculate the quantification ratios according to the formula (II). Namely, each of the numbers of molecules of the DNA sequence of CaMV 35S promoter of amplification target, the DNA sequence of NOS terminator of amplification target and the variety-specific target DNA sequences was divided by the number of molecules of zSSIIb DNA sequence of amplification target which was respectively determined in the identical samples to give the quantification ratios unique to the individual DNA sequences (Table 7).

TABLE 7

Quantification ratio (Kx) of maize genetic recombinant line (X)

| Line | CaMV 35S promoter | NOS terminator | Specific target |
|---|---|---|---|
| Bt11 | $k_{CaMV(Bt)} = 1.04$ | $k_{NOS(Bt)} = 1.82$ | $k_{Bt} = 0.49$ |
| T25 | $k_{CaMV(T)} = 0.37$ | | $k_T = 0.34$ |
| GA21 | | $k_{NOS(GA)} = 2.03$ | $k_{GA} = 2.30$ |
| Event176 | $k_{CaMV(EV)} = 0.99$ | | $k_{Ev} = 0.45$ |
| MON810 | $k_{CaMV(MON)} = 0.38$ | | $k_{MON} = 2.76$ |

As the primer to be used for the amplification of the endogenous gene zSSIIb, two sets of primers designed for a shorter sequence of amplification target (SSIIB 2-5'/SSIB 2-3' and SSIIb3-5'/SSIB 3-3') were also used. The quantification ratios determined using these primers as the primers for amplification of the endogenous gene were also determined (Tables 8 and 9).

TABLE 8

Quantification ratio by SSIIb 2-5'/SSIIb 2-3'

| Line | Specific target |
|---|---|
| Bt11 | $k_{Bt} = 0.51$ |
| T25 | $k_T = 0.38$ |
| GA21 | $k_{GA} = 2.08$ |
| Event176 | $k_{Ev} = 2.32$ |
| MON810 | $k_{MON} = 0.39$ |

TABLE 9

Quantification ratio by SSIIb 3-5'/SSIIb 3-3'

| Line | Specific target |
|---|---|
| Bt11 | $k_{Bt} = 0.53$ |
| T25 | $k_T = 0.39$ |
| GA21 | $k_{GA} = 1.87$ |
| Event176 | $k_{Ev} = 2.15$ |
| MON810 | $k_{MON} = 0.43$ |

Example 11

Determination of Quantification Ratio (Soybean)

For soybean, test for determining the quantification ratio was also performed using the genetically uniform seed population obtained in the preliminary test. For each variety, the numbers of molecules of the target DNA sequence to be amplified of soybean endogenous gene le1 in the extracted DNA and the DNA sequence specific to Roundup Ready Soy line were determined separately using the DNA extracted from the genetically uniform population as a template and the pMulSL BamHI digest as a standard sample in the same manner as in the preliminary test.

As in the case of Example 9, the devices and conditions (e.g., compositions of reaction solutions) employed in the experiment were the same as those in Example 8, except that different primers and probes were used for different targets.

The measurement values were used to calculate the quantification ratios according to the formula (II) in the same manner as in the preliminary test. Namely, the number of molecules of the DNA sequence specific to Roundup Ready Soy line was divided by the number of the DNA sequence to be amplified of soybean endogenous gene le1 determined in the same sample to give the quantification ratios of the DNA sequences specific to Roundup Ready Soy line unique to the line (Table 10).

TABLE 10

Quantification ratio (Kx) of soybean genetic recombinant line (X)

| Line | CaMV 35S promoter | NOS terminator | Specific target |
|---|---|---|---|
| Roundup Ready Soy | not determined | not determined | $k_{RRS} = 0.90$ |

Example 12

Quantification Using Blind Samples

A ground product of each of genetic recombinant line was mixed with a ground product of a non-recombinant line to prepare a blind sample. The blind sample was actually determined on the content ratio of the individual genetic recombinant lines to assess the efficacy of the present quantitative analysis method.

Namely, blind samples were prepared using seeds of genetic recombinant lines and a non-recombinant line as described in Example 1, and DNA was extracted from the blind samples. In the test for maize, as the blind samples, in total 12 kinds of mixtures were prepared which contained 0.1%, 1% and 5% (by weight) of each of the seeds of progeny varieties from Bt11 line, Event176 line, MON810 line and T25 line, respectively.

Quantitative PCR was performed using the DNA extracted from each blind sample as a template and the standard molecule prepared in Example 5 which was linearized by digesting with restriction enzyme BamHI (pMul4 BamHI digest) to determine the numbers of molecules of the DNA sequence to be amplified of the endogenous gene and the DNA partial sequence to be amplified of the recombinant DNA sequence separately in the blind sample. The content ratio of the genetic recombinant in the sample was determined from the results using the quantification ratio determined in Example 10 or 11.

In the quantification reaction for every target, each of the primers and the probe to be used for quantification were used in a PCR reaction solution in final concentrations of 0.5 µM and 0.2 µM, respectively. The DNA extracted from a sample (a template) and Master Mix were used in amounts of 50 ng and 12.5 µL, respectively, per reaction system. The reaction system was made up to 25 ρL. The same reaction was performed in tetraplicate, and the resulting measurements were averaged.

The reaction conditions employed were as follows: maintaining the reaction solution for 2 minutes at 50° C. and then for 10 minutes at 95° C., 40 cycles of 30 seconds at 95° C. and 1 minute at 59° C., followed by keeping at 25° C.

In the quantitative determination of each of the target DNA sequences to be amplified, a reaction tube was charged with each of 9 kinds of samples consisting of: standard molecule pMul4 BamHI digest prepared in five concentrations (10, 50, 250, 1,000 and 50,000 molecules per reaction system); the DNA solutions extracted from the 0.1%, 1% and 5% blind samples as test samples; and a salmon spermary DNA solution. A primer pair, a probe for quantification and Master Mix were added to the reaction tube at the final concentrations described above to give a reaction solution.

During the reaction, the degree of degradation of the probe caused by the PCR amplification was determined over time in terms of the increase in fluorescent intensity. Accordingly, by generating a graph (cycles—fluorescent intensity) for the five samples provided as the standard recombinant DNA sequences (×4), a correlation function between the number of molecules of a target DNA sequence to be amplified and the number of cycles required for the intensity of the fluorescence emitted from the reaction system to reach a specified value can be obtained. Using the correlation function as a standard curve, the numbers of molecules of the target DNA sequences to be applied in the samples present at the beginning of the reaction can be determined (Table 11).

TABLE 11

The number of each target DNA sequence for amplification

| Sample | zSSIIb | CaMV |
|---|---|---|
| 0.1% Bt11 | 34378.45 | 43.67 |
| 1% Bt11 | 44943.75 | 574.30 |
| 5% Bt11 | 42690.63 | 2375.83 |
| 0.1% T25 | 48665.87 | 23.88 |
| 1% T25 | 48664.95 | 186.42 |
| 5% T25 | 61333.30 | 1040.07 |
| 0.1% Event176 | 96960.50 | 91.73 |
| 1% Event176 | 63402.34 | 704.80 |
| 5% Event176 | 31765.13 | 1607.65 |
| 0.1% MON810 | 40662.60 | 14.85 |
| 1% MON810 | 44822.75 | 202.26 |
| 5% MON810 | 31624.09 | 641.39 |

| Sample | Content ratio of genetic recombinant maize in the sample (observed) | Content ratio of genetic recombinant maize in the sample (theoretical) | Quantification ratio (Formula II) |
|---|---|---|---|
| 0.1% Bt11 | 0.12% | 0.10% | $k_{CaMV(Bt)} = 1.04$ |
| 1% Bt11 | 1.23% | 1.00% | |
| 5% Bt11 | 5.35% | 5.00% | |
| 0.1% T25 | 0.13% | 0.10% | $k_{CaMV(T)} = 0.37$ |
| 1% T25 | 1.04% | 1.00% | |
| 5% T25 | 4.58% | 5.00% | |
| 0.1% Event176 | 0.10% | 0.10% | $k_{CaMV(Event)} = 0.99$ |
| 1% Event176 | 1.12% | 1.00% | |
| 5% Event176 | 5.11% | 5.00% | |
| 0.1% MON810 | 0.10% | 0.10% | $k_{CaMV(MON)} = 0.39$ |
| 1% MON810 | 1.19% | 1.00% | |
| 5% MON810 | 5.34% | 5.00% | |

The measurement values for the numbers of molecules of the DNA sequences can be converted into the content ratio of the individual genetic recombinants according to the formula (I) using the quantification ratios given in Examples 10 and 11. The results of the conversion are shown in Table 11. In either case, it was found that blind samples containing progeny varieties from genetic recombinant lines in amount of 0.1%, 1% or 5% can be determined quantitatively determined satisfactorily.

Example 13

Quantification of Content Ratio of Genetic Recombinant Using Standard Molecule (1)

Blind samples each containing three kinds of maize genetic recombinant lines were prepared. Quantitative PCR targeting CaMV 35S promoter and a specific endogenous gene zSSIIb from maize was performed on the blind samples to determine the content ratios of the maize genetic recombinant lines in the samples. As the standard material, pMul4 BamHI digest described in Example 5 was used.

The blind maize samples used in the experiment were as follows: a sample containing ground products of progeny varieties from Bt11 line, Event176 line and MON810 line as maize genetic recombinants each in an amount of 1% (by weight) and a ground product of Dairyland 1412 in an amount of 97% (by weight) as a non-recombinant maize (1% mixture); and a sample containing ground products of progeny varieties from Bt11 line, Event 176 line and MON810 line as maize genetic recombinants each in an amount of 5% (by weight) and a ground product of Dairyland 1412 in an amount of 85% (by weight) as a non-recombinant maize (5% mixture).

In the experiment, in order to simulate real situations of analysis, it was assumed that analysts were given no information about the content of any of the three kinds of maize genetic recombinant lines in the samples.

Again, in the PCR reaction solutions, the final primer concentration was 0.5 µM for each of the primers for analysis of CaMV 35S promoter and the primers for analysis of zSSIIb; the final probe concentration was 0.2 µM for each of the probe for analysis of CaMV 35S promoter and the probe for analysis of zSSIIb. The DNA extracted from the individual samples (template) and Master Mix were added in amounts of 50 ng and 12.5 µL, respectively, per reaction system. The reaction system was made up to 25 µL. The same reaction was performed in tetraplicate and the resulting measurements were averaged.

The reaction conditions employed were as follows: maintaining the reaction solution for 2 minutes at 50° C. and then for 10 minutes at 95° C., 40 cycles of 30 seconds at 95° C. and 1 minute at 59° C., followed by keeping at 25° C.

In the quantitative determination of CaMV 35S promoter, a reaction tube was charged with each of 7 kinds of samples consisting of: standard molecule pMul4 BamHI digest prepared in five concentrations (10, 50, 250, 1,000 and 50,000 molecules per reaction system) as a standard recombinant DNA sequence; a DNA solution extracted from each of the blind maize samples as a test sample; and a salmon sperm DNA solution as a negative control. A primer pair for quantification of CaMV 35S promoter, a probe for quantification of CaMV 35S promoter and Master Mix were added to the reaction tube at the final concentrations described above to give a reaction solution.

Similarly, in the quantitative determination of endogenous gene zSSIIb, a reaction tube was charged with each of 7 kinds of samples consisting of: standard molecule pMul4 BamHI digest prepared in five concentrations (10, 50, 250, 1,000 and 50,000 molecules per reaction system) as standard recombinant DNA sequence; a DNA solution extracted from each of the blind maize samples as a test sample; and a salmon sperm DNA solution as a negative control. A primer pair for quantification of zSSIIb, a probe for quantification of zSSIIb and Master Mix were added to the reaction tube at the final concentrations described above to give a reaction solution.

During the reaction, the degree of degradation of the probe caused by the PCR amplification was determined over time in terms of the increase in fluorescent intensity. Accordingly, by generating a graph (cycles—fluorescent intensity) for the five samples provided as the standard recombinant DNA sequence (×4), a correlation function between the number of molecules of a target DNA sequence to be amplified and the number of cycles required for the intensity of the fluorescence emitted from the reaction tube to reach a specified value can be obtained. Using the correlation function as a standard curve, the numbers of molecules of the DNA sequences of CaMV 35S promoter to be amplified and the DNA sequence of zSSIIb to be amplified present in the samples at the beginning of the reaction can be determined (Table 12).

The apparatus used for the quantitative determination ABI PRISM 7700 Sequence Detector System (PE Biosystems) is capable of conducting the reactions for 96 samples simultaneously. Hence, the test mentioned above can be made in one pass of quantitative PCR by using the apparatus.

The measurement values of the numbers of molecules of the DNA sequences can be converted into the content ratio of the individual genetic recombinants carrying CaMV 35S promoter according to the formula (I) using the quantification ratios given in Example 10. In the experiment, since no information about the content of any of the genetic recombinant lines in the samples was given, it was necessary to calculate the quantification ratios and expressed them as converted values for all of the three kinds of genetic recombinant lines. However, the content ratios of the genetic recombinant lines in the samples could be determined only in one pass of quantitative PCR advantageously (Table 12).

TABLE 12

Quantification of the content ratio of the genetic recombinants (1)

| Sample | zSSIIb | CaMV | Content ratio (observed) | Quantification ratio | Remarks |
|---|---|---|---|---|---|
| 1% mix*[1] | 7924.48 | 215.72 | 2.62% | 1.04 | converted to Bt11 |
| | | | 2.75% | 0.99 | converted to Event176 |
| | | | 7.16% | 0.39 | converted to MON810 |
| 5% mix*[2] | 8021.59 | 1065.46 | 12.77% | 1.04 | converted to Bt11 |
| | | | 13.42% | 0.99 | converted to Event176 |
| | | | 34.95% | 0.39 | converted to MON810 |

*[1]A blind sample containing 1% of Bt11, Event176 and MON810, respectively (containing 3% genetic recombinant maize in total)
*[2]A blind sample containing 5% of Bt11, Event176 and MON810, respectively (containing 15% genetic recombinant maize in total)

Example 14

Quantification of Content Ratio of Genetic Recombinant Using Standard Molecule (2)

The same blind samples as prepared in Example 13 were subjected to quantitative PCR targeting the DNA sequences specific to the three kinds of genetic recombinant maize lines, respectively, and a specific endogenous gene zSSIIb from maize to determine the content ratio of the individual genetic recombinant maize lines in the samples. The results and the sum of the quantification ratios obtained were used to determine the content ratio of the genetic recombinants in the samples. As in the case of Example 13, pMul4 BamHI digest described in Example 5 was used as the standard material.

In the experiment, in order to simulate real situations of analysis, it was assumed that analysts were given no information about the content of any of the three kinds of maize genetic recombinant lines in the samples.

The compositions of the reaction solutions, conditions for the reaction and the analysis methods were the same as in those employed in Example 13, except that the sequences specific to the progeny varieties from Bt11 line, Event176 line and MON810 line were separately quantified instead of CaMV 35S promoter. Namely, in the experiment, in total four kinds of the target DNA sequence to be amplified including zSSIIb were subjected to quantitative PCR separately. Therefore, in the experiment, ABI PRISM 7700 Sequence Detector System (PE Biosystems) was run three times in total.

The correlation between the number of molecules of the individual target DNA sequences to be amplification present at the beginning of the reaction and the number of cycles required for the intensity of the fluorescence emitted from the reaction tubes to reach a specified value was represented as a standard curve. Using the standard curve, the numbers of the individual line-specific target DNA sequences to be amplified in the assay samples at the beginning of the reaction and the number of the target region to be amplified of zSSIIb could be determined (Table 13).

As in the case of Example 13, the measurement values for the numbers of molecules of the DNA sequences can be converted into the content ratio of the individual genetic recombinant maize lines in the samples according to the formula (I) using the quantification ratio determined in Examples 10. In the experiment, since the quantitative determination was made on DNA sequences specific to the genetic recombinant lines, there was no concern that measurement values might vary which was found in Example 13. The method described above enable to determine the content ratio of the individual genetic recombinants in the samples more accurately, although the quantitative PCR apparatus had to be run plural times for performing the determination (Table 13).

TABLE 13

Quantification of the content ratio of the genetic recombinants (2)

| Sample | zSSIIb | target | Content ratio (observed) | Quantification ratio | Remarks |
|---|---|---|---|---|---|
| 1% mix*[1] | 8872.45 | 54.16 | 1.25% | 0.49 | converted to Bt11 |
| | 8270.42 | 222.64 | 1.17% | 2.30 0.45 | converted to Event176 |
| | 8041.05 | 38.83 | 1.07% | | converted to MON810 |
| | | | 3.49% | | Total |
| 5% mix*[2] | 8940.47 | 246.97 | 5.64% | 1.04 | converted to Bt11 |
| | 8631.57 | 1000.9 | 5.04% | 0.99 | converted to Event176 |
| | 8041.62 | 166.20 | 4.59% | 0.39 | converted to MON810 |
| | | | 15.23% | | Total |

*[1]A blind sample containing 1% of Bt11, Event176 and MON810, respectively (containing 3% genetic recombinant maize in total)
*[2]A blind sample containing 5% of Bt11, Event176 and MON810, respectively containing 15% genetic recombinant maize in total)

According to the method of the present invention, the presence of a possible genetic recombinant line(s) in a sample in which the presence of at least one genetic recombinant line is suspected can be determined; the content ratio of the genetic recombinant line(s) in the sample in which that content ratio is unknown in a simple manner; the content ratio of a genetic recombinant(s) in a population can be determined accurately; and, in particular, the content ratio of a certain genetic recombinant line in a sample in which that content ratio of the line is unknown can be determined accurately. In particular, the method of the present invention utilizes a standard molecule having in the molecule both of regions to be used for the quantitative determination of recombinant DNA sequences and a DNA sequence of an endogenous gene shared by the species corresponding to the recombinant DNA sequences. Since the standard molecule usually contains the regions to be used for the quantitative determination in an integral proportion depending on the pattern of the regions introduced, the quantification ratio represented by formula (II) can be determined with good reproducibility. Consequently, the method of the present invention enables to determine the content ratio of the individual specific genetic recombinant lines in a sample accurately.

Since the genetic recombinants in pure form become unnecessary after the determination of quantification ratios any longer, the difficulty of obtaining the standard molecules for analyst can be eliminated.

Moreover, by providing the standard molecules for the detection of genetic recombinants according to the present invention, the practical utility of molecular biological assays for genetic recombinants for which accurate analytical methods with wide applicability are widely available can be improved.

What is claimed is:

1. An in vitro quantitative detection method for determining the content ratio of a selected genetic recombinant line of a species in a sample which may contain the selected genetic recombinant line comprising:
  (i) preparing a first DNA by extraction of the DNA from the sample;
  (ii) preparing a standard molecule, which is a recombinant DNA molecule comprising a recombinant DNA sequence present only in said selected genetic recombinant line, and an endogenous DNA sequence of a non-recombinant line of the species, the endogenous DNA sequence being common to the selected recombinant line of the species and the non-recombinant line of the species, when the selected recombinant line exists in the sample;
  (iii) selecting the selected genetic recombinant line of the species from the sample and selecting a single DNA sequence specific for the selected genetic recombinant line when the selected genetic recombinant line is in the sample;
  (iv) preparing a second DNA, by extraction of the DNA from the selected genetic recombinant line of step (iii) when the selected genetic recombinant line is in the sample;
  (v) performing a quantitative polymerase chain reaction (PCR) using the second DNA as a template and a probe specifically hybridized to DNA sequence specific for the selected genetic recombinant line of step (iii), performing a quantitative PCR and preparing a first standard curve of the DNA sequence specific for the selected genetic recombinant line using sets of defined quantities of the standard molecule and the probe specifically hybridized to the DNA sequence specific for the selected genetic recombinant line, and determining the number of molecules of the DNA sequence specific for the selected genetic recombinant line in the second DNA using the first standard curve;
  (vi) performing a quantitative PCR using the second DNA as a template and a probe of the endogenous DNA sequence, performing a quantitative PCR and preparing a second standard curve using sets of defined quantities of the standard molecule and the probe of the endogenous DNA sequence, and determining the number of molecules of the endogenous DNA sequence in the second DNA using the second standard curve;
  (vii) performing a quantitative PCR using the first DNA as a template and the probe in step (v), and determining the number of molecules of the DNA sequence specific for the selected genetic recombinant line in the first DNA of step (i) using the first standard curve;
  (viii) performing a quantitative PCR using the first DNA as a template and the probe in step (vi), and determining the number of molecules of the endogenous DNA sequence in the first DNA extract of step (i) using the second standard curve; and
  (ix) determining the content ratio of the selected genetic recombinant line of the species in the sample according to formula (I):
    (content ratio of the selected genetic recombinant line of the species in the sample =100×((the number of molecules of the DNA sequence specific for the selected genetic recombinant line in the first DNA from step (vii))/(the number of molecules of the endogenous DNA sequence in the first DNA from step (viii)))/(quantification ratio) (%) wherein the quantification ratio is a value which is calculated according to formula (II): (quantification ratio) (%)=(the number of molecules of the DNA sequence specific for the selected genetic recombinant line in the second DNA from step (v))/(the number of molecules of the endogenous DNA sequence in the selected genetic recombinant line in the second DNA from step (vi)).

2. The method of claim 1, wherein the standard molecule of step (ii) is prepared for later use.

3. The method of claim 1, wherein the probes of steps (v) and (vii) are fluorescent labeled probes.

4. The method of claim 1, wherein said preparing the first or second standard curve further comprises the steps:
  (a) selecting a DNA sequence from the nucleotide sequences of the standard molecule from step (ii);
  (b) performing a quantitative PCR to amplify the selected DNA sequence in the presence of said set of defined quantities of the standard molecule in a plurality of tubes, using a primer for amplifying the selected DNA sequence and the probe specifically hybridized to the DNA sequence specific for the selected genetic recombinant line or the probe of the endogenous DNA sequence wherein the probe is labeled with a fluorescent dye and the probe degrades depending on the amplification of the selected DNA sequence to release the fluorescent dye, which leads to an increase in fluorescence intensity;
  (c) monitoring the fluorescence intensity at a predetermined number of PCR cycles;
  (d) determining a threshold of fluorescence increase (ΔRn) when an exponential relationship is observed between the fluorescence intensity and the number of the PCR cycles corresponding to the threshold; and
  (e) generating the standard curve by plotting:
    (A) the number of the PCR cycles of each of the plurality of tubes which contains different numbers of the standard molecule required for reaching the threshold, against (B) the numbers of the standard molecule in each of the plurality of tubes at the beginning of the PCR, wherein the number of the PCR cycles of each of the plurality of tubes which contains different numbers of the standard molecule required for reaching the threshold is used as the vertical axis of the standard curve, and the numbers of the standard molecule in each of the plurality of tubes at the beginning of the PCR cycle is used as the horizontal axis of standard curve.

5. The method of claim 1, wherein the standard molecule is capable of self replicating in a host cell.

6. The method of claim 1, further comprises selecting a primer for amplifying the endogenous DNA sequence wherein the primer comprises the sequence of SEQ ID NO:15 or NO:16 which is the 3'-terminal sequence of the primer and is capable of hybridizing with a maize zSSIIb gene sequence when the sample comprises maize recombinant lines.

7. The method of claim 1, wherein the probe of the endogenous DNA sequence comprises the sequence of SEQ ID NO:17 and is capable of hybridizing with a maize zSSIIb gene sequence when the sample comprises maize recombinant lines and the standard molecule contains a part of maize zSSIIb gene sequence.

8. The method of claim 1, wherein the sample comprises recombinant lines of maize or recombinant lines of soybean.

* * * * *